US012740797B2

(12) United States Patent
Yu

(10) Patent No.: US 12,740,797 B2
(45) Date of Patent: Sep. 22, 2026

(54) MEDICAL DEVICES HAVING COMPACT END EFFECTOR DRIVE MECHANISMS WITH HIGH GRIP FORCE

(71) Applicant: Intuitive Surgical Operations, Inc., Sunnyvale, CA (US)

(72) Inventor: Raymond Yu, Saratoga, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 451 days.

(21) Appl. No.: 18/029,532

(22) PCT Filed: Sep. 30, 2021

(86) PCT No.: PCT/US2021/053024
§ 371 (c)(1),
(2) Date: Mar. 30, 2023

(87) PCT Pub. No.: WO2022/072732
PCT Pub. Date: Apr. 7, 2022

(65) Prior Publication Data

US 2023/0355261 A1 Nov. 9, 2023

Related U.S. Application Data

(60) Provisional application No. 63/086,662, filed on Oct. 2, 2020.

(51) Int. Cl.
*A61B 17/29* (2006.01)
*A61B 34/00* (2016.01)
*A61B 34/30* (2016.01)

(52) U.S. Cl.
CPC .............. *A61B 17/29* (2013.01); *A61B 34/30* (2016.02); *A61B 34/71* (2016.02); *A61B 2017/2944* (2013.01)

(58) Field of Classification Search
CPC ............ A61B 17/29; A61B 2017/2927; A61B 2017/2932; A61B 2017/2933;
(Continued)

(56) References Cited

U.S. PATENT DOCUMENTS 4,728,137 A 3/1988 Hamed et al.
5,052,402 A 10/1991 Bencini et al.
(Continued)

FOREIGN PATENT DOCUMENTS

CN 106572889 A 4/2017
EP 2548529 A1 1/2013
(Continued)

OTHER PUBLICATIONS

International Search Report and Written Opinion for Application No. PCT/US2021/053024, mailed Feb. 7, 2022, 14 pages.
(Continued)

*Primary Examiner* — Mohamed G Gabr
*Assistant Examiner* — Khoa Tan Le

(57) ABSTRACT

An end effector drive mechanism has first and second pulleys and first and second jaws configured as a torque-amplifying tool assemblies. Each pulley jaw pair is configured as kinematic assembly having a compact footprint that can amplify outputs to increase the grip force applied by the jaws. The end effector drive mechanism is within a pulley envelope defined by the first and second pulleys. In certain configurations, the tool assemblies are configured to produce a grip force independent from a push-pull force that is exerted on (or by) the jaws. In certain configurations, the tool assemblies are configured to prevent undesirable reverse rotations and limit the range of travel of the jaws (or pulleys).

19 Claims, 39 Drawing Sheets

(58) Field of Classification Search
CPC .... A61B 2017/2934; A61B 2017/2936; A61B 2017/2939; A61B 2017/2943; A61B 2017/2944; A61B 2017/2947; A61B 2034/305; A61B 34/30; A61B 34/71
See application file for complete search history.

(56) References Cited

U.S. PATENT DOCUMENTS 5,318,589 A 6/1994 Lichtman
5,373,854 A 12/1994 Kolozsi
5,395,369 A 3/1995 McBrayer et al.
5,395,375 A 3/1995 Turkel et al.
5,396,900 A 3/1995 Slater et al.
5,476,479 A 12/1995 Green et al.
5,482,054 A 1/1996 Slater et al.
5,490,819 A 2/1996 Nicholas et al.
5,496,317 A 3/1996 Goble et al.
5,496,347 A 3/1996 Hashiguchi et al.
5,527,339 A 6/1996 Koscher et al.
5,575,805 A 11/1996 Li
5,582,617 A 12/1996 Klieman et al.
5,601,575 A 2/1997 Measamer et al.
5,722,935 A 3/1998 Christian
5,792,135 A 8/1998 Madhani et al.
5,792,165 A 8/1998 Klieman et al.
5,855,583 A 1/1999 Wang et al.
5,906,630 A 5/1999 Anderhub et al.
5,968,074 A 10/1999 Prestel
6,197,017 B1 3/2001 Brock et al.
6,206,903 B1 3/2001 Ramans
6,214,010 B1 4/2001 Farley et al.
6,273,860 B1 8/2001 Kostylev et al.
6,309,397 B1 10/2001 Julian et al.
6,331,181 B1 12/2001 Tierney et al.
6,368,290 B1 4/2002 Baska
6,371,952 B1 4/2002 Madhani et al.
6,371,956 B1 4/2002 Wilson et al.
6,394,998 B1 5/2002 Wallace et al.
6,491,691 B1 12/2002 Morley et al.
6,554,844 B2 4/2003 Lee et al.
6,623,482 B2 9/2003 Pendekanti et al.
6,644,532 B2 11/2003 Green et al.
6,663,641 B1 12/2003 Kovac et al.
6,685,698 B2 2/2004 Morley et al.
6,767,349 B2 7/2004 Ouchi
6,817,974 B2 11/2004 Cooper et al.
6,840,938 B1 1/2005 Morley et al.
6,843,793 B2 1/2005 Brock et al.
6,949,106 B2 9/2005 Brock et al.
6,964,662 B2 11/2005 Kidooka
6,969,385 B2 11/2005 Moreyra
6,991,627 B2 1/2006 Madhani et al.
6,994,708 B2 2/2006 Manzo
7,083,571 B2 8/2006 Wang et al.
7,090,683 B2 8/2006 Brock et al.
7,125,403 B2 10/2006 Julian et al.
7,147,650 B2 12/2006 Lee
7,169,141 B2 1/2007 Brock et al.
7,214,230 B2 5/2007 Brock et al.
7,316,681 B2 1/2008 Madhani et al.
7,338,513 B2 3/2008 Lee et al.
7,371,210 B2 5/2008 Brock et al.
7,608,083 B2 10/2009 Lee et al.
7,824,401 B2 11/2010 Manzo et al.
7,935,130 B2 5/2011 Williams
8,245,595 B2 8/2012 Milenkovic
8,479,969 B2 7/2013 Shelton, IV
8,540,748 B2 9/2013 Murphy et al.
8,551,115 B2 10/2013 Steger et al.
8,568,443 B1 10/2013 Jackman et al.
8,602,288 B2 12/2013 Shelton, IV et al.
8,758,392 B2 6/2014 Crainich
8,771,270 B2 7/2014 Burbank
8,800,838 B2 8/2014 Shelton, IV
9,028,494 B2 5/2015 Shelton, IV et al.
9,055,961 B2 6/2015 Manzo et al.
9,078,684 B2 7/2015 Williams
9,204,923 B2 12/2015 Manzo et al.
9,339,341 B2 5/2016 Cooper
9,358,031 B2 6/2016 Manzo
9,456,839 B2 10/2016 Cooper
9,554,790 B2 1/2017 Bailey et al.
9,615,846 B2 4/2017 Prestel
9,869,339 B2 1/2018 Zimmerman et al.
9,913,694 B2 3/2018 Brisson
9,918,731 B2 3/2018 Cooper et al.
10,130,366 B2 11/2018 Shelton, IV et al.
10,667,873 B2 6/2020 Wallace
11,020,112 B2 6/2021 Shelton, IV et al.
11,045,270 B2 6/2021 Shelton, IV et al.
2002/0111621 A1 8/2002 Wallace et al.
2004/0087940 A1 5/2004 Jahns et al.
2004/0260198 A1 12/2004 Rothberg et al.
2005/0187547 A1 8/2005 Sugi
2006/0074415 A1 4/2006 Scott et al.
2006/0184198 A1 8/2006 Bales et al.
2006/0190034 A1 8/2006 Nishizawa et al.
2007/0208375 A1 9/2007 Nishizawa et al.
2007/0246508 A1 10/2007 Green
2007/0255109 A1 11/2007 Stein et al.
2008/0046122 A1 2/2008 Manzo et al.
2008/0065102 A1 3/2008 Cooper
2008/0065105 A1 3/2008 Larkin et al.
2008/0125794 A1 5/2008 Brock et al.
2008/0167651 A1 7/2008 Tetzlaff et al.
2008/0196533 A1 8/2008 Bergamasco et al.
2008/0255421 A1 10/2008 Hegeman et al.
2009/0088774 A1 4/2009 Swarup et al.
2009/0110533 A1 4/2009 Jinno et al.
2009/0131975 A1 5/2009 Ahlberg et al.
2009/0198272 A1 8/2009 Kerver et al.
2009/0209960 A1 8/2009 Chojin
2009/0326530 A1 12/2009 Orban, III et al.
2010/0030238 A1 2/2010 Viola et al.
2010/0198218 A1 8/2010 Manzo
2011/0071543 A1 3/2011 Prisco et al.
2011/0276085 A1 11/2011 Krzyzanowski et al.
2011/0295269 A1 12/2011 Swensgard et al.
2011/0295270 A1 12/2011 Giordano et al.
2012/0116433 A1 5/2012 Houser et al.
2012/0232338 A1 9/2012 Livneh
2012/0289975 A1 11/2012 Martin et al.
2012/0330287 A1 12/2012 Yim
2013/0144395 A1 6/2013 Stefanchik et al.
2014/0005662 A1 1/2014 Shelton, IV
2014/0005678 A1 1/2014 Shelton, IV et al.
2014/0005708 A1 1/2014 Shelton, IV
2014/0073856 A1 3/2014 Stein et al.
2014/0100558 A1 4/2014 Schmitz et al.
2014/0243850 A1 8/2014 Sadaka
2014/0276956 A1 9/2014 Crainich et al.
2015/0150635 A1 6/2015 Kilroy et al.
2015/0157355 A1 6/2015 Price et al.
2015/0313676 A1 11/2015 Deodhar
2016/0000423 A1 1/2016 Shields et al.
2016/0051274 A1 2/2016 Howell et al.
2016/0143688 A1 5/2016 Orban, III et al.
2016/0175060 A1 6/2016 Park
2016/0287279 A1 10/2016 Bovay et al.
2016/0296219 A1 10/2016 Srivastava et al.
2016/0303743 A1* 10/2016 Rockrohr ............... A61B 34/30
2017/0165017 A1 6/2017 Chaplin et al.
2017/0252096 A1 9/2017 Felder et al.
2017/0333037 A1 11/2017 Wellman et al.
2018/0168572 A1 6/2018 Burbank
2018/0206904 A1 7/2018 Felder et al.
2019/0099227 A1 4/2019 Rockrohr
2019/0192137 A1 6/2019 Shelton, IV et al.
2019/0223960 A1 7/2019 Chaplin et al.
2019/0231374 A1 8/2019 Kimura et al.
2019/0374240 A1 12/2019 Brodbeck et al.
2019/0374297 A1* 12/2019 Wallace ................ A61B 34/30
2019/0380800 A1 12/2019 Jogasaki et al.
2020/0015807 A1 1/2020 Limon et al.

(56) References Cited

U.S. PATENT DOCUMENTS

| | | | |
|---|---|---|---|
| 2020/0022765 | A1 | 1/2020 | Limon et al. |
| 2020/0054405 | A1 | 2/2020 | Schuh et al. |
| 2020/0054408 | A1 | 2/2020 | Schuh et al. |
| 2020/0138531 | A1 | 5/2020 | Chaplin |
| 2020/0155136 | A1 | 5/2020 | Shuh et al. |
| 2020/0155253 | A1 | 5/2020 | Shuh et al. |
| 2021/0022819 | A1 | 1/2021 | Duque et al. |

FOREIGN PATENT DOCUMENTS

| | | | |
|---|---|---|---|
| EP | 2783643 | A1 | 10/2014 |
| JP | 2006061364 | A | 3/2006 |
| WO | WO-2011161626 | A2 | 12/2011 |
| WO | WO-2012068156 | A2 | 5/2012 |
| WO | WO-2014025204 | A1 | 2/2014 |
| WO | WO-2015088647 | A1 | 6/2015 |
| WO | WO-2016025132 | A1 | 2/2016 |
| WO | WO-2016045041 | A1 | 3/2016 |
| WO | WO-2016123139 | A2 | 8/2016 |
| WO | WO-2017064303 | A1 | 4/2017 |
| WO | WO-2017188851 | A1 | 11/2017 |
| WO | WO-2017189272 | A1 | 11/2017 |
| WO | WO-2018069679 | A1 | 4/2018 |
| WO | WO-2018123024 | A1 | 7/2018 |
| WO | WO-2018179140 | A1 | 10/2018 |
| WO | WO-2019199827 | A1 | 10/2019 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for EP Application No. EP21798886.4, mailed Dec. 3, 2024, 6 pages.

Extended European Search Report for Application No. EP26150767.7, mailed on Feb. 23, 2026, 9 pages.

Office Action for Chinese Application No. CN202180067481.6, mailed Jan. 21, 2026, 22 pages.

* cited by examiner

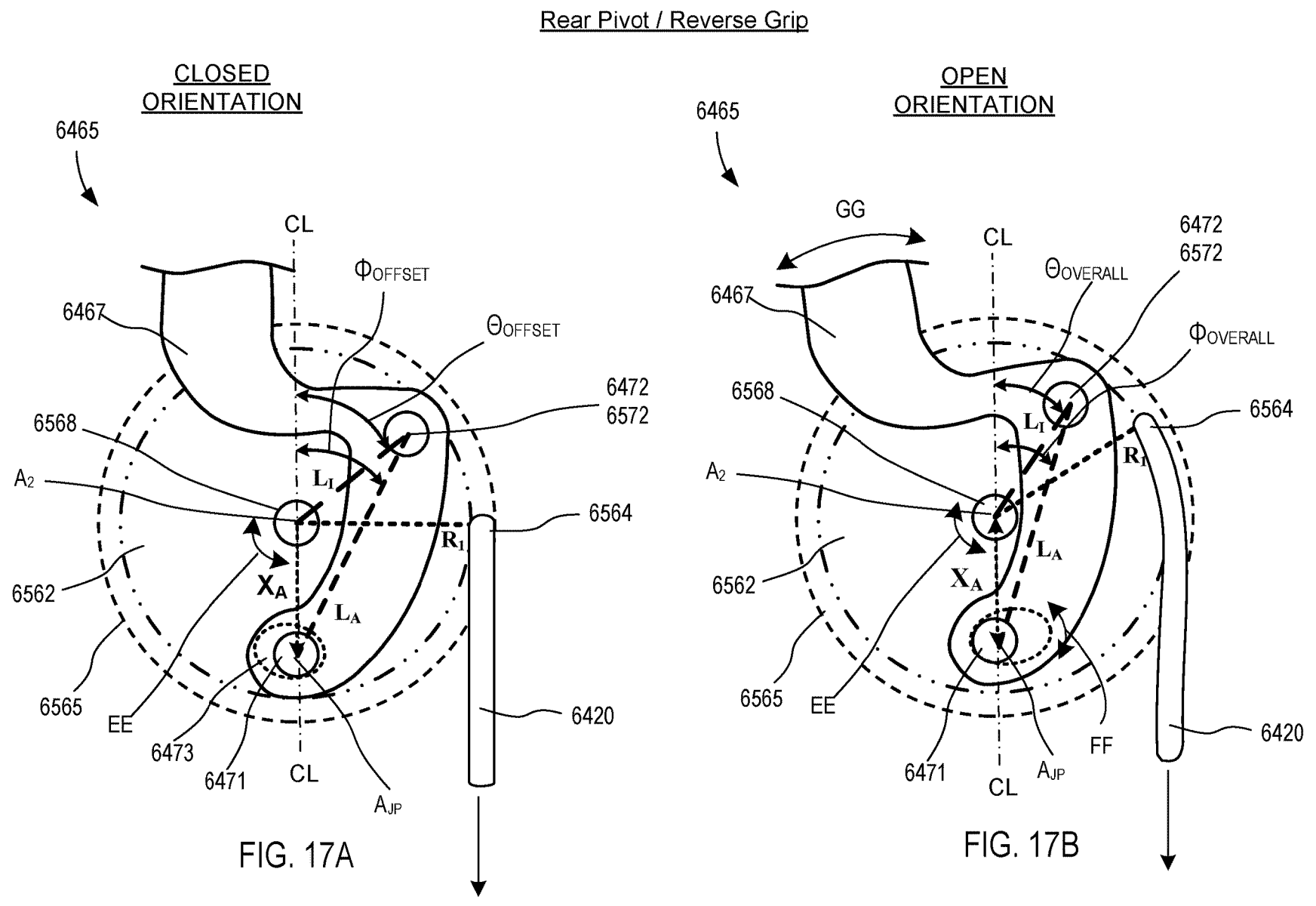

Rear Pivot / Reverse Grip

CLOSED ORIENTATION 6465 6467 6568 $A_2$ 6562 6565 EE 6473 6471 $A_{JP}$ $L_A$ $L_I$ $X_A$ $R_1$ CL $\Phi_{OFFSET}$ $\Theta_{OFFSET}$ 6472 6572 6564 6420

FIG. 17A

OPEN ORIENTATION 6465 6467 GG 6568 $A_2$ 6562 6565 EE 6471 $A_{JP}$ FF $L_A$ $L_I$ $X_A$ $R_1$ CL $\Theta_{OVERALL}$ $\Phi_{OVERALL}$ 6472 6572 6564 6420

MEDICAL DEVICES HAVING COMPACT END EFFECTOR DRIVE MECHANISMS WITH HIGH GRIP FORCE

CROSS-REFERENCE TO RELATED APPLICATIONS

This application is a U.S. national stage filing under 35 U.S.C. 371 of International Application No. PCT/US2021/053024 (filed Sep. 30, 2021), entitled "Medical Devices Having Compact End Effector Drive Mechanisms with High Grip Force," which claims priority to and the filing date benefit of U.S. Provisional Patent Application No. 63/086,662, entitled "Medical Devices Having Compact End Effector Drive Mechanisms with High Grip Force," filed Oct. 2, 2020, each of which is incorporated herein by reference in its entirety.

BACKGROUND

The embodiments described herein relate to grasping tools, more specifically to medical devices, and still more specifically to endoscopic tools. In particular, the embodiments described herein relate to medical devices having end effectors that are driven by compact multi-part drive mechanisms that can produce a high grip force while maintaining a compact form suitable for minimally invasive procedures.

Known techniques for Minimally Invasive Surgery (MIS) employ instruments to manipulate tissue that can be either manually controlled or controlled via computer-assisted teleoperation. Many known MIS instruments include a therapeutic or diagnostic end effector having one or more tool member components (e.g., forceps, cutting tool, or a cauterizing tool) mounted on an optional wrist mechanism at the distal end of an extension (also referred to herein as the main tube or shaft). During an MIS procedure, the end effector, wrist mechanism, and the distal end of the shaft can be inserted into a small incision or a natural orifice of a patient to position the end effector at a work site within the patient's body. The optional wrist mechanism can be used to change the end effector's orientation with respect to the shaft to perform the desired procedure at the work site. Known wrist mechanisms generally provide the desired degrees of freedom (DOFs) for movement of the end effector. For example, known wrist mechanisms are often able to change the pitch and yaw of the end effector with reference to the shaft. A wrist may optionally provide a roll DOF for the end effector, or the roll DOF may be implemented by rolling the shaft. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include tension members (e.g., cables or push/pull members) that extend through the shaft of the instrument and that connect the wrist mechanism to a mechanical structure configured to move the tension members to operate the wrist mechanism. For robotic or teleoperated systems, the mechanical structure is driven by an actuator (e.g., a motor) and can be operably coupled to a processing system to provide a user interface for a clinical user (e.g., a surgeon) to control the instrument.

Patients benefit from continual efforts to improve the effectiveness of MIS methods and tools. For example, reducing the size and/or the operating footprint of the shaft, wrist mechanism, and end effector can allow for smaller entry incisions and reduced need for space at the surgical site, thereby reducing the negative effects of surgery, such as pain, scarring, and undesirable healing time. But, producing small medical instruments that implement the clinically desired functions for minimally invasive procedures can be challenging. Specifically, simply reducing the size of known wrist mechanisms by "scaling down" the components will not result in an effective solution because required component and material properties do not scale. For example, efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys and/or contoured surfaces are generally needed to reduce cable friction, which extends instrument life and permits operation without excessive forces being applied to the cables or other structures in the wrist mechanism. Increased localized forces that may result from smaller structures (including the cables and other components of the wrist mechanism) can result in undesirable lengthening (e.g., "stretch" or "creep") of the cables during storage and use, reduced cable life, and the like.

Reducing the size of the wrist mechanism and end effector can also reduce the amount of force that can be exerted by the end effector during a procedure. For example, reducing the nominal size of the wrist mechanism can result in the end effector producing lower grip forces than that which can be produced by a larger wrist mechanism. Reduced grip forces can be undesirable in many applications. For example, reduced grip forces for a needle driver can result in the suture needle slipping within the end effector when higher external forces are encountered during a suturing operation. Many known end effectors include a pair of jaws that are rotatably connected to a wrist mechanism at a pivot axis. Such known jaws include an input pulley that is connected to a drive source (e.g., a cable drive connection) for receiving an input torque, which rotates the jaws to apply a grip force upon an object (e.g. a needle or tissue). Reducing the size of the wrist mechanism and end effector (including the input pulley), however, also reduces the amount of torque produced for a given amount of cable tension. Moreover, reducing the size of the wrist mechanism (including the input pulley) also results in the cables having smaller bend radii, which can reduce cable life. Cable tension is often reduced to accommodate the smaller bend radii. Thus, as noted above, increasing the cable tension to maintain the desired grip force can be undesirable.

Some known end effectors employ torque-amplifying drive mechanisms, which can produce increased grip forces without the need to proportionally increase cable tension. Known torque-amplifying end effector drive mechanisms generally include multiple kinematic linkages (e.g., additional pulleys or links coupling the input pulley to the jaws) through which the torque is amplified. For example, some known torque-amplifying drive mechanism include additional linkages to increase the moment arm upon which an input force (e.g., from a cable) is exerted, thereby increasing the output force. Accordingly, known torque-amplifying drive mechanisms generally require larger overall instrument diameters or jaw length to amplify drive torques as compared with non-amplified drive mechanisms. Thus, known torque-amplifying features are often incompatible with reduced-size MIS instruments.

Furthermore, because known torque-amplifying drive mechanisms include multiple kinematic links coupling the input pulley to the jaws, the motion of the jaws driven by such mechanisms can include both a rotational component and a translational component. For example, known end effectors often include two or more jaws that work together to perform intended clinical functions, such as a needle-driver tool that clamps a needle for suturing procedures. Such dual jaw end effectors are designed to move between an open configuration appropriate for loading a needle and a fully closed configuration for clamping the needle. Some known torque-amplifying drive mechanisms, however, will produce a linear motion of the jaws along with the rotational movement of the jaws as they move between the open configuration and the closed configuration. As a result, in certain circumstances, the grip force produced by torque-amplifying drive mechanisms can be affected by a linear "push-pull" force that is exerted on the jaws. The functional coupling of the push-pull force and the grip force can sometimes produce feedback that is not intuitive to the operator.

Thus, a need exists for improved, compact endoscopic tools having torque-amplifying, end effector drive mechanisms for driving end effectors to perform a wide variety of clinical functions while maintaining the desired overall tool size, DOF maneuverability, or other performance capabilities.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, an end effector drive mechanism has first and second pulleys and first and second jaws configured as a torque-amplifying tool assemblies (which function together as a tool drive mechanism). Each pulley jaw pair is configured as kinematic assembly having a compact footprint that can amplify outputs to increase the grip force applied by the jaws. In some embodiments, the end effector drive mechanism is within a pulley envelope defined by the first and second pulleys. In some embodiments, the tool assemblies are configured to produce a grip force independent from a push-pull force that is exerted on (or by) the jaws. In some embodiments, the tool assemblies are configured to prevent undesirable reverse rotations and limit the range of travel of the jaws (or pulleys).

In some embodiments, an apparatus includes a clevis, a central pin coupled to the clevis, a first tool assembly, a second tool assembly, and a jaw pivot pin. The first tool assembly is coupled to the clevis via the central pin and includes a first pulley and a first jaw. The first pulley includes a first input connector and a first output connector, and defines a first central opening and a first jaw pivot opening. The first input connector is coupled to a first tension member and the central pin extends through the first central opening. The first pulley rotates about the central pin when a first input torque is exerted by the first tension member. The first jaw includes a first pulley connector coupled to the first output connector. The first jaw rotates when a portion of the first input torque is transferred to the first jaw via an interface between the first pulley connector and the first output connector. The second tool assembly is coupled to the clevis via the central pin and includes a second pulley and a second jaw. The second pulley includes a second input connector and a second output connector, and defines a second central opening and a second jaw pivot opening. The second input connector is coupled to a second tension member and the central pin extends through the second central opening. The second pulley rotates about the central pin when a second input torque is exerted by the second tension member. The second jaw includes a second pulley connector coupled to the second output connector. The second jaw rotates when a portion of the second input torque is transferred to the second jaw via an interface between the second pulley connector and the second output connector. The jaw pivot pin couples the first jaw to the second jaw via a jaw pivot axis. The first jaw and the second jaw are configured to rotate relative to each other about the jaw pivot axis. The jaw pivot pin extends through the first jaw pivot opening of the first pulley and the second jaw pivot opening of the second pulley.

In some embodiments, the first jaw pivot opening and second jaw pivot opening are elongated. The jaw pivot pin is configured to translate relative to the central pin within the first jaw pivot opening and the second jaw pivot opening when at least one of the first pulley or the first jaw rotates relative to clevis.

In some embodiments, the first jaw pivot opening forms a first curvilinear path and second jaw pivot opening forms a second curvilinear path that is different from the first curvilinear path. The jaw pivot pin is configured to translate along a jaw pivot pin path defined by an intersection of the first curvilinear path and the second curvilinear path.

In some embodiments, the first pulley and the second pulley are between the first jaw and the second jaw. In some embodiments, the first jaw and the second jaw are between the first pulley and the second pulley.

In some embodiments, the central pin defines a central axis about which the pulley and the second pulley rotate. The first input connector is radially offset from the central axis by a first input radius. A first pulley envelope is defined as a cylindrical volume about the central axis having an envelope radius equal to the first input radius. The first output connector, the first jaw pivot opening, the first pulley connector, and the jaw pivot axis are within the first pulley envelope.

In some embodiments, the first pulley has a non-circular shape and defines a major radius and a minor radius. In some embodiments, the first input connector is offset from the central axis by the major radius.

In some embodiments, an apparatus includes a clevis, a central pin coupled to the clevis, a first tool assembly, a second tool assembly, and a jaw pivot pin. The first tool assembly is coupled to the clevis via the central pin and includes a first pulley and a first jaw. The first pulley includes a first input connector and a first output connector, and defines a first central opening. The first input connector is coupled to a first tension member and the central pin extends through the first central opening. The first pulley rotates about the central pin when a first input torque is exerted by the first tension member. The first jaw includes a first pulley connector coupled to the first output connector. The first jaw rotates when a portion of the first input torque is transferred to the first jaw via an interface between the first pulley connector and the first output connector. The second tool assembly is coupled to the clevis via the central pin and includes a second pulley and a second jaw. The second pulley includes a second input connector and a second output connector, and defines a second central opening. The second input connector is coupled to a second tension member and the central pin extends through the second central opening. The second pulley rotates about the central pin when a second input torque is exerted by the second tension member. The second jaw includes a second pulley connector coupled to the second output connector. The second jaw rotates when a portion of the second input torque is transferred to the second jaw via an interface between the second pulley connector and the second output connector. The first pulley and the second pulley are both between the first jaw and the second jaw. The jaw pivot pin couples the first jaw to the second jaw via a jaw pivot axis. The first jaw and the second jaw are configured to rotate relative to each other about the jaw pivot axis, which is offset from the central pin.

In some embodiments, an apparatus includes a clevis, a central pin coupled to the clevis and defining a central axis, a first tool assembly, a second tool assembly, and a jaw pivot pin. The first tool assembly is coupled to the clevis via the central pin and includes a first pulley and a first jaw. The first pulley includes a first input connector and a first output connector, and defines a first central opening. The first input connector is radially offset from the central axis by a first input radius and is coupled to a first tension member. The central pin extends through the first central opening. The first pulley rotates about the central pin when a first input torque is exerted by the first tension member. A first pulley envelope is defined as a cylindrical volume about the central axis having an envelope radius equal to the first input radius. The first jaw includes a first pulley connector coupled to the first output connector. The first jaw rotates when a portion of the first input torque is transferred to the first jaw via an interface between the first pulley connector and the first output connector. The second tool assembly is coupled to the clevis via the central pin and includes a second pulley and a second jaw. The second pulley includes a second input connector and a second output connector, and defines a second central opening. The second input connector is coupled to a second tension member and the central pin extends through the second central opening. The second pulley rotates about the central pin when a second input torque is exerted by the second tension member. The second jaw includes a second pulley connector coupled to the second output connector. The second jaw rotates when a portion of the second input torque is transferred to the second jaw via an interface between the second pulley connector and the second output connector. The jaw pivot pin couples the first jaw to the second jaw via a jaw pivot axis. The first jaw and the second jaw are configured to rotate relative to each other about the jaw pivot axis, which is offset from the central pin. The first output connector, the first pulley connector, and the jaw pivot axis are all within the first pulley envelope.

In some embodiments, an apparatus includes a clevis, a central pin coupled to the clevis and defining a central axis, a first tool assembly, a second tool assembly, and a jaw pivot pin. The first tool assembly is coupled to the clevis via the central pin and includes a first pulley and a first jaw. The first pulley includes a first input connector and a first output connector, and defines a first central opening. The first input connector is radially offset from the central axis by a first input radius and is coupled to a first tension member. The central pin extends through the first central opening. The first pulley rotates about the central pin when a first input torque is exerted by the first tension member. The first jaw includes a first pulley connector coupled to the first output connector. The first jaw rotates when a portion of the first input torque is transferred to the first jaw via an interface between the first pulley connector and the first output connector. The second tool assembly is coupled to the clevis via the central pin and includes a second pulley and a second jaw. The second pulley includes a second input connector and a second output connector, and defines a second central opening. The second input connector is coupled to a second tension member and the central pin extends through the second central opening. The second pulley rotates about the central pin when a second input torque is exerted by the second tension member. The second jaw includes a second pulley connector coupled to the second output connector. The second jaw rotates when a portion of the second input torque is transferred to the second jaw via an interface between the second pulley connector and the second output connector. The jaw pivot pin couples the first jaw to the second jaw via a jaw pivot axis. The first jaw and the second jaw are configured to rotate relative to each other about the jaw pivot axis, which is offset from the central axis by a jaw pivot offset distance that is less than the first input radius.

In some embodiments, an apparatus includes a clevis, a central pin coupled to the clevis and defining a central axis, a first tool assembly, a second tool assembly, and a jaw pivot pin. The first tool assembly is coupled to the clevis via the central pin and includes a first pulley and a first jaw. The first pulley includes a first input connector and a first output connector, and defines a first central opening. The first input connector is coupled to a first tension member. The central pin extends through the first central opening. The first pulley rotates about the central pin when a first input torque is exerted by the first tension member. The first output connector is radially offset from the central axis to define a first input link. The first jaw includes a first grip portion and a first pulley connector coupled to the first output connector. The first jaw rotates when a portion of the first input torque is transferred to the first jaw via an interface between the first pulley connector and the first output connector. The second tool assembly is coupled to the clevis via the central pin and includes a second pulley and a second jaw. The second pulley includes a second input connector and a second output connector, and defines a second central opening. The second input connector is coupled to a second tension member and the central pin extends through the second central opening. The second pulley rotates about the central pin when a second input torque is exerted by the second tension member. The second jaw includes a second grip portion and a second pulley connector coupled to the second output connector. The second jaw rotates when a portion of the second input torque is transferred to the second jaw via an interface between the second pulley connector and the second output connector. The jaw pivot pin couples the first jaw to the second jaw via a jaw pivot axis. The first jaw and the second jaw are configured to rotate relative to each other about the jaw pivot axis to move between an open configuration and a closed configuration. The first grip portion is in contact with the second grip portion when the first jaw and the second jaw are in the closed configuration. An end effector center line is defined between the central axis and the jaw pivot axis. The first input link and the end effector center line define an input link angle that increases when the first jaw and the second jaw move from the closed configuration towards the open configuration In some embodiments, the first input connector is radially offset from the central axis by a first input radius. A first pulley envelope is defined as a cylindrical volume about the central axis having an envelope radius equal to the first input radius. The first output connector, the first pulley connector, and the jaw pivot axis are within the first pulley envelope.

In some embodiments, the input link angle is less than ten degrees when the first jaw and the second jaw are in the closed configuration. In some embodiments, the input link angle is less than five degrees when the first jaw and the second jaw are in the closed configuration. In some embodiments, the first pulley connector of the first jaw is between the first grip portion and the jaw pivot pin. In some embodiments, the jaw pivot pin is between the first grip portion and the first pulley connector of the first jaw.

In some embodiments, an apparatus includes a clevis, a central pin coupled to the clevis, a first tool assembly, a second tool assembly, and a jaw pivot pin. The first tool assembly is coupled to the clevis via the central pin and includes a first rotatable member and a first jaw. The first rotatable member includes a first input connector and a first output connector, and defines a first central opening. The first input connector is coupled to a first tension member and the central pin extends through the first central opening. The first rotatable member rotates about the central pin when a first input torque is exerted by the first tension member. The first jaw includes a first rotatable member connector coupled to the first output connector. The first jaw rotates when a portion of the first input torque is transferred to the first jaw via an interface between the first rotatable member connector and the first output connector. The second tool assembly is coupled to the clevis via the central pin and includes a second rotatable member and a second jaw. The second rotatable member includes a second input connector and a second output connector, and defines a second central opening. The second input connector is coupled to a second tension member and the central pin extends through the second central opening. The second rotatable member rotates about the central pin when a second input torque is exerted by the second tension member. The second jaw includes a second rotatable member connector coupled to the second output connector. The second jaw rotates when a portion of the second input torque is transferred to the second jaw via an interface between the second rotatable member connector and the second output connector. The jaw pivot pin couples the first jaw to the second jaw via a jaw pivot axis. The first jaw and the second jaw are configured to rotate relative to each other about the jaw pivot axis, which is offset from the central pin.

In some embodiments, the first rotatable member and the second rotatable member can be any of a pulley, a link, or a gear. The first tension member and the second tension member can be any a cable, a band, or a push-pull rod.

In some embodiments, the first rotatable member defines a first jaw pivot opening and the second rotatable member defines a second jaw pivot opening. The jaw pivot pin extends through the first jaw pivot opening and the second jaw pivot opening. In some embodiments, the first rotatable member and the second rotatable member are between the first jaw and the second jaw.

In some embodiments, the first output connector includes an external gear and the first rotatable member connector includes an internal gear. A portion of the internal gear is meshed with a portion of the external gear at a mesh point to couple the first jaw to the first rotatable member. In some embodiments, the external gear is a sector gear and the internal gear is a curved rack.

In some embodiments, the first tool assembly and the second tool assembly form an end effector with an end effector center line being defined between the central pin and the jaw pivot axis. The end effector is configured to move between a plurality of open configurations and a closed configuration. The mesh point is radially offset from the central axis to define a first input link. The first input link and the end effector center line define an input link angle that remains substantially constant when the end effector moves from the closed configuration towards the open configuration.

In some embodiments, an apparatus includes a clevis, a central pin coupled to the clevis, a first jaw and second jaw. The first jaw is coupled to the clevis via the central pin and includes a grip portion and a pulley portion. The pulley portion of the first jaw includes first input connector coupled to a first tension member. The pulley portion of the first jaw has a non-circular shape and defines a first major radius and a first minor radius. The first input connector is offset from the central pin by the first major radius. The first jaw rotates when a portion of a first input force from the first tension member is transferred to the first jaw. The second jaw is coupled to the clevis via the central pin and includes a grip portion and a pulley portion. The pulley portion of the second jaw includes a second input connector coupled to a second tension member. The pulley portion of the second jaw has a non-circular shape and defines a first major radius and a first minor radius. The second input connector is offset from the central pin by the first major radius of the pulley portion of the second jaw. The second jaw rotates when a portion of a second input force from the second tension member is transferred to the second jaw.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIGS. 17A and 17B are side views of a tool assembly according to an embodiment having a rear pivot/reverse grip topology, shown in a first (closed) configuration (FIG. 17A) and a second (open) configuration (FIG. 17B).

DETAILED DESCRIPTION

Figure 1:
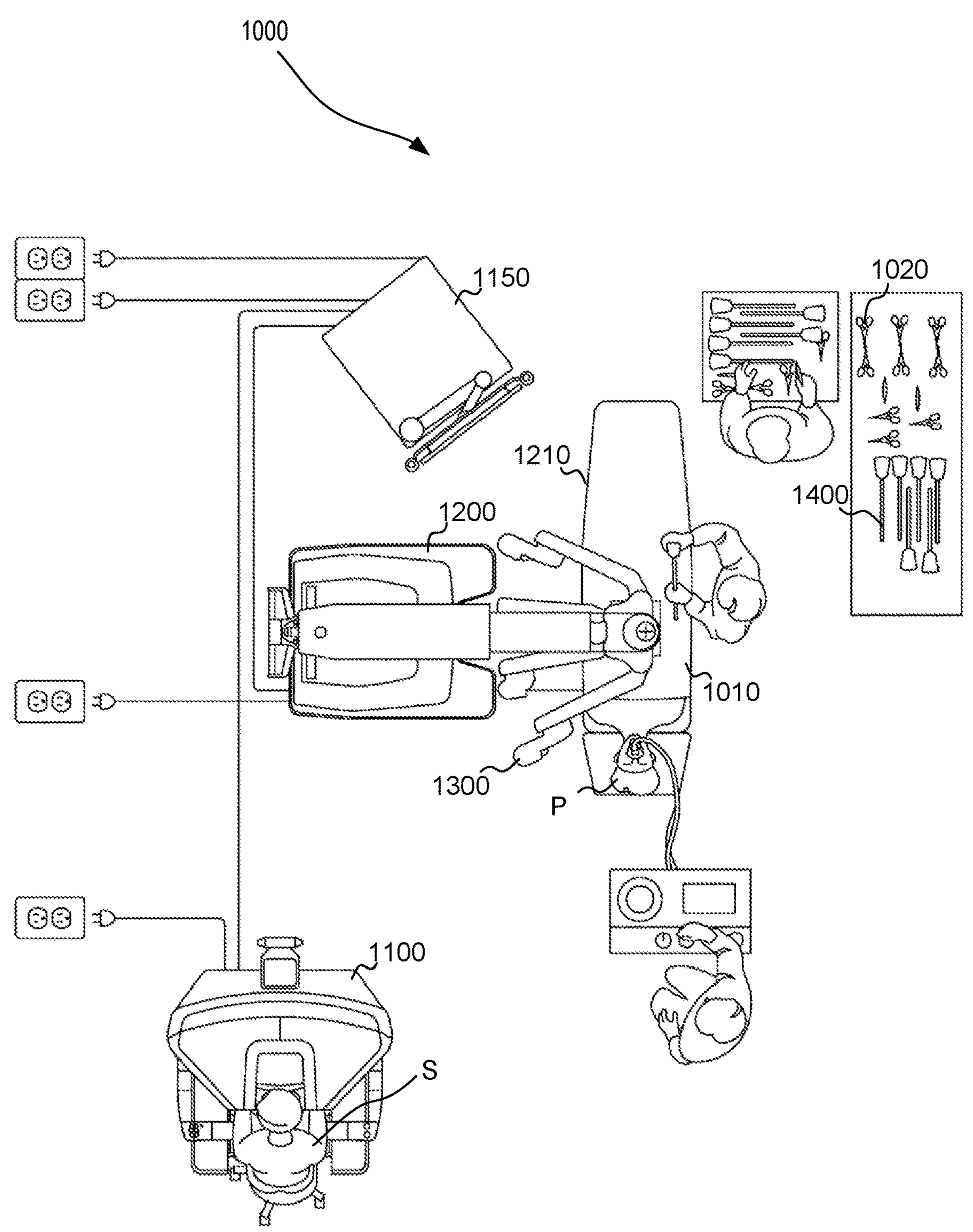
FIG. 1 is a plan view of a minimally invasive teleoperated medical system according to an embodiment, being used to perform a medical procedure such as surgery.

The embodiments described herein can advantageously be used in a wide variety of grasping, cutting, manipulating, and other driven tool member operations associated with minimally invasive surgery. Furthermore, instruments described herein can include end effector tool assemblies configured to amplify an input torque (or force) applied by a cable to produce a high grip force at the mating jaws of the tool assemblies. Specifically, each tool assembly includes a pulley jaw pair having a compact footprint that can produce amplified outputs to increase the grip force applied by the jaws. As shown herein, the mechanical advantage for amplifying an input torque is gained by separating the pivot joint about which the jaw rotates from the pivot point about which the pulley (to which the input torque is applied) rotates. Moreover, as described, the pivot joint of the jaw is within the geometric envelope of the pulley. In this manner, the tool assembly forms a first kinematic link that rotates about the first pivot point and that produces a first torque and a second kinematic link that rotates about the second pivot point and produces a second torque. This arrangement provides an amplified output force to an endpoint of a second kinematic link (i.e., the jaw) while maintaining a compact profile that is similar to that for a direct drive (i.e., non-amplified) jaw.

In some embodiments, the drive mechanism (including the kinematic links) for the pulley jaw pair is maintained within defined envelope to ensure that the desired functionality is maintained. For example, the drive mechanisms of the embodiments described herein can be maintained within an envelope similar in size (or of the same size) as a conventional, non-torque amplified end effector. In this manner, certain operations, such as articulation of the wrist along a pitch and a yaw axis, manipulating a suture needle to have a desired "throw distance," or the like can be maintained while the end effector also produces the desired high grip forces at the jaw grip portions. Additionally, by producing high grip forces with reduced cable tension, the embodiments described herein can improve cable life. Thus, the end effector drive mechanisms described herein can be configured as alternative or replacement drive mechanisms for corresponding known end effector drive mechanisms. In some embodiments, the end effector drive mechanism is within a pulley envelope defined by one or more of the pulleys of the jaw-pulley pairs. In some embodiments, the overall jaw length (e.g., the grip length from one of the pivot points) is maintained within a desired size range, e.g., a similar length as that for a non-torque amplified end-effector.

The tool assemblies described can be configured to have several different geometric arrangements of the kinematic links formed by the jaw-pulley pairs. The various geometric arrangements (referred to as "topologies") can produce certain desired functionality. Such different topologies can include variations in relative link lengths, the angular connections between links, and the relative location joints that interconnect links, as shown in the figures or described herein. The topologies described herein can produce desired performance by maintaining or controlling parameters such as an input disc angle (at which the input torque is applied to an input pulley), movement of arcuate slots within which a jaw pivot pin rests to control movement of the pair of jaws (i.e., when the pin reaches the end of the slots), or other features related to desired movements and ranges of motions of the drive mechanism, as described herein. For example, in some embodiments, a tool assembly can be configured to produce an amplified grip force that is independent from a push-pull force that is exerted on (or by) the jaws. In some embodiments, the tool assemblies are configured to prevent undesirable reverse rotations and limit the range of travel of the jaws (or pulleys). In some embodiments, a tool assembly can be configured to be self-locking when the linkages therein are moved beyond an over-center condition. When in a self-locked configuration, the tool members (e.g., jaws) do not require any input torque to maintain grip on the target object. In some embodiments, such a self-locking configuration can include an unlocking actuator to actively disengage the tool members thereby releasing them from the self-locked condition.

In some embodiments, a tool assembly can include a jaw-pulley pair having a jaw pivot axis that is separated from a pulley (or central) pivot axis, with the jaw pivot axis being further from the jaw tip than the central axis but still within the envelope of the pulley. Said another way, central pivot axis is between the jaw axis and the jaw tip. These embodiments are referred to as "rear pivot" topologies. In other embodiments, a tool assembly can include a jaw-pulley pair having a jaw pivot axis that is separated from a pulley (or central) pivot axis, with the central axis being further from the jaw tip than the jaw pivot axis. Said another way, jaw pivot axis is between the central pivot axis and the jaw tip but still within the envelope of the pulley. These embodiments are referred to as "front pivot" topologies.

In some embodiments, a tool assembly can be characterized as having a "forward grip" topology or a "reverse grip" topology, depending on whether certain link angles are increasing when the jaws move towards an open configuration (forward grip) or decreasing when the jaws move towards an open configuration (reverse grip). For example, in some embodiments, a tool assembly includes a jaw-pulley pair having a jaw pivot axis that is separated from a pulley (or central) pivot axis. The pulley is coupled to (and transmits force to) the jaw via an interface, such as a pin connector. In this manner, the tool assembly forms a first kinematic link that rotates about the first pivot point and that produces a first torque and a second kinematic link that rotates about the second pivot point and produces a second torque. The interface between the jaw and the pulley further forms an input link through which an input force is transferred to the jaw. The input link forms an input link angle with an end effector center line. When the pulley rotates to move the end effector from the closed configuration to an opened configuration, the input link angle changes. In forward grip topologies, the input link angle increases when the end effector moves from the closed configuration to the opened configuration. In some embodiments, a forward grip topology can produce an end effector in which the amplified grip force produced by the jaws is independent from a push-pull force that is exerted on (or by) the jaws. In reverse grip topologies, the input link angle decreases when the end effector moves from the closed configuration to the opened configuration.

In some embodiments, a tool assembly can include two jaw-pulley pairs having a jaw pivot axis that is separated from a pulley (or central) pivot axis. The rotation of the jaws relative to each is therefore along a different path than the rotation of the pulleys about the central pivot axis. In some embodiments, the pulleys can define slots within which a jaw pivot pin can translate when the jaws rotate relative to each other. Moreover, the ends of the slots can constrain the movement of the jaw pivot pin to provide travel limits at the grip open configuration to enhance the performance of the end effector. In some embodiments, a first pulley can define a first curvilinear path and a second pulley can define a second curvilinear path that is different from the first curvilinear path. The jaw pivot pin is configured to translate along a jaw pivot pin path defined by an intersection of the first curvilinear path and the second curvilinear path.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used herein, the term "target workspace" refers to anything within or pertaining to the endoscopic work cavity including the body of the patient, P, tissues and organs within the cavity, and tissue defining the cavity, and also to support structures for the MIS procedure including a cover and cannula supports, instruments and related attachments or medical implements including needles, suture materials, implants, meshes, etc. As used herein, the term "target tissue" refers to any tissue or organ that interacts with the target workspace including tissues and organs of the patient, P, natural tissues and organs introduced to the target workspace including natural transplant tissues and organs, artificial tissues and organs including mechanical or electromechanical organs, and tissue and organ assist devices such as pacemakers, mesh material, artificial skin and the like.

The term "flexible" in association with a part, such as a mechanical structure, component, or component assembly, should be broadly construed. In essence, the term means the part can be repeatedly bent and restored to an original shape without significant plastic deformation to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® surgical system, commercialized by Intuitive Surgical, Inc. of Sunnyvale, California. Examples of such surgical systems are the da Vinci Xi® surgical system (Model IS4000), da Vinci X® surgical system (Model IS4200), and the da Vinci Si® surgical system (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® surgical systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled instruments 1400 (also referred to herein as a "tool") through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
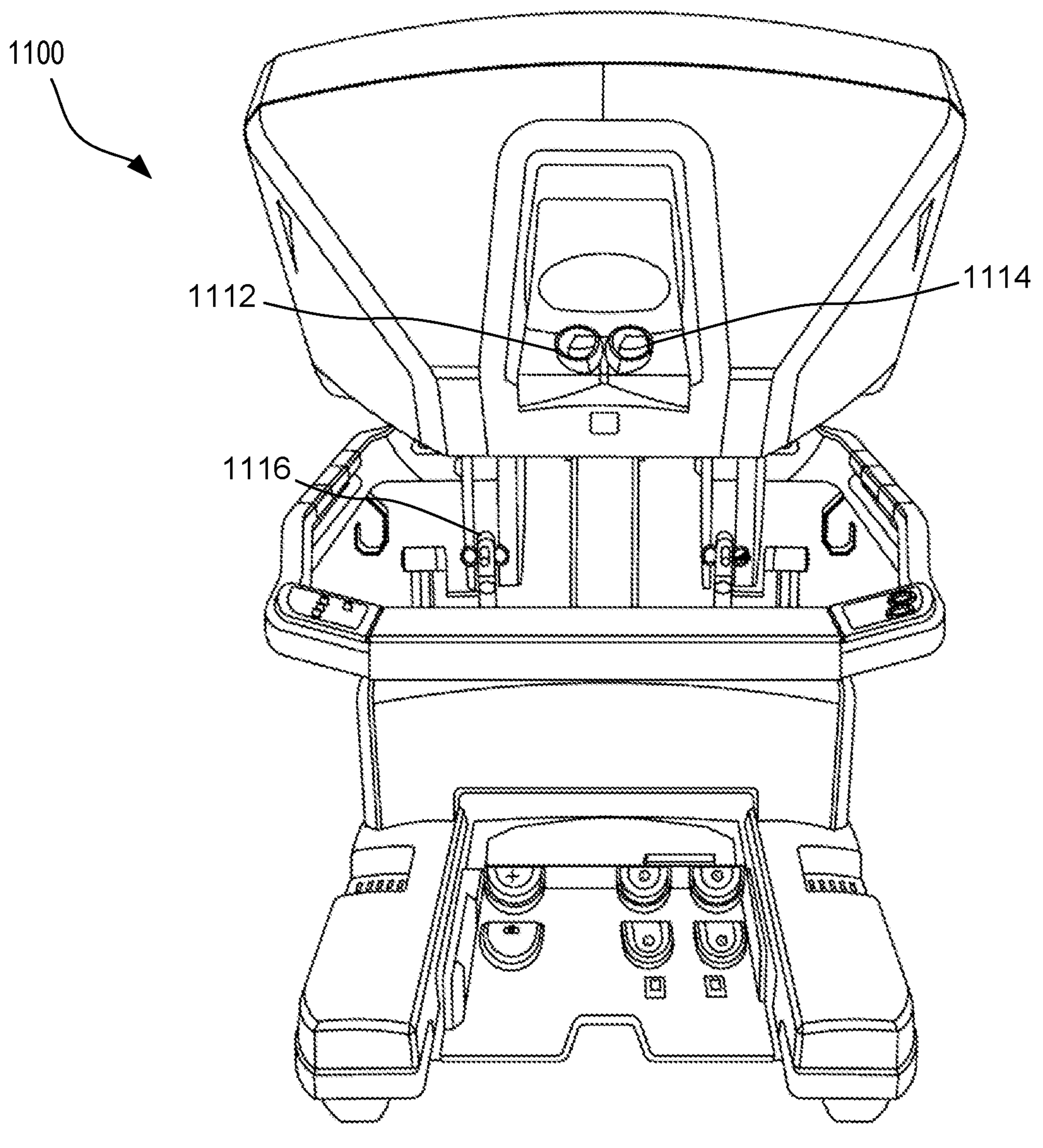
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
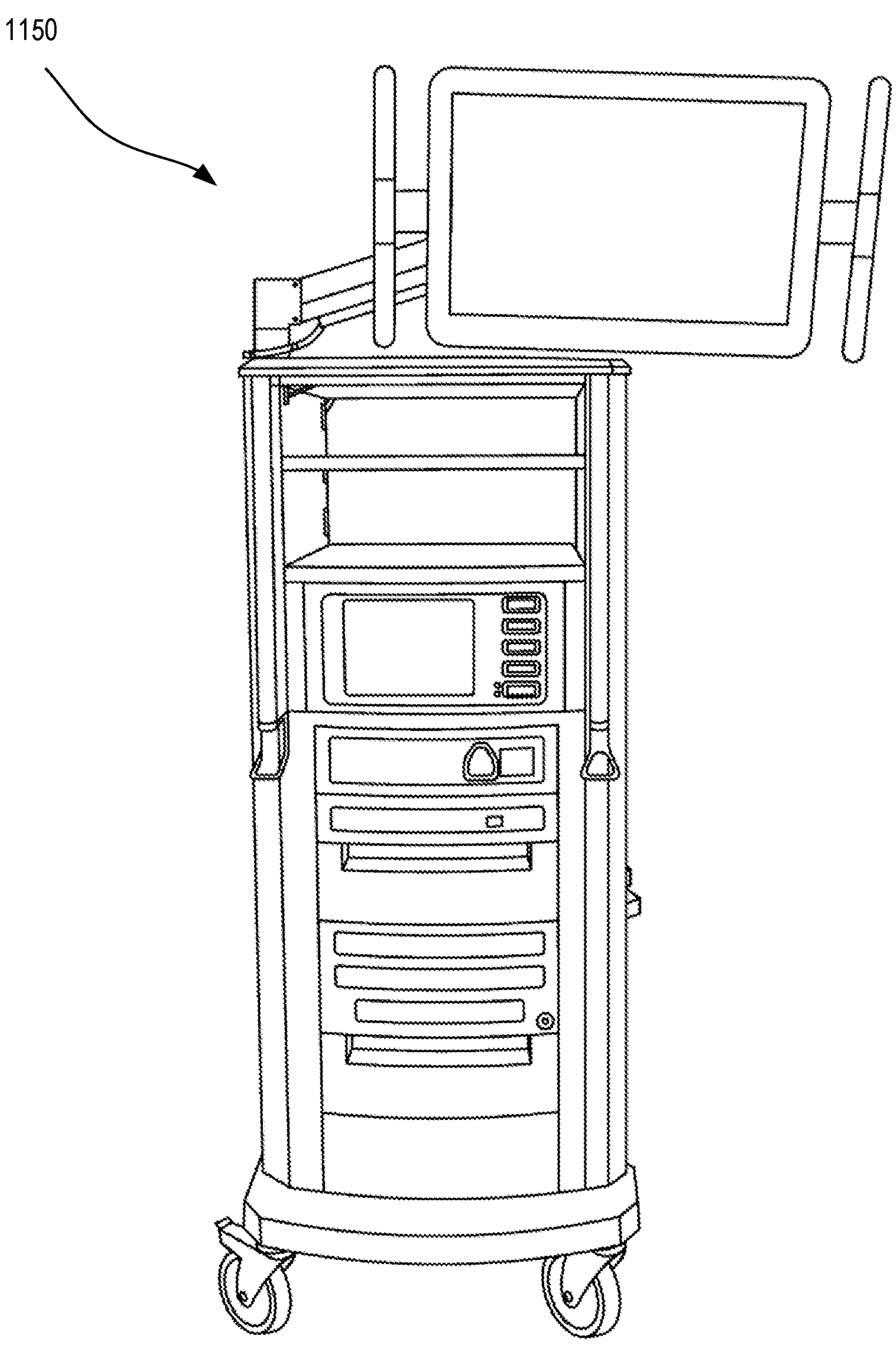
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
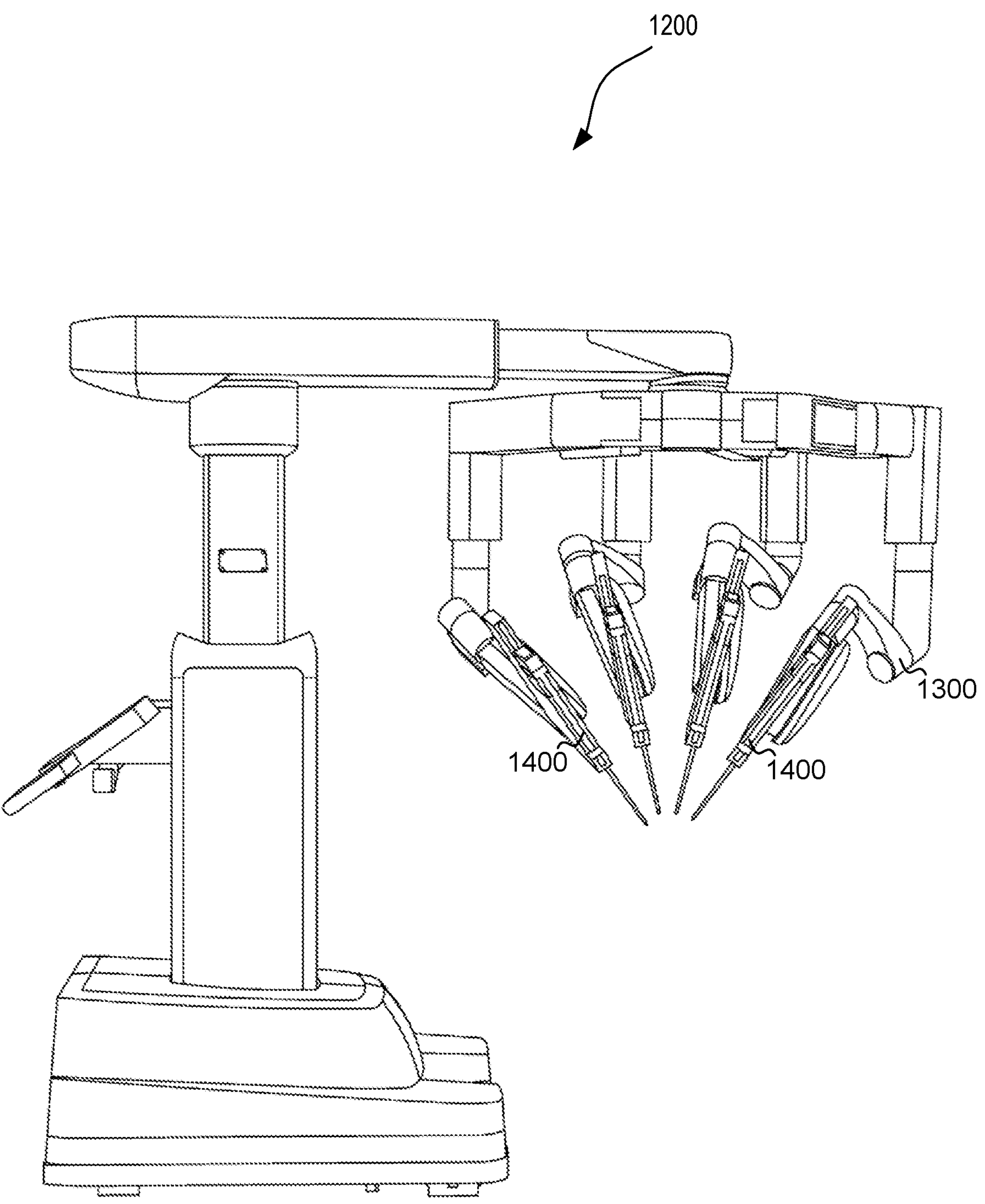
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a software and/or kinematic remote center of motion is maintained at the incision or orifice. In this manner, the incision size can be minimized.

FIGS. 5-8B are schematic illustration of a distal end portion of an instrument 2400, according to an embodiment. The instrument 2400, any of the other instruments described herein, or any of the components therein are optionally parts of a surgical system that performs minimally invasive surgical procedures and which can include a manipulator unit, a series of kinematic linkages, a series of cannulas, or the like. The instrument 2400 (and any of the instruments described herein) can be used in any suitable surgical system, such as the MIRS system 1000 shown and described above and can be configured to perform multiple clinical functions, including suturing, cutting, or grasping of tissue. The instrument 2400 includes a clevis 2610, an end effector 2460, a first tension member 2420 (which can be a cable, a rod, or any other suitable structure to actuate the end effector 2460), and a second tension member 2440 (which can be a cable, a rod, or any other suitable structure to actuate the end effector 2460). The instrument can include a shaft (not shown) that couples the clevis 2610 and end effector 2460 to a mechanical structure (not shown). The mechanical structure can be any of the mechanical structures shown and described herein, and can function to move each of the first tension member 2420 and the second tension member 2440 to actuate the end effector 2460. Specifically, the mechanical structure can function to apply a tension force on the first tension member 2420 and the second tension member 2440 to optionally produce rotation of the clevis 2610 within an optional wrist assembly (i.e., pitch rotation; the term pitch is arbitrary), to rotate the end effector 2460 relative to the clevis 2610 about the central axis $A_2$ (i.e., yaw rotation; the term yaw is arbitrary), to rotate the jaws of the end effector 2460 relative to each other (i.e., grip rotation), or any combination of these movements.

In some embodiments, the clevis 2610 is a portion of a wrist assembly, and is rotatably coupled to one or more additional links or devises to provide for rotation of the clevis 2610 about the instrument shaft (i.e., pitch rotation). In other embodiments, the clevis 2610 is coupled directly to the shaft and the instrument does not include a pitch rotation degree of freedom. The clevis includes a central pin 2683, which defines the central axis $A_2$ and to which the end effector 2460 is coupled. Although the central pin 2683 is shown as including two distinct segments each one of which is coupled to a portion (or side) of the end effector 2460, in other embodiments, the central pin 2683 can be a single structure that passes through the entire end effector.

Figure 5:
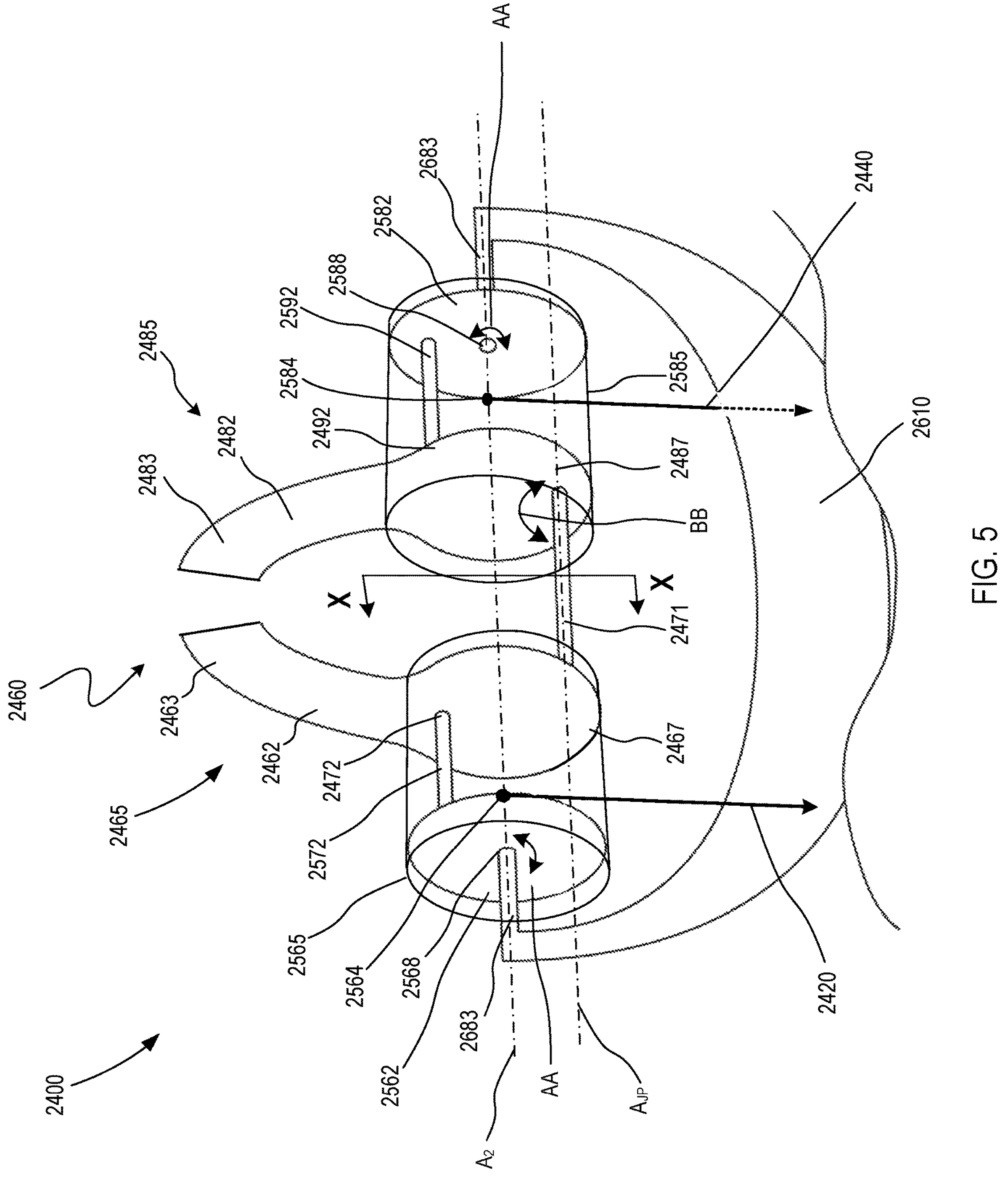
FIG. 5 is a diagrammatic perspective view of a portion of a medical instrument having two tool assemblies configured to amplify an input torque, according to an embodiment.
Figure 6:
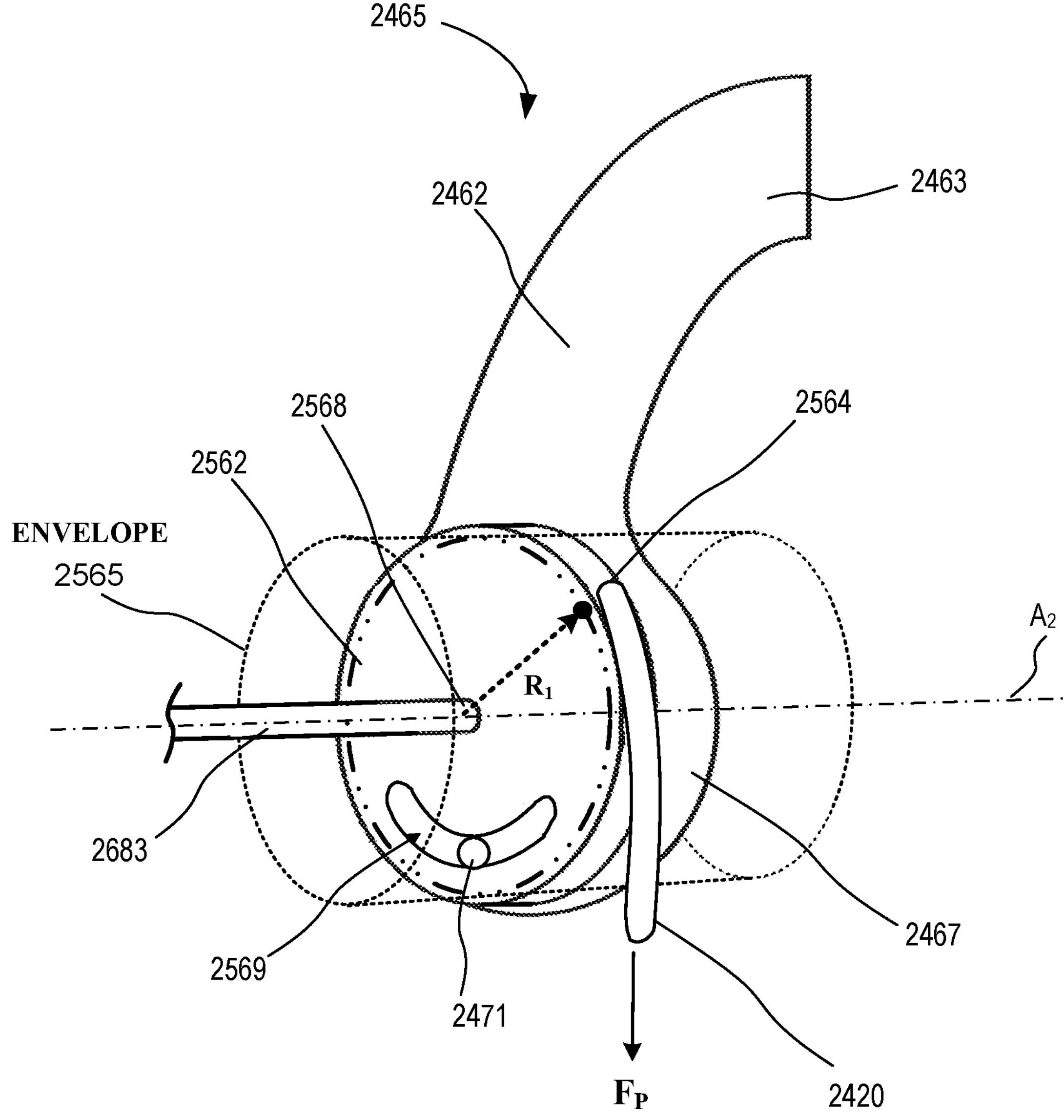
FIG. 6 is a diagrammatic perspective view of one of the tool assemblies of the medical instrument shown in FIG. 5, showing a pulley envelope.

The end effector 2460 includes a first tool assembly 2465 (which functions as a first jaw-rotatable member pair) and a second tool assembly 2485 (which functions as a second jaw-rotatable member pair). Although the first tool assembly 2465 and the second tool assembly 2485 are separate components that cooperatively function to form the end effector 2460, aspects of the first tool assembly 2465 described below (e.g., identification of kinematic links formed by the first tool assembly) are applicable to the second tool assembly 2485, and vice-versa. The first tool assembly 2465 includes a first jaw 2462 that is coupled to a first rotatable member 2562. The first rotatable member 2562 can be any suitable structure for operatively coupling the first jaw 2462 to the first tension member 2420, such as a link, a gear, or a pulley. In some embodiments, the first rotatable member 2562 is a disk-shaped member that is rotatably coupled to the clevis 2610 by the central pin 2683. Referring to FIGS. 5 and 6, the first rotatable member 2562 includes a first input connector 2564 and a first output connector 2572, and defines a central opening 2568. The central pin 2683 is coupled within the central opening 2568 to allow the first rotatable member 2562 to rotate relative to the clevis 2610 about the central axis $A_2$, as shown by the arrow AA. The first tension member 2420 is coupled to the first rotatable member 2562 at the first input connector 2564. The first input connector 2564 can be any suitable connector or mechanism for securing the first tension member 2420 to the first rotatable member 2562. For example, in some embodiments, the first input connector 2564 can be an opening within which a cable crimp is securely fastened. In other embodiments, the first input connector 2564 can be a protrusion about which the first tension member 2420 is securely wrapped. In yet other embodiments, the first input connector 2564 can be a pivot joint (e.g., a ball or socket) for allowing a push-pull rod to be coupled to the first rotatable member 2562. Referring to FIG. 6, the first tension member 2420 is coupled to the first rotatable member 2562 at a first input radius $R_1$ from the central axis $A_2$. Thus, when an input force $F_P$ is applied by the first tension member 2420 onto the first rotatable member 2562, an input torque is produced about the central axis $A_2$ to rotate the first rotatable member 2562. Additionally, the first rotatable member 2562 defines a first envelope 2565 as the swept volume about the central axis $A_2$ that has an envelope radius equal to the outer-most distance (e.g., radius) of the first rotatable member 2562. In some embodiments, the first envelope 2565 has an envelope radius equal to the first input radius $R_1$.

Figure 7:
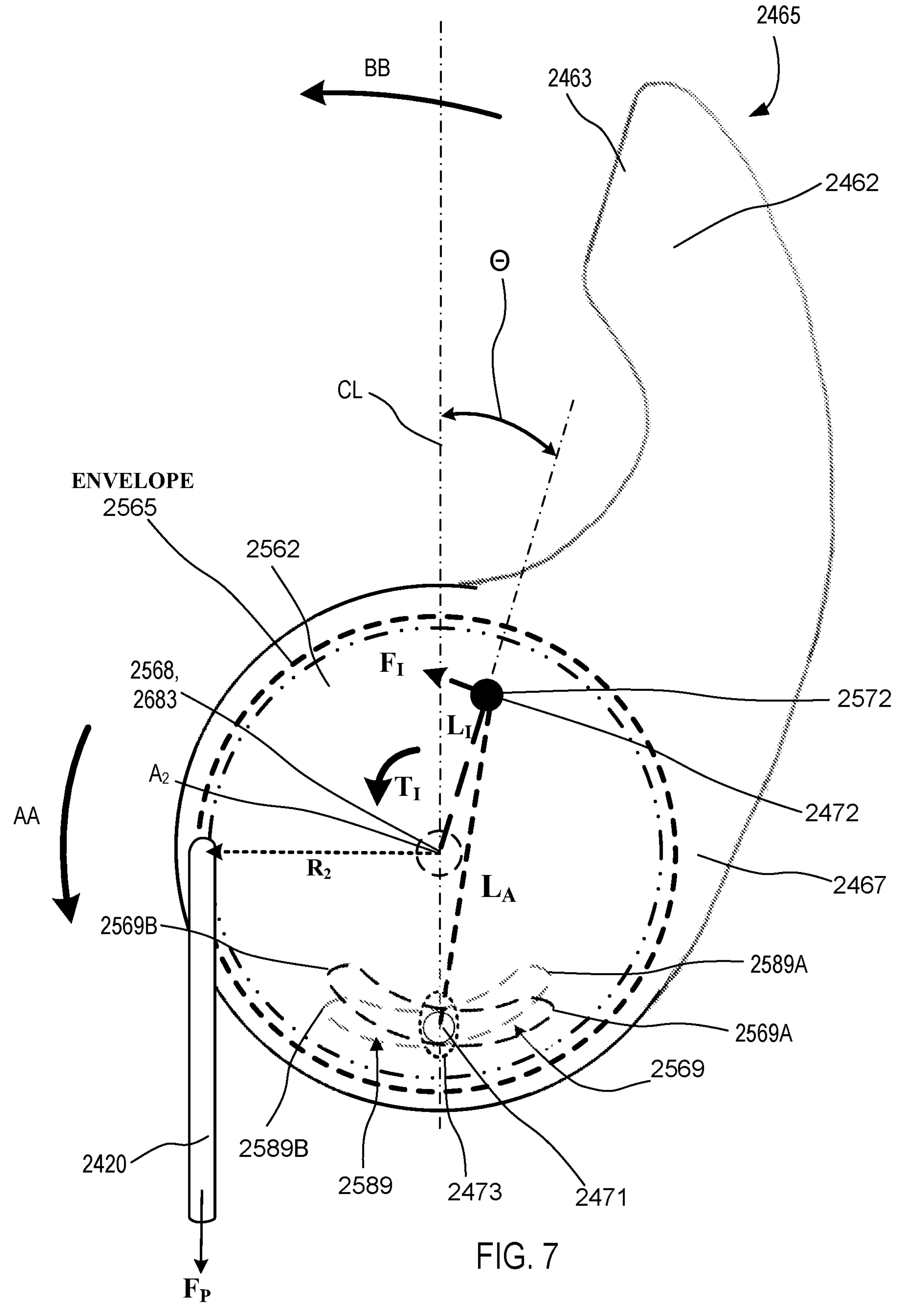
FIGS. 7, 8A, and 8B are side views of the medical instrument shown in FIG. 5 taken along line X-X to show one of the tool assemblies in a first (partially opened) configuration (FIG. 7), and a second (closed) configuration (FIG. 8A), and a third (fully opened) configuration (FIG. 8B).

The first output connector 2572 can be any suitable connector or mechanism that couples the first jaw 2462 to the first rotatable member 2562. Moreover, the first output connector 2572 is matingly coupled to a first connector 2472 of the first jaw 2462 to transfer forces from the first rotatable member 2562 to the first jaw 2462. In some embodiments, the first output connector 2572 can be a protrusion that is received within a corresponding opening of the first jaw 2462. In other embodiments, the first output connector 2572 can be an opening within which a protrusion from the first jaw 2462 is received. Referring to FIG. 7, which shows the geometric layout of the first tool assembly 2465, the first output connector 2572 is radially offset from the central axis $A_2$ by a jaw input length, identified as $L_1$. Thus, the coupling between the first pulley 2562 and the first jaw 2462 defines a kinematic link identified as $L_1$ that rotates about the central axis $A_2$. As shown, the first output connector 2572 and the kinematic link $L_1$ are within the first pulley envelope 2565. Similarly stated, the jaw input length $L_1$ is less than or equal to the first input radius $R_1$.

The first jaw 2462 includes a distal portion 2463 and a proximal portion 2467. The distal portion 2463 functions as a grip portion to cooperate with the second jaw 2482 to contact tissue, grasp a needle, or perform other operations. The proximal portion 2467 includes the first connector 2472, which couples the first jaw 2462 to and transfers forces from the first rotatable member 2562. The first jaw 2462 is rotatably coupled to the second jaw 2482 by a jaw pivot pin 2471, which defines a jaw pivot axis $A_{JP}$. Thus, when the torque applied to the first rotatable member 2562 by the first tension member 2420 is transferred to the first jaw 2462, the first jaw 2462 rotates relative to the second jaw 2482 (and in certain situations, also the clevis 2610) about the jaw pivot axis $A_{JP}$, as shown by the arrow BB. Referring again to FIG. 7, the jaw pivot axis $A_{JP}$ is offset from the central axis $A_2$ along an end effector center line CL. The jaw pivot axis $A_{JP}$ is also offset from the first connector 2472 by a jaw applied length, identified as $L_A$. Thus, the coupling of the jaws at the jaw pivot pin 2471 and the coupling of the first jaw 2462 and the first rotatable member 2562 at the first connector 2472 defines a kinematic link identified as $L_A$ that rotates about the jaw pivot axis $A_{JP}$. As shown, the jaw pivot axis $A_{JP}$ and the kinematic link $L_A$ are within the first envelope 2565. Although FIG. 7 shows the geometric layout of the first tool assembly 2465, this layout (e.g., the jaw input length $L_1$ and the jaw applied length $L_A$) is also applicable to the second tool assembly 2485.

The second tool assembly 2485 includes a second jaw 2482 that is coupled to a second rotatable member 2582. The second rotatable member 2582 can be any suitable structure for operatively coupling the second jaw 2482 to the second tension member 2440, such as a link, a gear, or a pulley. In some embodiments, the second rotatable member 2582 is a disk-shaped member that is rotatably coupled to the clevis 2610 by the central pin 2683. The second rotatable member 2582 includes a second input connector 2584 and a second output connector 2592, and defines a central opening 2588. The central pin 2683 is coupled within the central opening 2588 to allow the second rotatable member 2582 to rotate relative to the clevis 2610 about the central axis $A_2$, as shown by the arrow AA. The second tension member 2440 is coupled to the second rotatable member 2582 at the second input connector 2584. The second input connector 2584 can be any suitable connector or mechanism for securing the second tension member 2440 to the second rotatable member 2582. For example, in some embodiments, the second input connector 2584 can be an opening within which a cable crimp is securely fastened. In other embodiments, the second input connector 2584 can be a protrusion about which the second tension member 2440 (e.g., a cable) is securely wrapped. In yet other embodiments, the second input connector 2584 can be a pivot joint (e.g., a ball or socket) for allowing a push-pull rod to be coupled to the second rotatable member 2582. Referring to FIG. 7, the second tension member 2440 is coupled to the second rotatable member 2582 at a second input radius $R_2$ from the central axis $A_2$. Thus, when an input force $F_P$ is applied by the second tension member 2440 onto the second rotatable member 2582, an input torque is produced about the central axis $A_2$ to rotate the second rotatable member 2582. Additionally, the second rotatable member 2582 defines a second envelope 2585 as the swept volume about the central axis $A_2$ that has an envelope size (e.g., radius) equal to the outer-most size (e.g., radius) of the second rotatable member 2582. In some embodiments, the second envelope 2585 has an envelope radius equal to the second input radius $R_2$. In some embodiments, the second input radius $R_2$ is equal to the first input radius $R_1$ and the second envelope 2585 is the same as the first envelope 2565.

The second output connector 2592 can be any suitable connector or mechanism that couples the second jaw 2482 to the second rotatable member 2582. Moreover, the second output connector 2592 is matingly coupled to a second connector 2492 of the second jaw 2482 to transfer forces from the second rotatable member 2582 to the second jaw 2482. In some embodiments, the second output connector 2592 can be a protrusion that is received within a corresponding opening of the second jaw 2482. In other embodiments, the second output connector 2592 can be an opening within which a protrusion from the second jaw 2482 is received. Referring to FIG. 7, which also applies to the second tool assembly, the second output connector 2592 is radially offset from the central axis $A_2$ by a jaw input length, identified as $L_1$. Thus, the coupling between the second rotatable member 2582 and the second jaw 2482 defines a kinematic link identified as $L_1$ that rotates about the central axis $A_2$. The second output connector 2592 and the kinematic link $L_1$ are within the second envelope 2585.

The second jaw 2482 includes a distal portion 2483 and a proximal portion 2487. The distal portion 2483 functions as a grip portion to cooperate with the first jaw 2462 to contact tissue, grasp a needle, or perform other operations. The proximal portion 2487 includes the second connector 2492, which couples the second jaw 2482 to and transfers forces from the second rotatable member 2582. The first jaw 2462 is rotatably coupled to the second jaw 2482 by the jaw pivot pin 2471. Thus, when the torque applied to the second rotatable member 2582 by the second tension member 2440 is transferred to the second jaw 2482, the second jaw 2482 rotates relative to the first jaw 2462 (and also the clevis 2610) about the jaw pivot axis $A_{JP}$, as shown by the arrow BB. The jaw pivot axis $A_{JP}$ is offset from the second connector 2492 by a jaw applied length, identified as $L_A$. Thus, the coupling of the jaws at the jaw pivot pin 2471 and the coupling of the second jaw 2482 and the second rotatable member 2582 at the second connector 2492 defines a kinematic link identified as $L_A$ that rotates about the jaw pivot axis $A_{JP}$. As shown, the jaw pivot axis $A_{JP}$ and the kinematic link $L_A$ are within the second envelope 2585.

Although the instrument 2400 is shown as having the first jaw 2462 and the second jaw 2482 between the first rotatable member 2562 and the second rotatable member 2582, in other embodiments, the instrument 2400 (or any of the instruments shown herein) can be configured as having the first rotatable member 2562 and the second rotatable member 2582 between the first jaw 2462 and the second jaw 2482. In such embodiments, the jaw pivot pin 2471 extends through the first rotatable member 2562 and the second rotatable member 2582. Thus, in some embodiments, the first rotatable member 2562 optionally defines a jaw pivot opening 2569 and the second rotatable member 2582 optionally defines a jaw pivot opening 2589 to allow for passage of the jaw pivot pin 2471. Embodiments including the optional jaw pivot openings are shown in FIGS. 6-8B. As shown, the jaw pivot pin 2471 extends through the first jaw pivot opening 2569 and the second jaw pivot opening 2589. More particularly, the first jaw pivot opening 2569 and the second jaw pivot opening 2589 are each elongated to allow movement of the jaw pivot pin 2471 relative to the first rotatable member 2562 and the second rotatable member 2582 during operation. The first jaw pivot opening 2569 includes a first end 2569A and a second end 2569B and the second jaw pivot opening 2589 includes a first end 2589A and a second end 2589B. In certain instances, the wall defining the first jaw pivot opening 2569 and the wall defining the second jaw pivot opening 2589 can constrain the movement of the jaw pivot pin 2471 during operation. Said another away, the shape, size, or both the shape and size of the first jaw pivot opening 2569 and the second jaw pivot opening 2589 can limit the movement of the jaw pivot pin 2471 during use. Although the first jaw pivot opening 2569 and the second jaw pivot opening 2589 are shown as being curved (to define a curvilinear path), in other embodiments, either or both of the first jaw pivot opening 2569 and the second jaw pivot opening 2589 can be linear elongated slots. In yet other embodiments, either or both of the first jaw pivot opening 2569 and the second jaw pivot opening 2589 can have a curved section and a linear section. The size and shape of the jaw pivot openings can be selected to minimize the amount of material removed from the rotatable members (e.g., to preserve the structural stability of the rotatable members) while allowing for the desired movement of the jaw pivot pin 2471 therein. In some embodiments, the shape of the jaw pivot openings can be curvilinear because the rotation of $L_1$ will move the location of the jaw pivot pin 2471 closer or further away from the central pin 2683 as the movable members rotate. In some embodiments, the path of the jaw pivot pin 2471 can be spiral.

Although the movable members are shown and described as including the jaw pivot openings 2569, 2589 because the instrument 2400 is configured as having the first jaw 2462 and the second jaw 2482 between the first rotatable member 2562 and the second rotatable member 2582, in other embodiments, the first rotatable member 2562 need not include the first jaw pivot opening 2569 and the second rotatable member 2582 need not include the second jaw pivot opening 2589 (see, e.g. FIG. 5).

As shown, the first tool assembly 2465 and the second tool assembly 2485 have a rear pivot topology. Specifically, the jaw pivot axis $A_{JP}$ is offset from the central axis $A_2$ along an end effector center line CL (see FIG. 7), with the jaw pivot axis being further from the jaw tip than the central axis $A_2$. Said another way, the central axis $A_2$ is between the jaw pivot axis $A_{JP}$ and the distal end (or grip portions) 2463, 2483 of the jaws 2462, 2482. Additionally, the first tool assembly 2465 and the second tool assembly 2485 have a forward grip topology. Referring to FIG. 7, the end effector center line CL is defined between (and normal to) the central axis $A_2$ and the jaw pivot axis $A_{JP}$. The input link $L_1$ rotates about the central axis $A_2$ when the input force $F_P$ is applied to the rotatable members. Thus, the input link $L_1$ and the end effector center line CL form an input link angle Θ. When the rotatable members rotate to move the end effector 2460 from the closed configuration (FIG. 8A) to an opened configuration (FIGS. 7, 8B), the input link angle Θ increases. In other embodiments, an end effector can have a reverse grip topology (where the input link angle decreases when the end effector moves from the closed configuration to an opened configuration (FIG. 7).

In use, the end effector 2460 can amplify the input force $F_P$ to produce a higher grip force produced by the jaws 2462, 2482 than would be produced with a standard single-piece jaw and pulley system. As described below, the end effector 2460 (and each of the tool assemblies 2465, 2485) includes additional kinematic linkages to increase the moment arm upon which the input force $F_P$ is exerted, thereby increasing the output grip force. A general description of the force amplification is described below with reference to FIGS. 7 and 8, which show the geometric layout of first tool assembly 2465, but which is also applicable to the second tool assembly 2485. Additionally, the free-body diagrams and grip force equations discussed below (e.g., with reference to the end effector 4460) are also applicable to the end effector 2460.

As shown, the input force $F_P$ is applied to the input connector of the first rotatable member 2562. The input force $F_P$ acts through the second input radius $R_2$ to produce an input torque $T_1$ about the central axis $A_2$, in the direction shown by the arrow AA. The input torque $T_1$ is applied throughout the first rotatable member 2562 within the rotation plane of the first rotatable member 2562 such that a resultant input force $F_1$ is produced at the interface of the output connector 2572 (of the first rotatable member) and the first connector 2472 (of the first jaw 2462). In this manner, the input force $F_1$ acts upon the first jaw 2462. Specifically, when the first rotatable member 2562 rotates about the central axis $A_2$ (arrow AA), the input force $F_1$ causes the first jaw 2462 to rotate about the jaw pivot pin 2471 (which defines the jaw pivot axis $A_{JP}$), as shown by the arrow BB. The magnitude of the input force $F_1$ is based on the length of the input link $L_1$ and the resulting input force $F_1$ is proportional to the input force $F_P$ by the ratio of the lengths ($R_2/L_1$). Similarly, the kinematic link $L_A$ (i.e., the jaw applied length) acts as a torque moment arm for the input force $F_1$ that is transferred via the interface of the first output connector 2572 (of the first rotatable member) and the first connector 2472 to drive rotation of the first jaw 2462. The component of the input force $F_1$ that is normal to the kinematic link $L_A$ produces an applied torque on the first jaw 2462 that is proportional to the length $L_A$. Because the length of the kinematic link $L_A$ is longer than the length of the input link, $L_1$ (due to the first output connector 2572 and the first connector 2472 being offset from the jaw pivot pin 2471) tool assembly 2465 provides an amplified drive torque to the first jaw 2462 to drive its rotation. Similarly stated, by spacing the interface of the first output connector 2572 and the first connector 2472 on one side of central pin 2683 and apart from the jaw pivot pin 2471 located the other side of the central pin 2583, mechanical advantage can be gained via the pulley-jaw pair. More specifically, because the distance from the output connector 2572 to the jaw pivot pin 2471 is greater, the torque output is amplified generally by the ratio of distances $L_A$ and $L_1$. Thus, by maximizing this ratio, the amount of amplification can be increased.

Figure 8A:
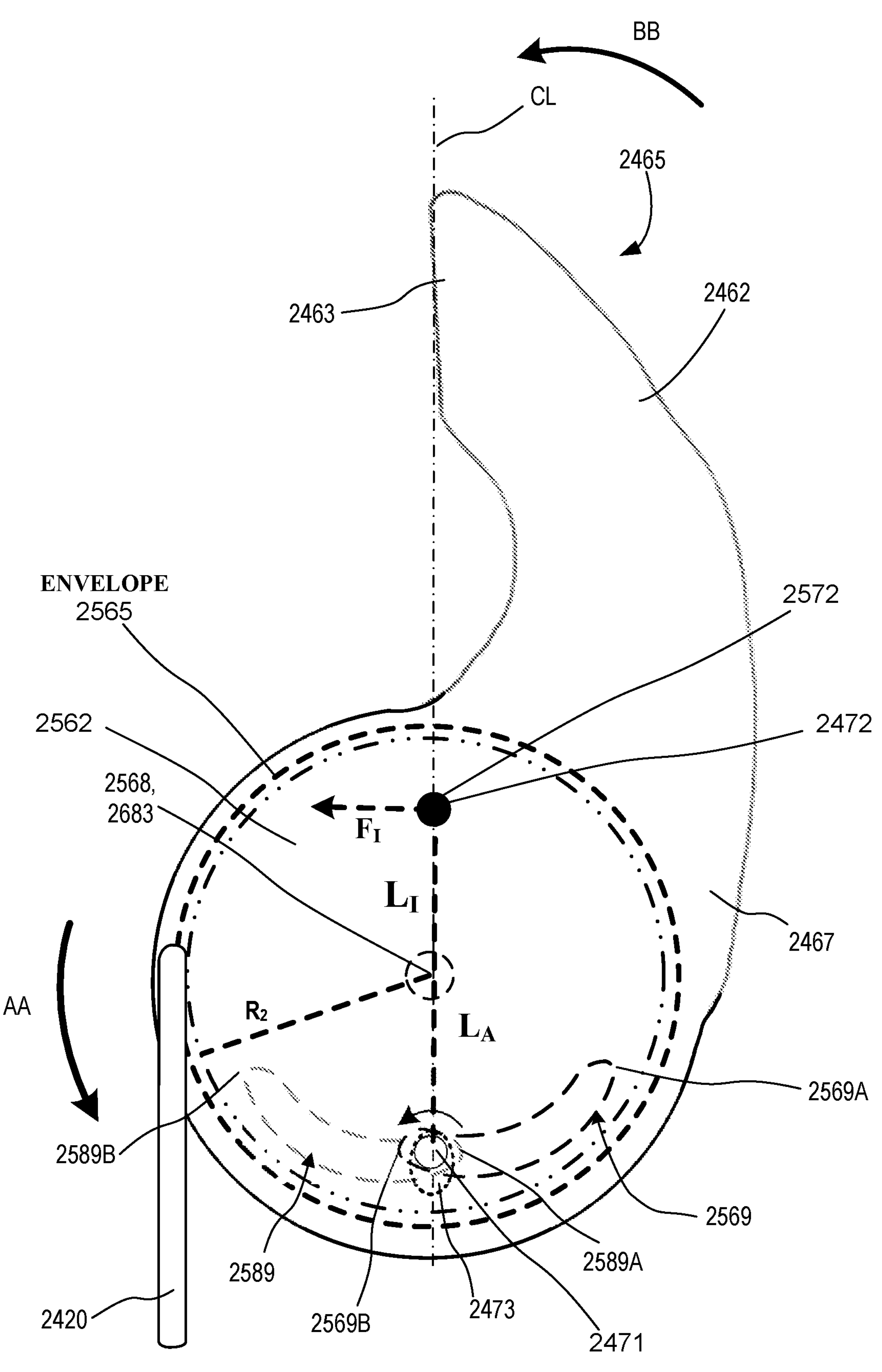
Figure 8B:
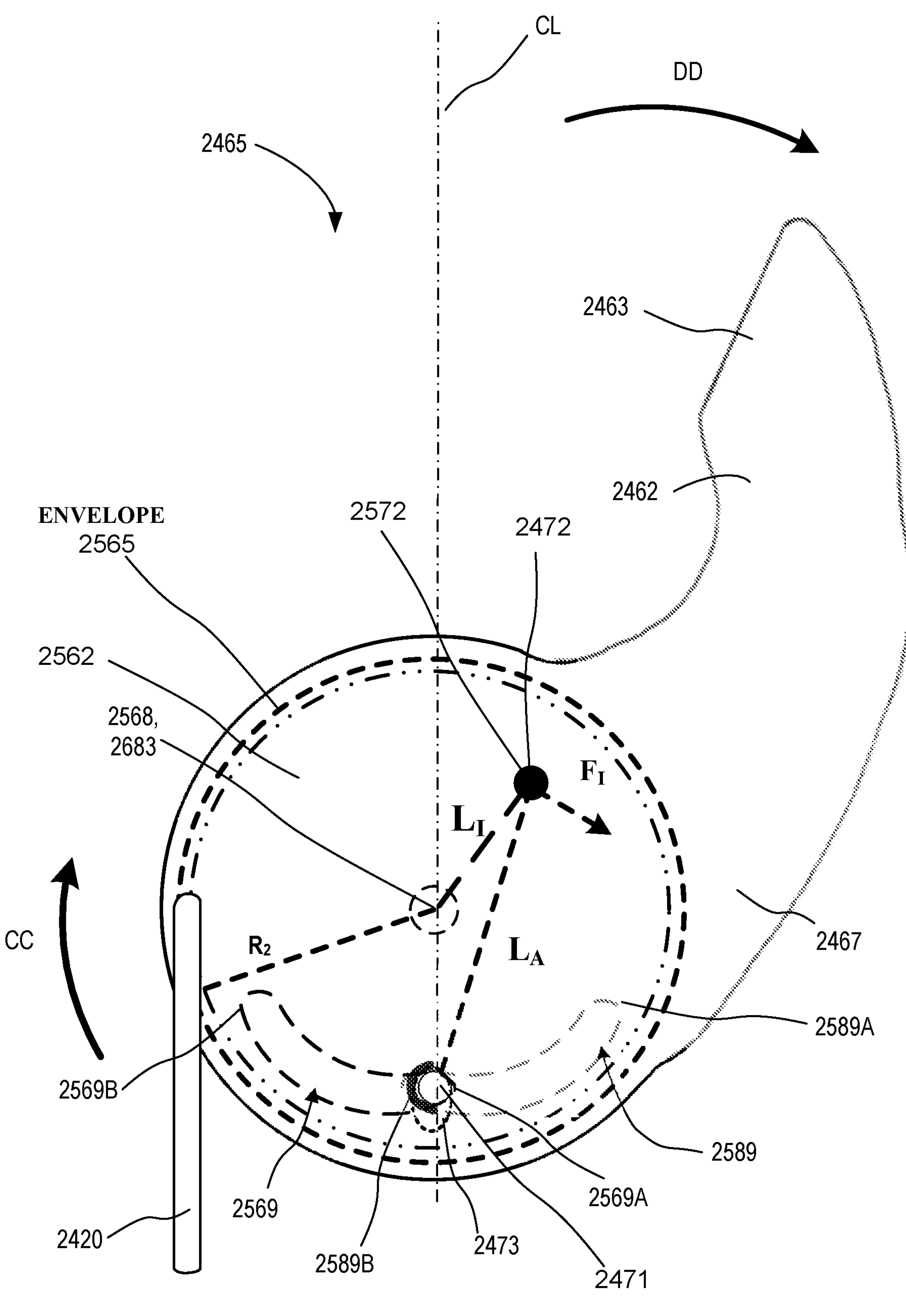

Additionally, the elongated shape of the first jaw pivot opening 2569 and the second jaw pivot opening 2589 allows relative motion between each rotatable member and its respective jaw (e.g., the second rotatable member 2582 and the second jaw 2482). The configuration of the first jaw pivot opening 2569 and the second jaw pivot opening 2589 also allows such relative motion while maintaining the jaw pivot axis $A_{JP}$, the input link $L_1$, and the kinematic link $L_A$ within the second envelope 2585 (and also the first envelope 2565). Similarly stated, the disk-shaped proximal portion 2487 of the second jaw 2482 remains within the envelope defined by the disk-shaped second rotatable member 2582. Because the jaw pivot pin 2471 is within each of the first jaw pivot opening 2569 and the second jaw pivot opening 2589, the side wall of the first rotatable member 2562 and the side wall of the second rotatable member 2582 can, in certain configurations, collectively limit movement of the jaw pivot pin 2471. For example, FIGS. 7, 8A, and 8B show the second jaw pivot opening 2589 superimposed about the first jaw pivot opening 2569. As shown in FIG. 7, when the end effector 2460 is in a partially opened configuration, the jaw pivot pin 2471 is within a middle portion of each of the first jaw pivot opening 2569 and the second jaw pivot opening 2589. As the rotatable members rotate, the movement of the jaw pivot pin 2471 is guided within the jaw pivot pin envelope 2473. Specifically, the first jaw pivot opening 2569 and the second jaw pivot opening 2589 are shaped to allow movement of the jaw pivot pin 2471 along the end effector center line CL. Said another way, the jaw pivot pin 2471 is configured to translate along a jaw pivot pin path defined by an intersection of a first curvilinear path (of the first jaw pivot opening 2569) and the second curvilinear path (of the second jaw pivot opening 2589).

As shown in FIG. 8A, when the end effector 2460 is in the closed configuration (e.g., to grasp a needle), there is clearance between the jaw pivot pin 2471 and a second end 2589B of the second jaw pivot opening 2589 and a first end 2569A of the first jaw pivot opening 2569. By ensuring end clearance, the jaws will not be subject to premature stopping (e.g., if the jaws are gripping a very thin object). As shown in FIG. 8B, the rotatable member 2562 rotates in a direction CC causing the first jaw 2462 to rotate as shown by the arrow DD to a fully opened configuration. When the end effector 2460 is in a fully opened configuration, the jaw pivot pin 2471 is in contact with a first end 2569A of the first jaw pivot opening 2569 and a second end 2589B of the second jaw pivot opening 2589. Thus, further relative motion between each jaw and its respective rotatable member (e.g., the second jaw 2482 and the second rotatable member 2582) is stopped. In this manner, the end effector 2460 includes end-stops to prevent over-rotation.

Figure 9:
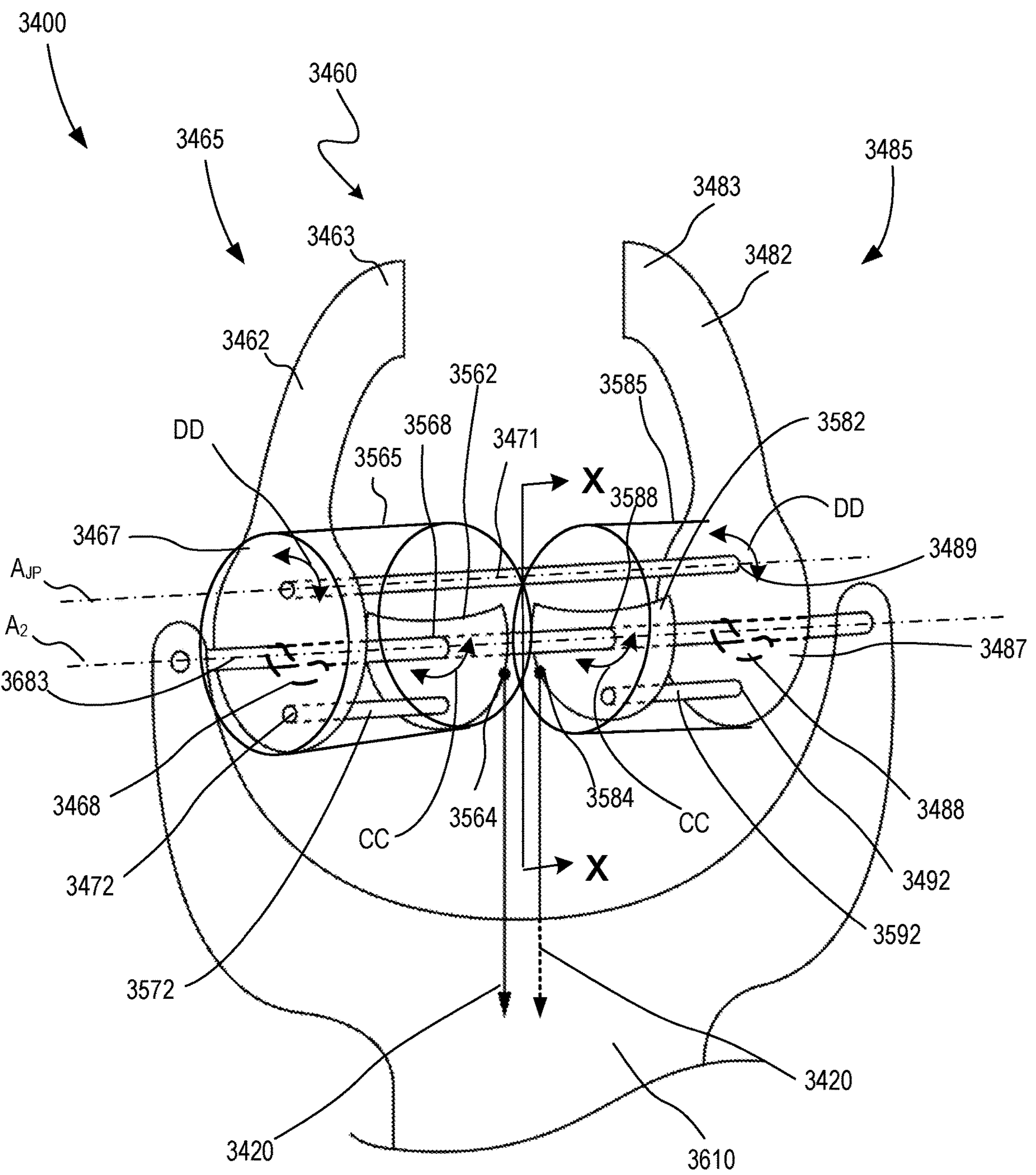
FIG. 9 is a diagrammatic perspective view of a portion of a medical instrument having two tool assemblies configured to amplify an input torque, according to an embodiment.
Figure 10:
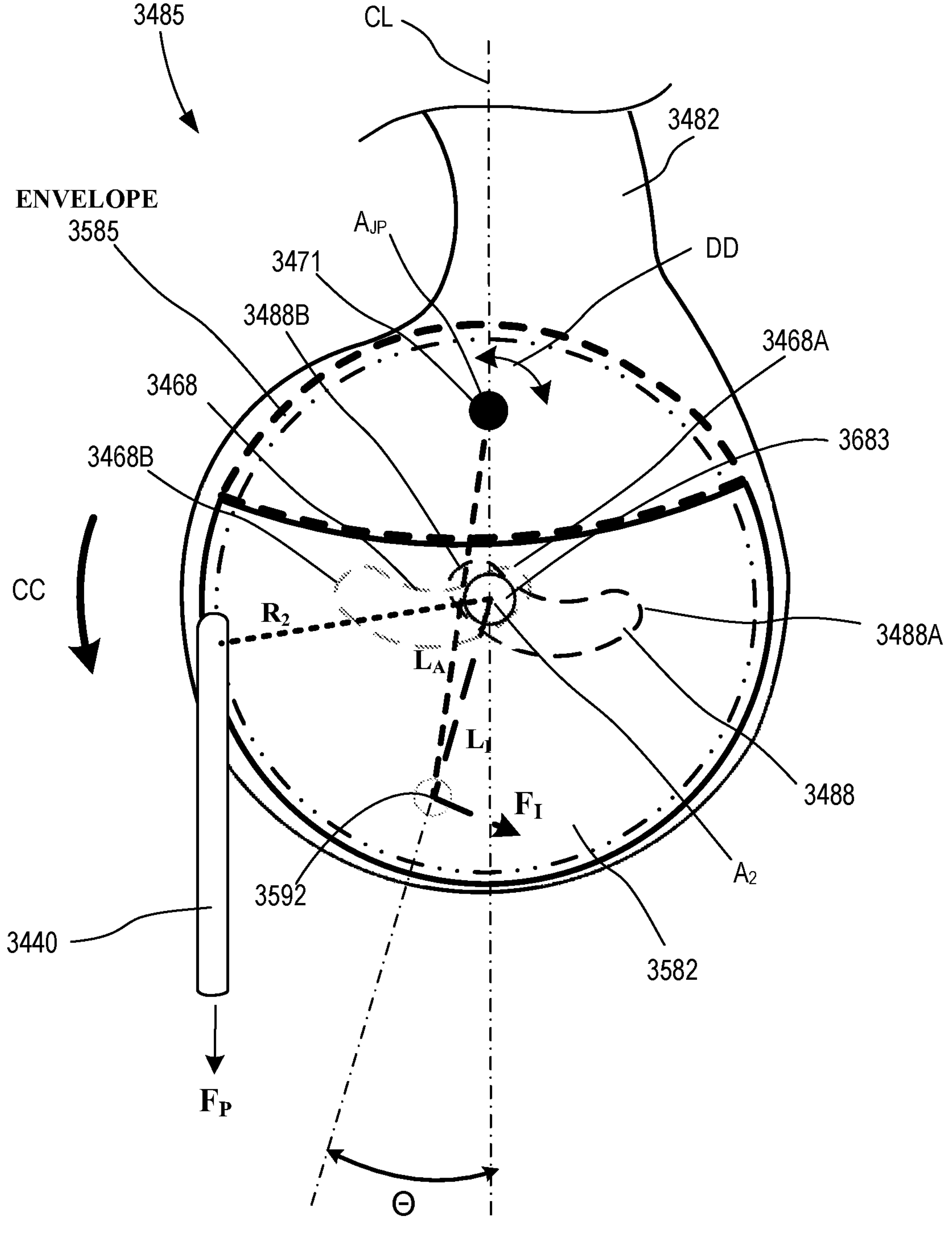
FIG. 10 is a side view of the medical instrument shown in FIG. 9 taken along line X-X to show one of the tool assemblies.

Although the end effector 2460 is shown as having the first jaw 2462 and the second jaw 2482 between the first rotatable member 2562 and the second rotatable member 2582 (i.e., the two jaws are sandwiched between the two rotatable members), in other embodiments, the two rotatable members can be between the two jaws. Additionally, although the end effector 2460 is shown as having a rear pivot topology, in other embodiments, an end effector can have a front pivot topology. For example, FIGS. 9 and 10 are schematic illustration of a distal end portion of an instrument 3400, according to an embodiment. The instrument 3400 includes a clevis 3610, an end effector 3460, a first tension member 3420, and a second tension member 3440. The first tension member 3420 and the second tension member 3440 can be a cable, a rod, or any other suitable structure to actuate the end effector 3460. The instrument can include a shaft (not shown) that couples the clevis 3610 and end effector 3460 to a mechanical structure (not shown). The mechanical structure can be any of the mechanical structures shown and described herein, and can function to move each of the first tension member 3420 and the second tension member 3440 to actuate the end effector 3460, as described herein.

In some embodiments, the clevis 3610 is a portion of a wrist assembly, and is rotatably coupled to one or more additional links or devises to provide for rotation of the clevis 3610 about the instrument shaft. In other embodiments, the clevis 3610 is coupled directly to the shaft and the instrument does not include a pitch rotation degree of freedom. The clevis includes a central pin 3683, which defines the central axis $A_2$ and to which the end effector 3460 is coupled. As shown, the central pin 3683 is a single structure that passes through the first jaw 3462, the first rotatable member 3562, the second rotatable member 3582, and the second jaw 3562.

The end effector 3460 includes a first tool assembly 3465 (which functions as a first jaw-rotatable member pair) and a second tool assembly 3485 (which functions as a second jaw-rotatable member pair). Although the first tool assembly 3465 and the second tool assembly 3485 are separate components that cooperatively function to form the end effector 3460, aspects of the first tool assembly 3465 described below (e.g., identification of kinematic links formed by the first tool assembly) are applicable to the second tool assembly 3485, and vice-versa. The first tool assembly 3465 includes a first jaw 3462 that is coupled to a first rotatable member 3562.

The first rotatable member 3562 can be any suitable structure for operatively coupling the first jaw 3462 to the first tension member 3420, such as a link, a gear, or a pulley. In this embodiment, the first rotatable member 3562 is a crescent-shaped member that is rotatably coupled to the clevis 3610 by the central pin 3683. As described, the shape of the first rotatable member 3562 is such that the jaw pivot pin 3471 is outside of an outer edge of the first rotatable member 3562. Even though the jaw pivot pin 3471 is outside of the structure of the first rotatable member 3562, it is still within the first envelope 3565 (which is the cylindrical volume about the central axis $A_2$). The first rotatable member 3562 includes a first input connector 3564 and a first output connector 3572, and defines a central opening 3568. The central pin 3683 is coupled within the central opening 3568 to allow the first rotatable member 3562 to rotate relative to the clevis 3610 about the central axis $A_2$, as shown by the arrow CC. The first tension member 3420 is coupled to the first rotatable member 3562 at the first input connector 3564. The first input connector 3564 can be any suitable connector or mechanism for securing the first tension member 3420 to the first rotatable member 3562, as described herein.

FIG. 10 is a side view showing the geometric layout of the second jaw 3482 and the second rotatable member, but the geometric layout is also applicable to the first tool assembly 3465. The first tension member 3420 is coupled to the first rotatable member 3562 at a first input radius (analogous to the second input radius $R_2$ shown in FIG. 10) from the central axis $A_2$. Thus, when an input force $F_P$ is applied by the first tension member 3420 onto the first rotatable member 3562, an input torque is produced about the central axis $A_2$ to rotate the first rotatable member 3562. Additionally, the first rotatable member 3562 defines a first envelope 3565 as the cylindrical volume about the central axis $A_2$ that has an envelope radius equal to the outer-most size (e.g., radius) of the first rotatable member 3562. In some embodiments, the first envelope 3565 has an envelope radius equal to the first input radius $R_1$ or the second input radius $R_2$.

The first output connector 3572 can be any suitable connector or mechanism that couples the first jaw 3462 to the first rotatable member 3562. Moreover, the first output connector 3572 is matingly coupled to a first connector 3472 of the first jaw 3462 to transfer forces from the first rotatable member 3562 to the first jaw 3462. In some embodiments, the first output connector 3572 can be a protrusion that is received within a corresponding opening of the first jaw 3462. In other embodiments, the first output connector 3572 can be an opening within which a protrusion from the first jaw 3462 is received. Referring to FIG. 10 (which shows the geometric layout of second tool assembly 3485 that is also applicable to the first tool assembly 3465), the first output connector 3572 is radially offset from the central axis $A_2$ by a jaw input length, identified as $L_1$. Thus, the coupling between the first rotatable member 3562 and the first jaw 3462 defines a kinematic link identified as $L_1$ that rotates about the central axis $A_2$. As shown, the first output connector 3572 and the kinematic link $L_1$ are within the first envelope 3565. Similarly stated, the jaw input length $L_1$ is less than the first input radius $R_1$ or the second input radius $R_2$.

The first jaw 3462 includes a distal portion 3463 and a proximal portion 3467. The distal portion 3463 functions as a grip portion to cooperate with the second jaw 3482 to contact tissue, grasp a needle, or perform other operations. The proximal portion 3467 includes the first connector 3472, which couples the first jaw 3462 to and transfers forces from the first rotatable member 3562. The first jaw 3462 is rotatably coupled to the second jaw 3482 by a jaw pivot pin 3471, which defines a jaw pivot axis $A_{JP}$. Thus, when the torque applied to the first rotatable member 3562 by the first tension member 3420 is transferred to the first jaw 3462, the first jaw 3462 rotates relative to the second jaw 3482 (and also the clevis 3610) about the jaw pivot axis $A_{JP}$, as shown by the arrow DD. Referring again to FIG. 10 (which is applicable to the first tool assembly 3465), the jaw pivot axis $A_{JP}$ is offset from the central axis $A_2$ along an end effector center line CL. The jaw pivot axis $A_{JP}$ is also offset from the first connector 3472 by a jaw applied length, identified as $L_A$. Thus, the coupling of the jaws at the jaw pivot pin 3471 and the coupling of the first jaw 3462 and the first rotatable member 3562 at the first connector 3472 defines a kinematic link identified as $L_A$ that rotates about the jaw pivot axis $A_{JP}$. As shown, the jaw pivot axis $A_{JP}$ and the kinematic link $L_A$ are within the first envelope 3565. The jaw applied length $L_A$, however, is greater than the first input radius $R_1$ or the second input radius $R_2$.

The second tool assembly 3465 includes a second jaw 3482 that is coupled to a second rotatable member 3582. Like the first rotatable member 3562, the second rotatable member 3582 is a crescent-shaped member that is rotatably coupled to the clevis 3610 by the central pin 3683. The second rotatable member 3582 includes a second input connector 3584 and a second output connector 3592, and defines a central opening 3588. The central pin 3683 is coupled within the central opening 3588 to allow the second rotatable member 3582 to rotate relative to the clevis 3610 about the central axis $A_2$, as shown by the arrow CC. The second tension member 3440 is coupled to the second pulley 3582 at the second input connector 3584. The second input connector 3584 can be any suitable connector or mechanism for securing the second tension member 3440 to the second rotatable member 3582, as described herein.

Referring to FIG. 10, the second tension member 3440 is coupled to the second rotatable member 3582 at a second input radius $R_2$ from the central axis $A_2$. Thus, when an input force $F_P$ is applied by the second tension member 3440 onto the second rotatable member 3582, an input torque is produced about the central axis $A_2$ to rotate the second rotatable member 3582. Additionally, the second rotatable member 3582 defines a second envelope 3585 as the cylindrical volume about the central axis $A_2$ that has an envelope radius equal to the outer-most size (e.g., radius) of the second rotatable member 3582. In some embodiments, the second envelope 3585 has an envelope radius equal to the second input radius $R_2$. In some embodiments, the second input radius $R_2$ is equal to the first input radius $R_1$ and the second envelope 3585 is the same as the first envelope 3565. The second output connector 3592 can be any suitable connector or mechanism that couples the second jaw 3482 to the second rotatable member 3582. Moreover, the second output connector 3592 is matingly coupled to a second connector 3492 of the second jaw 3482 to transfer forces from the second rotatable member 3582 to the second jaw 3482. Referring to FIG. 10, the second output connector 3592 is radially offset from the central axis $A_2$ by a jaw input length, identified as $L_1$. Thus, the coupling between the second rotatable member 3582 and the second jaw 3482 defines a kinematic link identified as $L_1$ that rotates about the central axis $A_2$. As shown, the second output connector 3592 and the kinematic link $L_1$ are within the second envelope 3585.

The second jaw 3482 includes a distal portion 3483 and a proximal portion 3487. The distal portion 3483 functions as a grip portion to cooperate with the first jaw 3462 to contact tissue, grasp a needle, or perform other operations. The proximal portion 3487 includes the second connector 3492, which couples the second jaw 3482 to and transfers forces from the second rotatable member 3582. The first jaw 3462 is rotatably coupled to the second jaw 3482 by the jaw pivot pin 3471. Thus, when the torque applied to the second rotatable member 3582 by the second tension member 3440 is transferred to the second jaw 3482, the second jaw 3482 rotates relative to the first jaw 3462 (and also the clevis 3610) about the jaw pivot axis $A_{JP}$, as shown by the arrow DD. The jaw pivot axis $A_{JP}$ is offset from the second connector 3492 by a jaw applied length, identified as $L_A$. Thus, the coupling of the jaws at the jaw pivot pin 3471 and the coupling of the second jaw 3482 and the second rotatable member 3582 at the second connector 3492 defines a kinematic link identified as $L_A$ that rotates about the jaw pivot axis $A_{JP}$. As shown, the jaw pivot axis $A_{JP}$ and the kinematic link $L_A$ are within the second pulley envelope 3585.

As mentioned above, the first jaw 3462 includes defines the first central opening 3468 and the second jaw 3482 defines the second central opening 3488. As shown, the central pin 3683 extends through the first central opening 3468 and the second central opening 3488. Additionally, the first central opening 3468 and the second central opening 3488 are each elongated to allow movement of the first jaw 3462 and the second jaw 3482 about the central pin 3683 during operation. As shown in FIG. 10, the first central opening 3468 includes a first end 3468A and a second end 3468B and the second central opening 3488 includes a first end 3488A and a second end 3488B. As described in more detail below, during use the boundaries of the first central opening 3468 and the second central opening 3488 can constrain the movement of the jaws during operation. Said another away, the shape, size, or both the shape and size of the first central opening 3468 and the second central opening 3488 can, in certain configurations, limit the movement of the first jaw 3462 and the second jaw 3482 during use. The central openings (or slots) can thus allow the jaws to translate relative to the central pin 3683 and the pulleys. Although the first central opening 3468 and the second central opening 3488 are shown as being curved (to define a curvilinear path), in other embodiments, either or both of the first central opening 3468 and the second central opening 3488 can be linear elongated slots. In yet other embodiments, either or both of the first central opening 3468 and the second central opening 3488 can have a curved section and a linear section. Although the crescent shape of the first rotatable member 3562 and the second rotatable member 3582 obviate the need for jaw pivot openings in the rotatable members, in other embodiments, an end effector can include both elongated central openings, similar to the first central opening 3468 and the second central opening 3488 as well as elongated jaw pivot openings, similar to the first jaw pivot opening 2569 and the second jaw pivot opening 2589, described above.

As shown, the first tool assembly 3465 and the second tool assembly 3485 have a front pivot topology. Specifically, the jaw pivot axis $A_{JP}$ is offset from the central axis $A_2$ along an end effector center line CL (see FIG. 10), with the central axis $A_2$ being further from the jaw tip than the jaw pivot axis. Said another way, the jaw pivot axis $A_{JP}$ is between the jaw central axis $A_2$ and the distal end 3463, 3483 of the jaws 3462, 3482. Additionally, the first tool assembly 3465 and the second tool assembly 3485 have a forward grip topology. Referring to FIG. 10, the end effector center line CL is defined between (and normal to) the central axis $A_2$ and the jaw pivot axis $A_{JP}$. The input link $L_1$ rotates about the central axis $A_2$ when the input pulley force $F_P$ is applied to the pulleys. Thus, the input link $L_1$ and the end effector center line CL form an input link angle Θ. When the rotatable members rotate to move the end effector 3460 from the closed configuration to an opened configuration, the input link angle Θ increases. In other embodiments, an end effector can have a reverse grip topology (where the input link angle decreases when the end effector moves from the closed configuration to an opened configuration.

In use, the end effector 3460 can amplify the input force $F_P$ to produce a higher grip force produced by the jaws 3462, 3482 than would be produced with a standard single-piece jaw and pulley system. As described below, the end effector 3460 (and each of the tool assemblies 3465, 3485) includes additional kinematic linkages to increase the moment arm upon which the input force $F_P$ is exerted, thereby increasing the output grip force. A general description of the force amplification is described below with reference to FIG. 10, which shows the geometric layout of second tool assembly 3485, but which is also applicable to the first tool assembly 3465. Additionally, the free-body diagrams and grip force equations discussed below are also applicable to the end effector 3460. As shown, the input force $F_P$ is applied to the second input connector of the second rotatable member 3582. The input force $F_P$ acts through the second input radius $R_2$ to produce an input torque $T_1$ about the central axis $A_2$, in the direction shown by the arrow CC. The input torque $T_1$ is applied throughout the second rotatable member 3582 within the rotation plane of the second rotatable member 3582 such that a resultant input force is produced at the interface of the second output connector 3572 (of the second rotatable member) and the second connector 3472 (of the second jaw 3482). In this manner, the input force acts upon the second jaw 3482. Specifically, when the second rotatable member 3582 rotates about the central axis $A_2$ (arrow CC), the input force causes the second jaw 3482 to rotate about the jaw pivot pin 3471 (which defines the jaw pivot axis $A_{JP}$), as shown by the arrow DD. The magnitude of the input force $F_1$ is based on the length of the input link $L_1$ and the resulting input force is proportional to the input pulley force $F_P$ by the ratio of the lengths ($R_2/L_1$). Similarly, the kinematic link $L_A$ (i.e., the jaw applied length) acts as a torque moment arm for the input force that is transferred via the interface of the second output connector 3572 (of the second rotatable member) and the second rotatable member connector 3472 to drive rotation of the second jaw 3482. The component of the input force that is normal to the kinematic link $L_A$ produces an applied torque on the second jaw 3482 that is proportional to the length $L_A$. Because the length of the kinematic link $L_A$ is longer than the length of the input link, $L_1$ (due to the second output connector 3572 and the second connector 3472 being offset from the jaw pivot pin 3471) tool assembly 3485 provides an amplified drive torque to the second jaw 3482 to drive its rotation. Similarly stated, by spacing the interface of the second output connector 3572 and the second pulley connector 3472 on one side of central pin 3683 and apart from the jaw pivot pin 3471 located the other side of the central pin 3588, mechanical advantage can be gained via the pulley-rotatable member pair.

Additionally, the elongated shape of the first central opening 3468 and the second central opening 3488 allows relative motion between each rotatable member and its respective jaw (e.g., the second rotatable member 3582 and the second jaw 3482). The configuration of the first central opening 3468 and the second central opening 3488 also allows such relative motion while maintaining the jaw pivot axis $A_{JP}$, the input link $L_1$, and the kinematic link $L_A$ within the second envelope 3585 (and also the first envelope 3565). Similarly stated, the disk-shaped proximal portion 3487 of the second jaw 3482 remains within the envelope defined by the disk-shaped second rotatable member 3582. Because the central pin 3683 is within each of the first central opening 3468 and the second central opening 3488, the side wall of the first jaw 3462 and the side wall of the second jaw 3482 can, in certain configurations, collectively limit movement of the jaws relative to the pulleys. For example, FIG. 10 show the first central opening 3468 superimposed about the second central opening 3488. When the end effector 3460 is in the closed configuration (e.g., to grasp a needle), the central pin 3683 has clearance with (i.e., is spaced apart from) a second end 3488B of the second central opening 3488 and a first end 3468A of the first central opening 3468. Thus, further relative motion between each jaw and its respective rotatable member (e.g., the second jaw 3482 and the second rotatable member 3582) will not be premature limited. When the end effector 3460 is in a fully opened configuration, the central pin 3683 is in contact with a first end 3488A of the second central opening 3488 and a second end 3468B of the first central opening 3468. Thus, further relative motion between each jaw and its respective pulley (e.g., the second jaw 3482 and the second pulley 3582) is stopped. In this manner, the end effector 3460 includes end-stops to prevent over-rotation.

Figure 11:
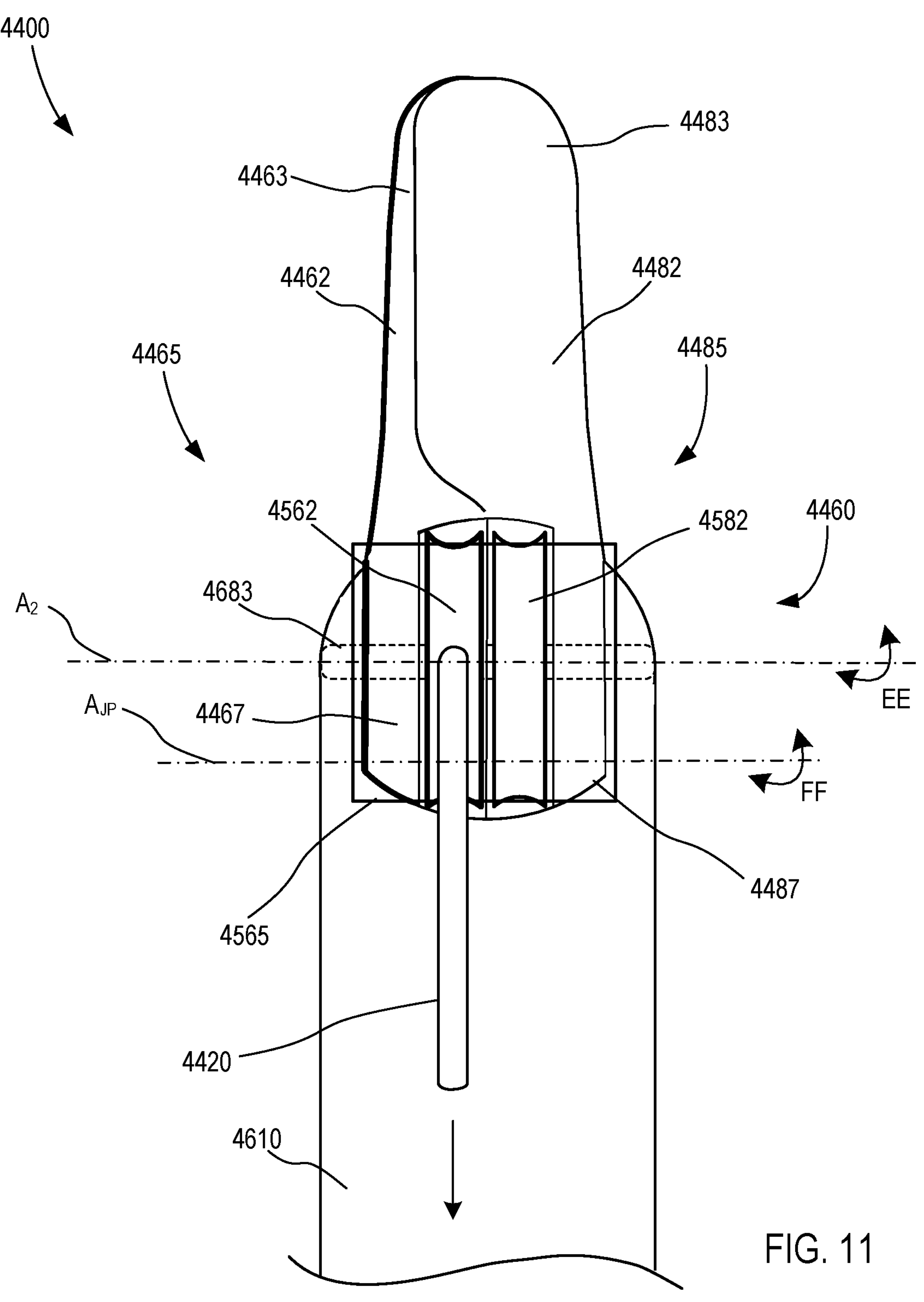
FIG. 11 is a front view of a portion of a medical instrument having two tool assemblies configured to amplify an input torque, according to an embodiment.
Figure 12:
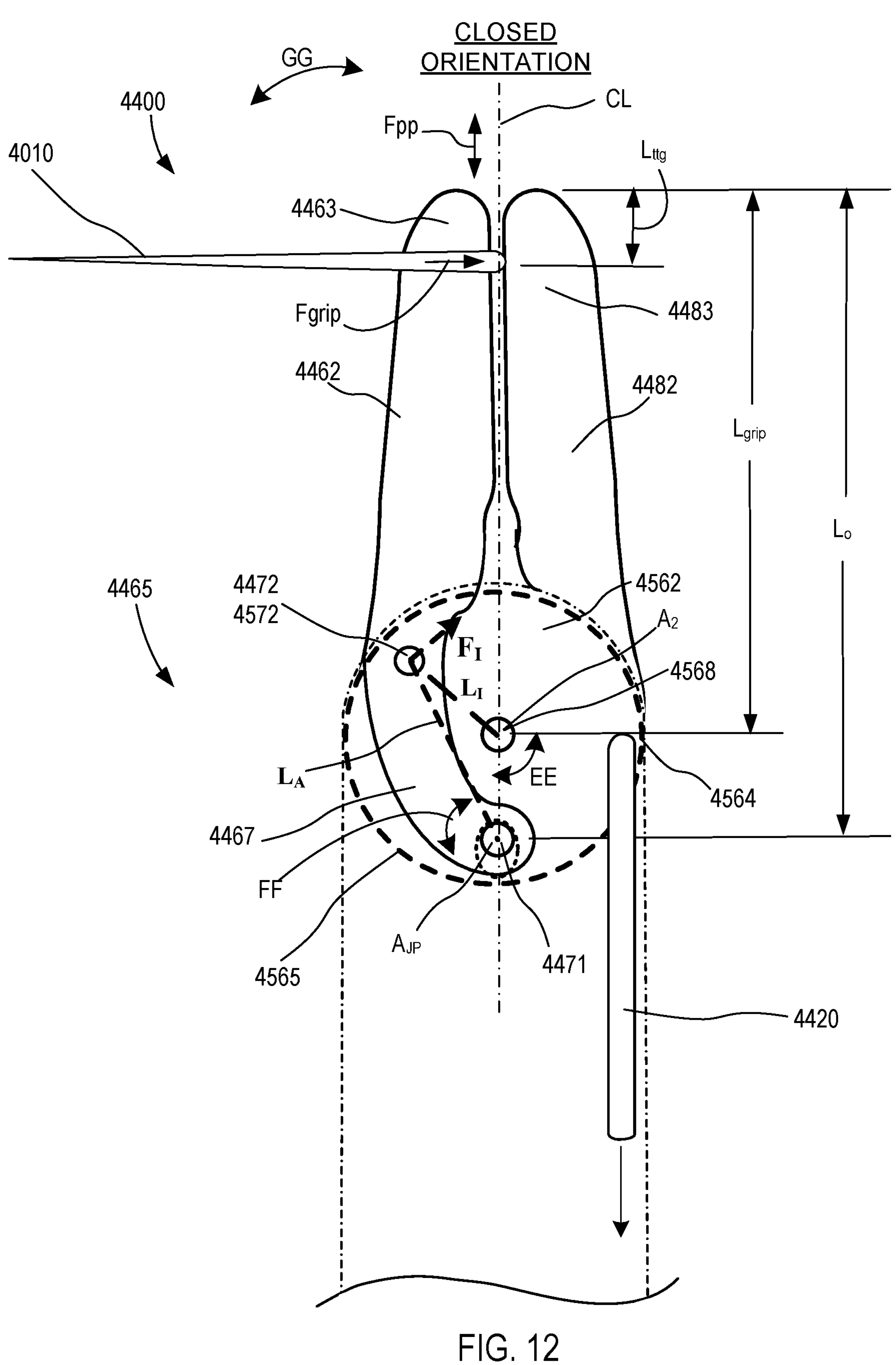
FIG. 12 is a side view of the portion of the medical instrument shown in FIG. 11 showing the rear pivot/forward grip topology of the tool assemblies.
Figures 13A, 13B:
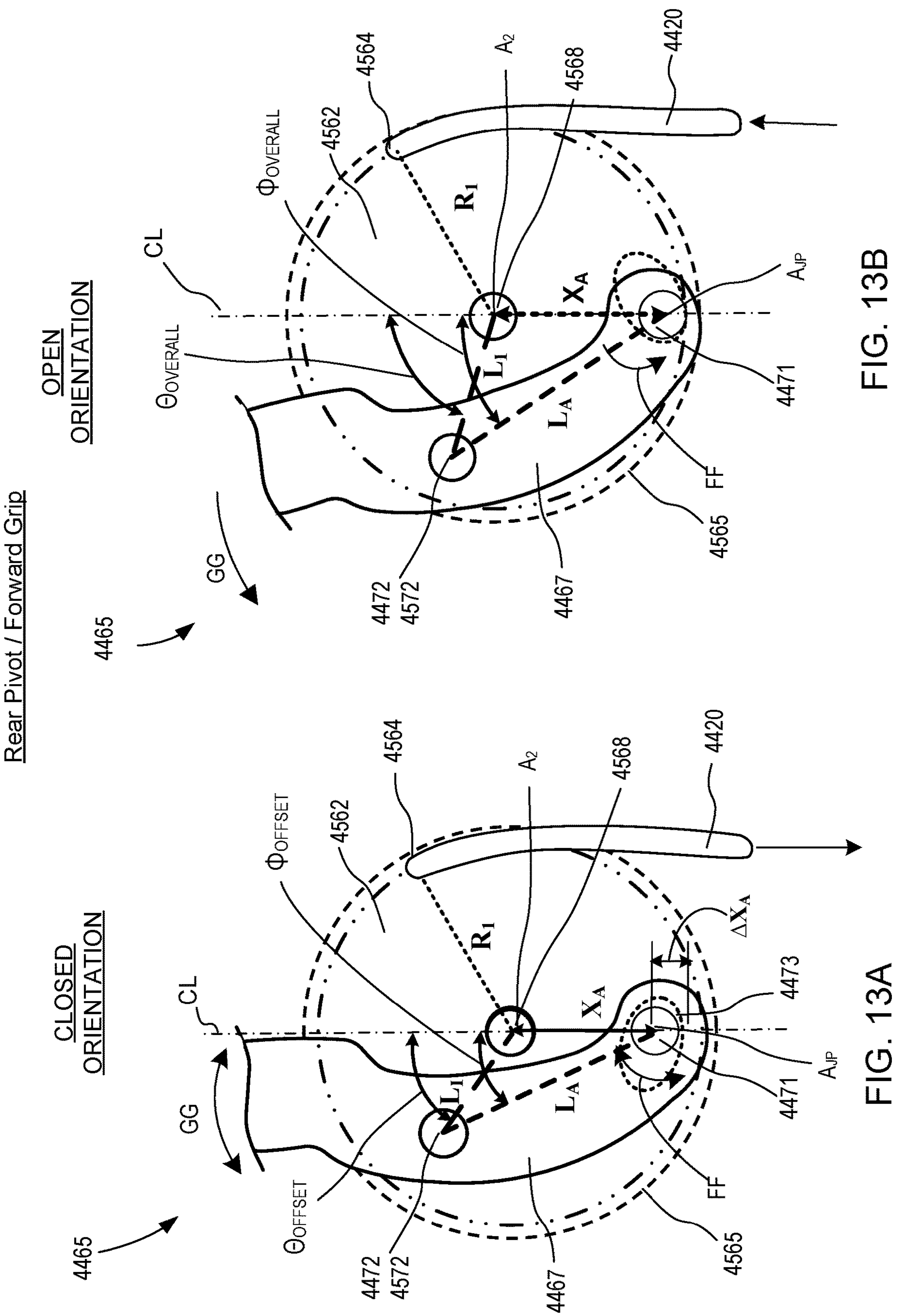
FIGS. 13A and 13B are side views of a tool assembly shown in FIG. 12 in a first (closed) configuration (FIG. 13A) and a second (open) configuration (FIG. 13B).
Figure 14:
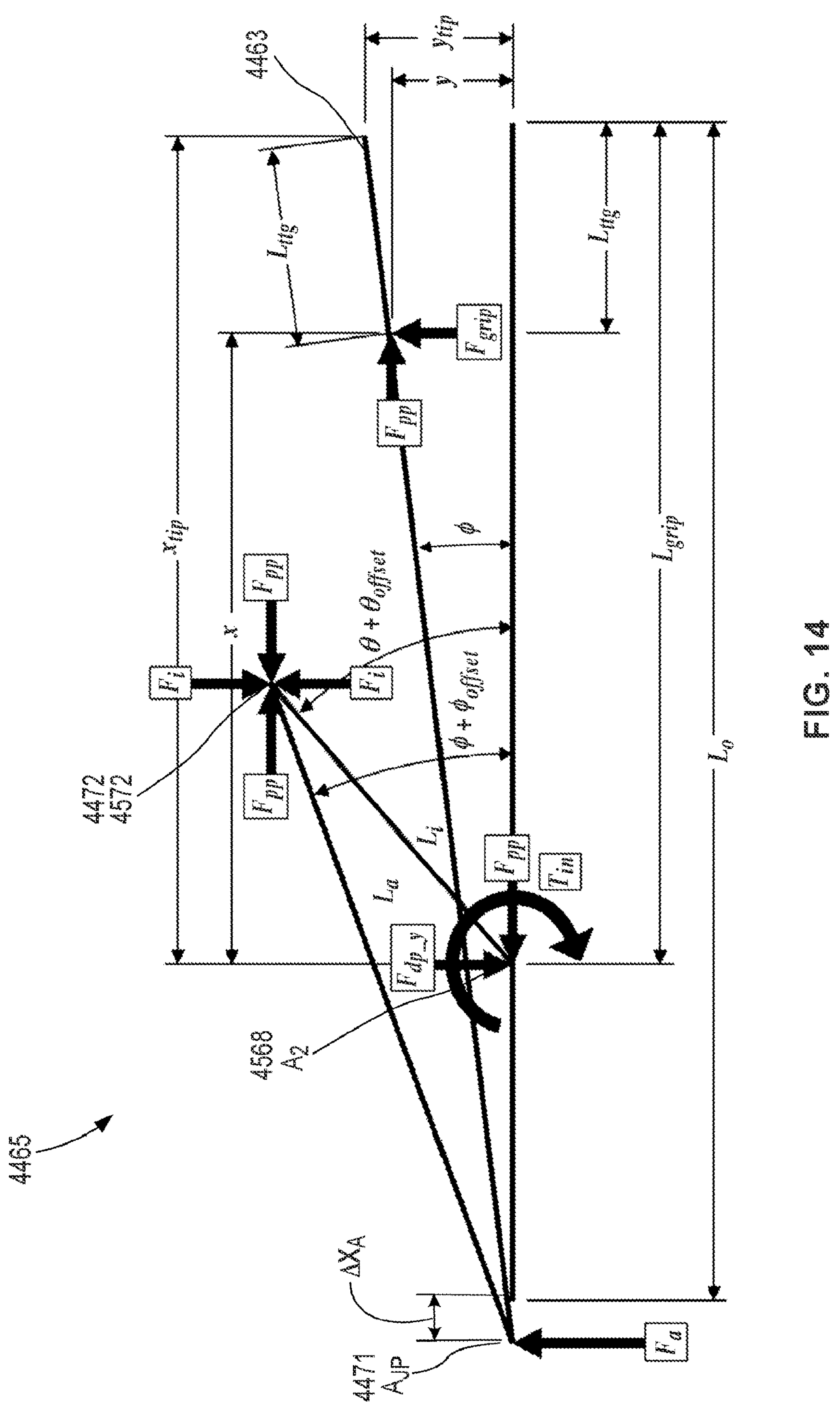
FIG. 14 is a free-body diagram of the tool assembly shown in FIG. 12 showing the forces and torques acting on various joint of the tool assembly.

FIGS. 11-14 are schematic illustrations of a distal end portion of an instrument 4400 having a rear pivot and forward grip topology, according to an embodiment. Specifically, FIG. 11 is a front view and FIG. 12 is a side view of the instrument. FIGS. 13A and 13B are enlarged side views of a portion of the instrument 4400 in a first (closed) configuration (FIG. 13A) and a second (open) configuration (FIG. 13B). Finally, FIG. 14 is a free-body diagram showing the forces and torques acting on various joint of the tool assembly. The instrument 4400 includes a clevis 4610, an end effector 4460, a first cable 4420 (which functions as a first tension member), and a second cable (not shown). The instrument can include a shaft (not shown) that couples the clevis 4610 and end effector 4460 to a mechanical structure (not shown). The mechanical structure can be any of the mechanical structures shown and described herein, and can function to move the cables to actuate the end effector 4460, as described herein. In some embodiments, the clevis 4610 is a portion of a wrist assembly, and is rotatably coupled to one or more additional links or devises to provide for rotation of the clevis 4610 about the instrument shaft. In other embodiments, the clevis 4610 is coupled directly to the shaft and the instrument does not include a pitch rotation degree of freedom. The clevis includes a central pin 4683, which defines the central axis $A_2$ and to which the end effector 4460 is coupled.

The end effector 4460 includes a first tool assembly 4465 (which functions as a first jaw-pulley pair) and a second tool assembly 4485 (which functions as a second jaw-pulley pair). Although the first tool assembly 4465 and the second tool assembly 4485 are separate components that cooperatively function to form the end effector 4460, aspects of the first tool assembly 4465 described below (e.g., identification of kinematic links formed by the first tool assembly) are applicable to the second tool assembly 4485, and vice-versa. Thus, although certain figures describe the first tool assembly 4465, the description is applicable to the second tool assembly 4485. The first tool assembly 4465 includes a first jaw 4462 coupled to a first pulley 4562 and the second tool assembly 4485 includes a second jaw 4482 coupled to a second pulley 4582. The first jaw 4462 includes a distal portion 4463 and a proximal portion 4467 and the second jaw 4482 includes a distal portion 4483 and a proximal portion 4487. The proximal portions 4467, 4487 each include a pulley connector, which couples the jaw to and transfers forces from its mating pulley (e.g., the proximal portion 4467 includes a first pulley connector 4472, which couples the first jaw 4462 to and transfers forces from the first pulley 4562). Additionally, the proximal portion 4467 of the first jaw 4462 is rotatably coupled to the proximal portion 4487 of the second jaw 4482 by a jaw pivot pin 4471, which defines a jaw pivot axis $A_{JP}$. The distal portions 4463, 4483 function as grip portions to cooperatively contact tissue, grasp a needle, or perform other operations.

For example, as shown in FIG. 12, the distal portion 4463 of the first jaw 4462 and the distal portion 4483 of the second jaw 4482 can function together to grip a suture needle 4010 when the end effector 4460 is in the closed configuration. Specifically, the jaws can exert a grip force Fgrip to clamp the needle 4010. A push-pull force Fpp can also be exerted on (or by) the jaws. For example, the push-pull force Fpp can be exerted by the jaws when the end effector 4460 moves from an opened configuration to the closed configuration due to the translational movement of the first jaw 4462 and the second jaw 4482 along the end effector center line CL. As shown, the first jaw 4462 and the second jaw 4482 each have an overall length $L_O$ from the jaw pivot axis $A_{JP}$ to the tip of the first jaw 4462 and the second jaw 4482. The first jaw 4462 and the second jaw 4482 each have a grip length $L_{grip}$ from the center axis $A_2$ to the tip of the first jaw 4462 and the second jaw 4482. The distance from the tip of the jaws to position where the needle 4010 is engaged is identified as the tip-to-grip distance Lttg.

The first pulley 4562 is a disk-shaped member that is rotatably coupled to the clevis 4610 by the central pin 4683. The first pulley 4562 includes a first input connector 4564 and a first output connector 4572, and defines a central opening 4568 and a first jaw pivot opening (not identified, but that can be similar to the jaw pivot opening 2569 described above). The central pin 4683 is coupled within the central opening 4568 to allow the first pulley 4562 and the second pulley 4582 to rotate relative to the clevis 4610 about the central axis $A_2$, as shown by the arrow EE. The first cable 4420 is coupled to the first pulley 4562 at the first input connector 4564. The first input connector 4564 can be any suitable connector or mechanism for securing the first cable 4420 to the first pulley 4562, as described herein. Referring to FIGS. 13A and 13B, the first cable 4420 is coupled to the first pulley 4562 at a first input radius $R_1$ from the central axis $A_2$. Thus, when an input pulley force is applied by the first cable 4420 onto the first pulley 4562, an input torque $T_{in}$ is produced about the central axis $A_2$ to rotate the first pulley 4562, as shown by the arrow EE in FIGS. 11 and 12. Additionally, the first pulley 4562 defines a first pulley envelope 4565 as the cylindrical volume about the central axis $A_2$ that has an envelope radius equal to the outer-most radius of the first pulley 4562. In some embodiments, the first pulley envelope 4565 has an envelope radius equal to the first input radius $R_1$. In some embodiments, the first pulley envelope 4565 is the same as a pulley envelope defined by the second pulley 4582.

The first output connector 4572 can be any suitable connector or mechanism that couples the first jaw 4462 to the first pulley 4562 to transfer forces from the first pulley 4562 to the first jaw 4462. In some embodiments, the first output connector 4572 can be a protrusion that is received within a corresponding opening of the first jaw 4462. In other embodiments, the first output connector 4572 can be an opening within which a protrusion from the first jaw 4462 is received. Referring to FIGS. 13A and 13B, the first output connector 4572 is radially offset from the central axis $A_2$ by a jaw input length, identified as $L_1$. Thus, the coupling between the first pulley 4562 and the first jaw 4462 defines a kinematic input link identified as $L_1$ that rotates about the central axis $A_2$. The input link $L_1$ and the end effector center line CL form an input link angle that changes when the first pulley 4562 rotates about the central axis $A_2$. When the end effector 4460 is in the closed configuration (see FIGS. 12 and 13A), the input link angle is identified as $\Theta_{OFFSET}$. When the pulley rotates towards the open position (see FIGS. 13B and 14), the input link angle increases to a value of $\Theta+\Theta_{OFFSET}$ (also referred to as $\Theta_{OVERALL}$). As described in more detail below, the value of $\Theta_{OFFSET}$ can be selected to minimize the impact of the push-pull force Fpp on the grip force Fgrip. For example, in some embodiments, the value of $\Theta_{OFFSET}$ can be less than about 5 degrees. In some embodiments, the value of $\Theta_{OFFSET}$ can be about zero degrees. Similarly stated, in some embodiments, the coupling between the first pulley 4562 and the first jaw 4462 is along the end effector center line CL when the end effector 4460 is in the closed configuration. As shown, the first output connector 4572 and the kinematic link $L_1$ are within the first pulley envelope 4565. Similarly stated, the jaw input length $L_1$ is less than or equal to the to the first input radius $R_1$.

The proximal portion 4467 of the first jaw 4462 includes the first pulley connector 4472, which couples the first jaw 4462 to and transfers forces from the first pulley 4562. Thus, when the input torque $T_{in}$ applied to the first pulley 4562 by the first cable 4420 is transferred to the first jaw 4462, the first jaw 4462 rotates relative to the second jaw 4482 (and also the clevis 4610) about the jaw pivot axis $A_{JP}$, as shown by the arrow GG in FIGS. 13A and 13B. The jaw pivot axis $A_{JP}$ is offset from the central axis $A_2$ along an end effector center line CL, which is defined between (and normal to) the central axis $A_2$ and the jaw pivot axis $A_{JP}$ when the end effector is in its closed configuration, as shown in FIG. 12. As shown in FIGS. 13A and 13B, the offset distance between the jaw pivot axis $A_{JP}$ and the central axis $A_2$ is indicated as $X_A$. The jaw pivot axis $A_{JP}$ is also offset from the first pulley connector 4472 by a jaw applied length, identified as $L_A$. Thus, the coupling of the jaws at the jaw pivot pin 4471 and the coupling of the first jaw 4462 and the first pulley 4562 at the first pulley connector 4472 defines a kinematic applied link identified as $L_A$ that rotates about the jaw pivot axis $A_{JP}$. The applied input link $L_A$ and the end effector center line CL form an applied link angle that changes when the first jaw 4462 rotates about the central axis $A_2$ and the jaw pivot axis $A_{JP}$. When the end effector 4460 is in the closed configuration (see FIGS. 12 and 13A), the input link angle is identified as $\Phi_{OFFSET}$. When the pulley rotates towards the open position (see FIGS. 13B and 14), the applied link angle increases to a value of $\Phi+\Phi_{OFFSET}$ (also referred to as $\Phi_{OVERALL}$). As shown, the jaw pivot axis $A_{JP}$ and the kinematic link $L_A$ are within the first pulley envelope 4565.

As mentioned above, the first pulley 4562 and the second pulley 4582 each define a jaw pivot opening (similar to the jaw pivot openings 2569 and 2589 described above) through which the jaw pivot pin 4471 extends. More particularly, the jaw pivot openings are elongated to allow movement of the jaw pivot pin 4471 relative to the first pulley 4562 and the second pulley 4582 during operation (e.g., during relative motion between the jaws and the pulleys). Thus, in certain configurations (e.g., fully opened) the walls of the pulleys that define the jaw pivot can limit the movement of the jaw pivot pin 4471. Specifically, as shown in FIGS. 13A and 13B, as the jaws rotate relative to the pulleys rotate, the movement of the jaw pivot pin 4471 occurs within a jaw pivot pin envelope 4473 (with the movement along the end effector center line CL indicated as $\Delta X_A$). The jaw pivot openings can be any suitable shape and size to limit the movement of the jaw pivot pin 4471 during use.

As shown in FIGS. 13A and 13B, the first tool assembly 4465 and the second tool assembly 4485 have a rear pivot topology. Specifically, the jaw pivot axis $A_{JP}$ is further from the jaw tip than is the central axis $A_2$. Said another way, the central axis $A_2$ is between the jaw pivot axis $A_{JP}$ and the distal end (or grip portions) 4463, 4483 of the jaws 4462, 4482. Additionally, the first tool assembly 4465 and the second tool assembly 4485 have a forward grip topology. Specifically, when the pulleys rotate to move the end effector 4460 from the closed configuration (FIG. 13A) to an opened configuration (FIG. 13B), the input link angle $\Theta$ increases.

In use, the end effector 4460 can amplify the input pulley force $F_P$ to produce a higher grip force Fgrip produced by the jaws 4462, 4482 than would be produced with a standard single-piece jaw and pulley system. Specifically, the arrangement of the input link $L_1$ (including the input link angle $\Phi_{OFFSET}$) and the applied link $L_A$, together with the range of lengths of the jaws can amplify the grip force Fgrip. FIG. 14 provides a free-body diagram showing the geometry of the first tool assembly 4465 when the end effector is in an opened position. Considering the input link $L_1$ in isolation, the moment balance taken around the central axis $A_2$ is provided by Equation (1), which can be reduced produce Equation (2) and Equation (3) for the resultant forces, at the central axis $A_2$.

$$\sum M_{dp} = -T_{in} + F_i \cdot \cos(\theta+\theta_{offset}) \cdot L_i - F_{pp} \cdot \sin(\theta+\theta_{offset}) \cdot L_i = 0 \qquad \text{Eq (1)}$$

$$F_i = \frac{T_{in}}{\cos(\theta+\theta_{offset}) \cdot L_i} + F_{pp} \cdot \tan(\theta+\theta_{offset}) \qquad \text{Eq (2)}$$

$$F_{dp} = \frac{T_{in}}{\cos(\theta+\theta_{offset}) \cdot L_i} + F_{pp} \cdot \tan(\theta+\theta_{offset}) \qquad \text{Eq (3)}$$

Considering the applied link $L_A$ in isolation, the moment balance taken around the jaw pivot axis $A_{JP}$ is provided by Equation (4). Reducing this equation (including substituting the expression for $F_1$) produces Equation (5) for the grip force Fgrip. As shown by Equation (5), the grip force Fgrip includes a component based on the input torque $T_{in}$ and the push-pull force Fpp.

$$\sum M_a = -F_i \cdot \cos(\phi+\phi_{offset}) \cdot L_a + F_{pp} \cdot \sin(\phi+\phi_{offset}) \cdot L_a - F_{pp} \cdot \sin(\phi) \cdot (L_o - L_{ttg}) + F_{grip} \cdot \cos(\phi) \cdot (L_o - L_{ttg}) = 0 \qquad \text{Eq (4)}$$

$$F_{grip} = T_{in} \cdot \frac{L_a}{L_i} \cdot \frac{1}{(L_o - L_{ttg})} \cdot \frac{1}{\cos(\phi)} \frac{\sqrt{1 - \left(\sin(\theta+\theta_{offset}) \cdot \frac{L_i}{L_a}\right)^2}}{\cos(\theta+\theta_{offset})} + F_{pp} \cdot \left( \frac{\tan(\theta+\theta_{offset}) \cdot \sqrt{L_a^2 - (\sin(\theta+\theta_{offset}) \cdot L_i)^2}}{\cos(\phi) \cdot (L_o - L_{ttg})} - \frac{\sin(\theta+\theta_{offset}) \cdot L_i}{\cos(\phi) \cdot (L_o - L_{ttg})} + \tan(\phi) \cdot (L_o - L_{ttg}) \right) \qquad \text{Eq (5)}$$

If no push-pull force is present (i.e., Fpp=0), the grip force Fgrip is given by Equation (6). As indicated, the grip force increases with increasing angle. Additionally, if the input link angle $\Theta$ is set to zero, when the end effector 4460 is closed, the push-pull force Fpp has no effect on the grip force Fgrip (see Equation (7)).

$$F_{grip} = T_{in} \cdot \frac{L_a}{L_i} \cdot \frac{1}{(L_o - L_{ttg})} \cdot \frac{1}{\cos(\phi)} \cdot \frac{\sqrt{1 - \left(\sin(\theta+\theta_{offset}) \cdot \frac{L_i}{L_a}\right)^2}}{\cos(\theta+\theta_{offset})} \qquad \text{Eq (6)}$$

$$F_{grip} = T_{in} \cdot \frac{L_a}{L_i} \cdot \frac{1}{(L_o - L_{ttg})} \qquad \text{Eq (7)}$$

Figures 15A, 15B:
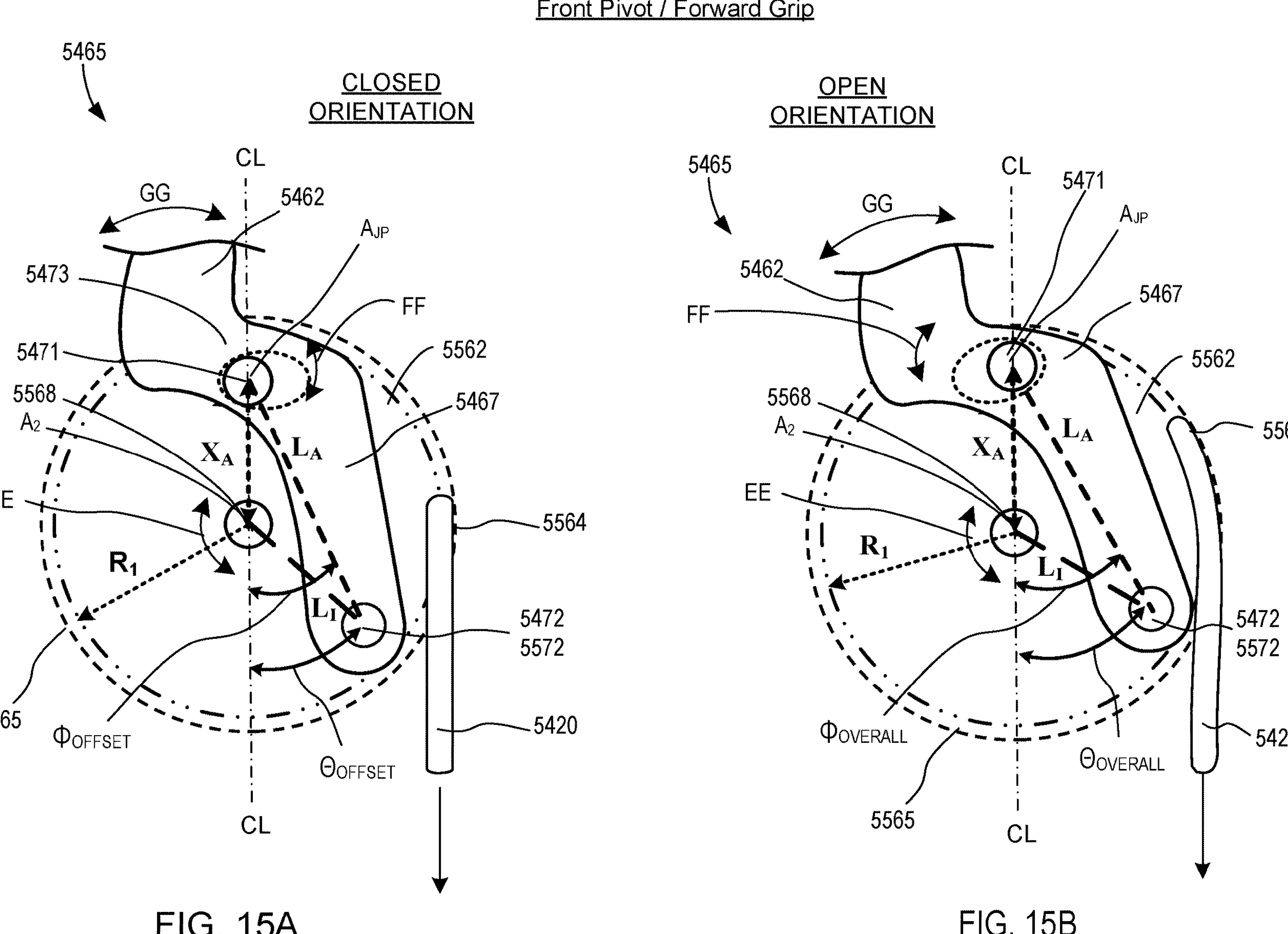
FIGS. 15A and 15B are side views of a tool assembly according to an embodiment having a front pivot/forward grip topology, shown in a first (closed) configuration (FIG. 15A) and a second (open) configuration (FIG. 15B).
Figure 16:
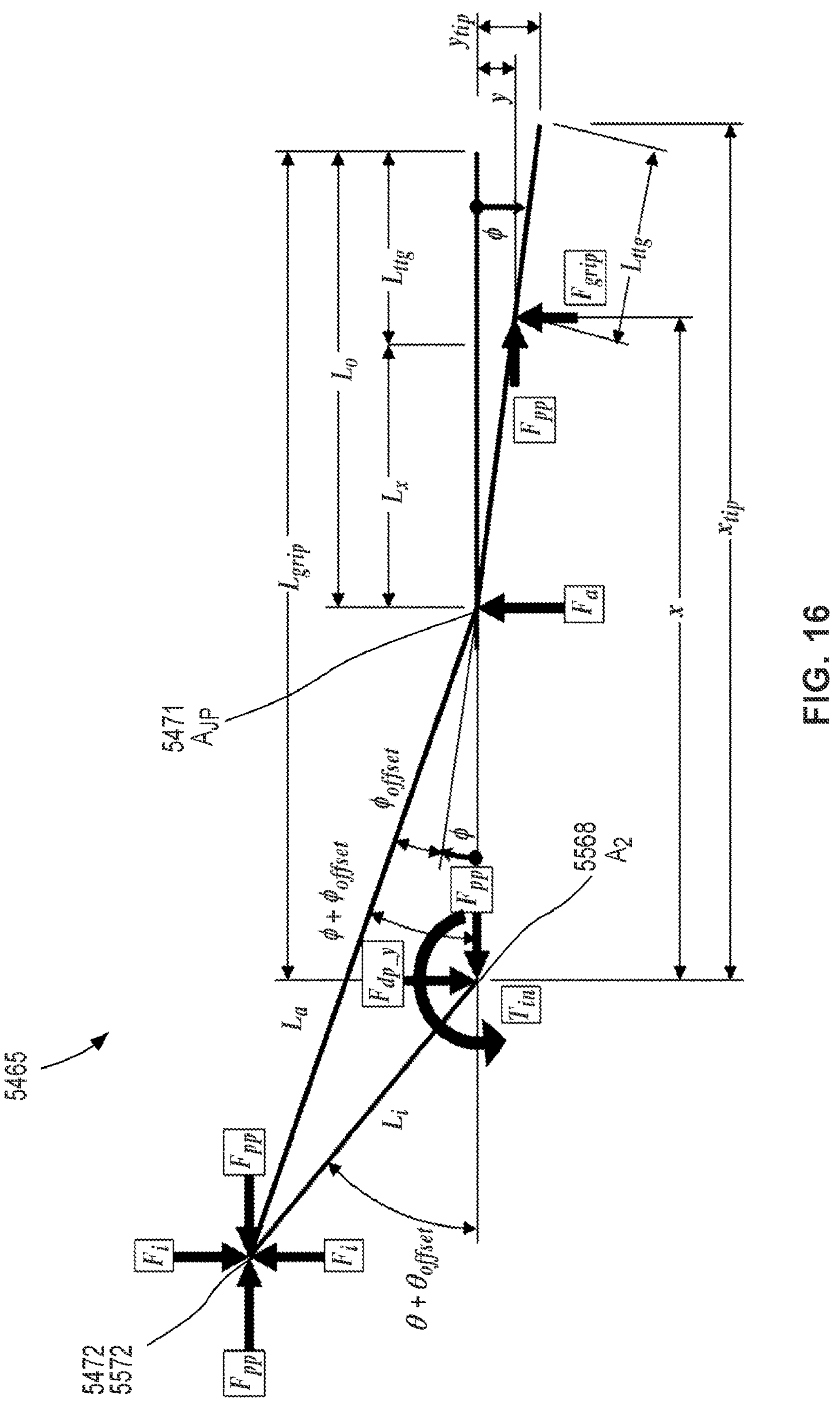
FIG. 16 is a free-body diagram of the tool assembly shown in FIGS. 15A and 15B showing the forces and torques acting on various joint of the tool assembly.

FIGS. 15A, 15B, and 16 are schematic illustrations of a distal end portion of a tool assembly 5465 of an end effector having a front pivot and forward grip topology, according to an embodiment. Specifically, FIGS. 15A and 15B are enlarged side views of a portion of the tool assembly 5465 when the end effector is in a first (closed) configuration (FIG. 15A) and a second (open) configuration (FIG. 15B). FIG. 16 is a free-body diagram showing the forces and torques acting on various joint of the tool assembly 5465. The tool assembly 5465 can be incorporated within any of the end effectors or medical instruments described herein, and can be configured the same or similar to, and function the same or similar to, other tool assemblies described herein. For example, the tool assembly 5465 can be a first tool assembly of an end effector that includes a second tool assembly, similar to the end effector 4460 described above. Thus, certain aspects of the tool assembly 5465 and the end effector in which the tool assembly 5465 is included are not described in detail below, but rather are understood to be similar to aspects of the end effectors (e.g., the end effector 4460) described herein. For example, although FIGS. 15A, 15B, and 16 do not show a clevis, it is understood that the tool assembly 5465 can be rotatably coupled to a central axis $A_2$ of a clevis (similar to the clevis 4610 or any other clevis as shown herein).

The tool assembly 5465 includes a jaw 5462 coupled to a pulley 5562. Like the jaw 4462, the jaw 5462 includes a distal portion and a proximal portion 5467. The proximal portion 5467 includes a pulley connector 5472, which couples the jaw 5462 to and transfers forces from its mating pulley 5562. Additionally, the proximal portion 5467 of the jaw 5462 is rotatably coupled to the proximal portion of a second jaw (not shown) by a jaw pivot pin 5471, which defines a jaw pivot axis $A_{JP}$. The distal portions of the two jaws function as grip portions to cooperatively contact tissue, grasp a needle, or perform other operations, as shown and described above with reference to the jaws 4462 and 4482.

The pulley 5562 is a disk-shaped member that is rotatably coupled to the clevis (not shown) about the central axis $A_2$. The pulley 5562 includes an input connector 5564 and an output connector 5572, and defines a central opening 5568 and a jaw pivot opening (not identified, but that can be similar to the jaw pivot opening 2569 described above). A central pin can be coupled within the central opening 5568 to allow the pulley 5562 and a second pulley (of a second tool assembly, not shown) to rotate relative to the clevis about the central axis $A_2$, as shown by the arrow EE. A cable 5420 is coupled to the pulley 5562 at the input connector 5564. Referring to FIGS. 15A and 15B, the cable 5420 is coupled to the pulley 5562 at a first input radius $R_1$ from the central axis $A_2$. Thus, when an input pulley force is applied by the cable 5420 onto the pulley 5562, an input torque $T_{in}$ is produced about the central axis $A_2$ to rotate the pulley 5562, as shown by the arrow EE. Additionally, the pulley 5562 defines a pulley envelope 5565 as the cylindrical volume about the central axis $A_2$ that has an envelope radius equal to the outer-most radius of the pulley 5562. In some embodiments, the pulley envelope 5565 has an envelope radius equal to the first input radius $R_1$. In some embodiments, the pulley envelope 5565 is the same as a pulley envelope defined by the second pulley.

The output connector 5572 can be any suitable connector or mechanism that couples the jaw 5462 to the pulley 5562 to transfer forces from the pulley 5562 to the jaw 5462. Referring to FIGS. 15A and 15B, the output connector 5572 is radially offset from the central axis $A_2$ by a jaw input length, identified as $L_1$. Thus, the coupling between the pulley 5562 and the jaw 5462 defines a kinematic input link identified as $L_1$ that rotates about the central axis $A_2$. The input link $L_1$ and the end effector center line CL form an input link angle that changes when the pulley 5562 rotates about the central axis $A_2$. When the end effector is in the closed configuration (see FIG. 15A), the input link angle is identified as $\Theta_{OFFSET}$. When the pulley rotates towards the open position (see FIG. 15B), the input link angle increases to a value of $+\Theta_{OFFSET}$ (also referred to as $\Theta_{OVERALL}$). As described in more detail below, the value of $\Theta_{OFFSET}$ can be selected to minimize the impact of the push-pull force Fpp on the grip force Fgrip. For example, in some embodiments, the value of $\Theta_{OFFSET}$ can be less than about 5 degrees. In some embodiments, the value of $\Theta_{OFFSET}$ can be about zero degrees. Similarly stated, in some embodiments, the coupling between the pulley 5562 and the jaw 5462 is along the end effector center line CL when the end effector is in the closed configuration. As shown, the output connector 5572 and the kinematic link $L_1$ are within the pulley envelope 5565. Similarly stated, the jaw input length $L_1$ is less than or equal to the to the first input radius $R_1$.

The proximal portion 5467 of the jaw 5462 includes the pulley connector 5472, which couples the jaw 5462 to and transfers forces from the pulley 5562. Thus, when the input torque $T_{in}$ applied to the pulley 5562 by the cable 5420 is transferred to the jaw 5462, the jaw 5462 rotates relative to the second jaw (and also the clevis; not shown) about the jaw pivot axis $A_{JP}$, as shown by the arrow GG. The jaw pivot axis $A_{JP}$ is offset from the central axis $A_2$ along an end effector center line CL, which is defined between (and normal to) the central axis $A_2$ and the jaw pivot axis $A_{JP}$ when the end effector is in its closed configuration. The offset distance between the jaw pivot axis $A_{JP}$ and the central axis $A_2$ is indicated as $X_A$. The jaw pivot axis $A_{JP}$ is also offset from the pulley connector 5472 by a jaw applied length, identified as $L_A$. Thus, the coupling of the jaws at the jaw pivot pin 5471 and the coupling of the jaw 5462 and the pulley 5562 at the pulley connector 5472 define a kinematic applied link identified as $L_A$ that rotates about the jaw pivot axis $A_{JP}$. The applied input link $L_A$ and the end effector center line CL form an applied link angle that changes when the jaw 5462 rotates about the central axis $A_2$ and the jaw pivot axis $A_{JP}$. When the end effector is in the closed configuration (see FIG. 15A), the input link angle is identified as $\Phi_{OFFSET}$. When the pulley rotates towards the open position (see FIGS. 15B and 16), the applied link angle increases to a value of $\Phi+\Phi_{OFFSET}$ (also referred to as $\Phi_{OVERALL}$). As shown, the jaw pivot axis $A_{JP}$ and the kinematic link $L_A$ are within the pulley envelope 5565.

As mentioned above, the pulley 5562 and a second pulley (not shown) each define a jaw pivot opening (similar to the jaw pivot openings 2569 and 2589 described above) through which the jaw pivot pin 5471 extends. More particularly, the jaw pivot openings are elongated to allow movement of the jaw pivot pin 5471 relative to the pulleys during operation (e.g., during relative motion between the jaws and the pulleys). Thus, in certain configurations (e.g., fully opened), the walls of the pulleys can limit the movement of the jaw pivot pin 5471. Specifically, as shown in FIGS. 15A and 15B, as the jaws rotate relative to the pulleys rotate, the movement of the jaw pivot pin 5471 occurs within a jaw pivot pin envelope 5473.

As shown, the tool assembly 5465 has a front pivot topology. Specifically, the central axis $A_2$ is further from the jaw tip than is the jaw pivot axis $A_{JP}$. Said another way, the jaw pivot axis $A_{JP}$ is between the central axis $A_2$ and the distal end (or grip portion) of the jaw 5462. Additionally, like the tool assembly 4465 described above, the tool assembly 5465 has a forward grip topology. Specifically, when the pulleys rotate to move the end effector from the closed configuration (FIG. 15A) to an opened configuration (FIG. 15B), the input link angle Θ increases.

In use, the end effector can amplify the input pulley force $F_P$ to produce a higher grip force Fgrip produced by the jaws than would be produced with a standard single-piece jaw and pulley system. Specifically, the arrangement of the input link $L_1$ (including the input link angle $\Theta_{OFFSET}$) and the applied link $L_A$, together with the range of lengths of the jaws can amplify the grip force Fgrip. FIG. 16 provides a free-body diagram showing the geometry of the tool assembly 5465 when the end effector is in an opened position. Considering the input link $L_1$ in isolation, the moment balance taken around the central axis $A_2$ is provided by Equation (8), which can be reduced produce Equation (9) and Equation (10) for the resultant forces, at the central axis $A_2$.

$$\sum M_{dp} = T_{in} - F_i \cdot \cos(\theta + \theta_{offset}) \cdot L_i - F_{pp} \cdot \sin(\theta + \theta_{offset}) \cdot L_i = 0 \quad \text{Eq (8)}$$

$$F_i = \frac{T_{in}}{\cos(\theta + \theta_{offset}) \cdot L_i} - F_{pp} \cdot \tan(\theta + \theta_{offset}) \quad \text{Eq (9)}$$

$$F_{dp} = \frac{T_{in}}{\cos(\theta + \theta_{offset}) \cdot L_i} - F_{pp} \cdot \tan(\theta + \theta_{offset}) \quad \text{Eq (10)}$$

Considering the applied link $L_A$ in isolation, the moment balance taken around the jaw pivot axis $A_{JP}$ is provided by Equation (11). Reducing this equation (including substituting the expression for $F_1$) produces Equation (12) for the grip force Fgrip. As shown by Equation (12), the grip force Fgrip includes a component based on the input torque $T_{in}$ and the push-pull force Fpp.

$$\sum M_a = -F_i \cdot \cos(\phi + \phi_{offset}) \cdot L_a + F_{pp} \cdot \sin(\phi + \phi_{offset}) \cdot L_a + F_{pp} \cdot \sin(\phi) \cdot (L_o - L_{ttg}) + F_{grip} \cdot \cos(\phi) \cdot (L_o - L_{ttg}) = 0 \quad \text{Eq (11)}$$

$$F_{grip} = T_{in} \cdot \frac{L_a}{L_i} \cdot \frac{1}{(L_o - L_{ttg})} \cdot \frac{1}{\cos(\phi)} \frac{\sqrt{1 - \left(\sin(\theta + \theta_{offset}) \cdot \frac{L_i}{L_a}\right)^2}}{\cos(\theta + \theta_{offset})} + F_{pp} \cdot \left( \frac{\tan(\theta + \theta_{offset}) \cdot \sqrt{L_a^2 - (\sin(\theta + \theta_{offset}) \cdot L_i)^2}}{\cos(\phi) \cdot (L_o - L_{ttg})} - \frac{\sin(\theta + \theta_{offset}) \cdot L_i}{\cos(\phi) \cdot (L_o - L_{ttg})} - \tan(\phi) \cdot (L_o - L_{ttg}) \right) \quad \text{Eq (12)}$$

If no push-pull force is present (i.e., Fpp=0), the grip force Fgrip is given by Equation (13). As indicated, the grip force increases with increasing angle. Additionally, if the input link angle Θ is set to zero, when the end effector is closed, the push-pull force Fpp has no effect on the grip force Fgrip (see Equation (14)).

$$F_{grip} = T_{in} \cdot \frac{L_a}{L_i} \cdot \frac{1}{(L_o - L_{ttg})} \cdot \frac{1}{\cos(\phi)} \cdot \frac{\sqrt{1 - \left(\sin(\theta + \theta_{offset}) \cdot \frac{L_i}{L_a}\right)^2}}{\cos(\theta + \theta_{offset})} \quad \text{Eq (13)}$$

$$F_{grip} = T_{in} \cdot \frac{L_a}{L_i} \cdot \frac{1}{(L_o - L_{ttg})} \quad \text{Eq (14)}$$

Figure 18:
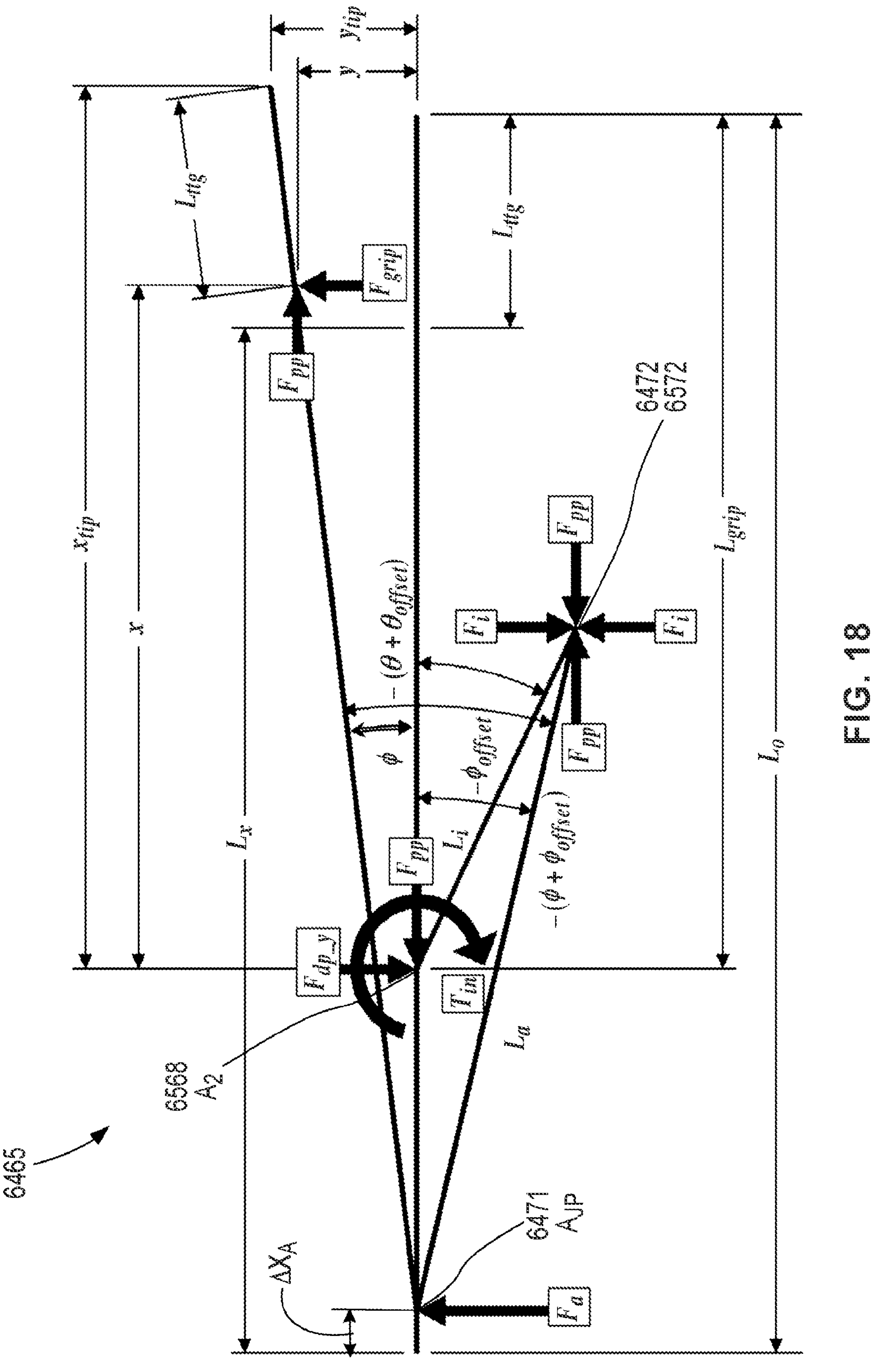
FIG. 18 is a free-body diagram of the tool assembly shown in FIGS. 17A and 17B showing the forces and torques acting on various joint of the tool assembly.

FIGS. 17A, 17B, and 18 are schematic illustration of a distal end portion of a tool assembly 6465 of an end effector having a rear pivot and reverse grip topology, according to an embodiment. Specifically, FIGS. 17A and 17B are enlarged side views of a portion of the tool assembly 6465 when the end effector is in a first (closed) configuration (FIG. 17A) and a second (open) configuration (FIG. 17B). FIG. 18 is a free-body diagram showing the forces and torques acting on various joint of the tool assembly 6465. The tool assembly 6465 can be incorporated within any of the end effectors or medical instruments described herein, and can be configured the same or similar to, and function the same or similar to, other tool assemblies described herein. For example, the tool assembly 6465 can be a first tool assembly of an end effector that includes a second tool assembly, similar to the end effector 4460 described above. Thus, certain aspects of the tool assembly 6465 and the end effector in which the tool assembly 6465 is included are not described in detail below, but rather are understood to be similar to aspects of the end effectors (e.g., the end effector 4460) described herein. For example, although FIGS. 17A, 17B, and 18 do not show a clevis, it is understood that the tool assembly 6465 can be rotatably coupled to a central axis $A_2$ of a clevis (similar to the clevis 4610 or any other clevis as shown herein).

The tool assembly 6465 includes a jaw 6462 coupled to a pulley 6562. Like the jaw 4462, the jaw 6462 includes a distal portion and a proximal portion 6467. The proximal portion 6467 includes a pulley connector 6472, which couples the jaw 6462 to and transfers forces from its mating pulley 6562. Additionally, the proximal portion 6467 of the jaw 6462 is rotatably coupled to the proximal portion of a second jaw (not shown) by a jaw pivot pin 6471, which defines a jaw pivot axis $A_{JP}$. The distal portions of the two jaws function as grip portions to cooperatively contact tissue, grasp a needle, or perform other operations, as shown and described above with reference to the jaws 4462 and 4482.

The pulley 6562 is a disk-shaped member that is rotatably coupled to the clevis (not shown) about the central axis $A_2$. The pulley 6562 includes an input connector 6564 and an output connector 6572, and defines a central opening 6568 and a jaw pivot opening (not identified, but that can be similar to the jaw pivot opening 2569 described above). A central pin can be coupled within the central opening 6568 to allow the pulley 6562 and a second pulley (of a second tool assembly, not shown) to rotate relative to the clevis about the central axis $A_2$, as shown by the arrow EE. A cable 6420 is coupled to the pulley 6562 at the input connector 6564. Referring to FIGS. 17A and 17B, the cable 6420 is coupled to the pulley 6562 at a first input radius $R_1$ from the central axis $A_2$. Thus, when an input pulley force is applied by the cable 6420 onto the pulley 6562, an input torque $T_{in}$ is produced about the central axis $A_2$ to rotate the pulley 6562, as shown by the arrow EE. Additionally, the pulley 6562 defines a pulley envelope 6565 as the cylindrical volume about the central axis $A_2$ that has an envelope radius equal to the outer-most radius of the pulley 6562. In some embodiments, the pulley envelope 6565 has an envelope radius equal to the first input radius $R_1$.

The output connector 6572 can be any suitable connector or mechanism that couples the jaw 6462 to the pulley 6562 to transfer forces from the pulley 6562 to the jaw 6462. Referring to FIGS. 17A and 17B, the output connector 6572 is radially offset from the central axis $A_2$ by a jaw input length, identified as $L_1$. Thus, the coupling between the pulley 6562 and the jaw 6462 defines a kinematic input link identified as $L_1$ that rotates about the central axis $A_2$. The input link $L_1$ and the end effector center line CL form an input link angle that changes when the pulley 6562 rotates about the central axis $A_2$. When the end effector is in the closed configuration (see FIG. 17A), the input link angle is identified as $\Theta_{OFFSET}$. When the pulley rotates towards the open position (see FIG. 17B), the input link angle increases to a value of $+\Theta_{OFFSET}$ (also referred to as $\Theta_{OVERALL}$). As described in more detail below, the value of $\Theta_{OFFSET}$ can be selected to minimize the impact of the push-pull force Fpp on the grip force Fgrip. For example, in some embodiments, the value of $\Theta_{OFFSET}$ can be less than about 5 degrees. In some embodiments, the value of $\Theta_{OFFSET}$ can be about zero degrees. Similarly stated, in some embodiments, the coupling between the pulley 6562 and the jaw 6462 is along the end effector center line CL when the end effector is in the closed configuration. As shown, the output connector 6572 and the kinematic link $L_1$ are within the pulley envelope 6565. Similarly stated, the jaw input length $L_1$ is less than or equal to the to the first input radius $R_1$.

The proximal portion 6467 of the jaw 6462 includes the pulley connector 6472, which couples the jaw 6462 to and transfers forces from the pulley 6562. Thus, when the input torque $T_{in}$ applied to the pulley 6562 by the cable 6420 is transferred to the jaw 6462, the jaw 6462 rotates relative to the second jaw (and also the clevis; not shown) about the jaw pivot axis $A_{JP}$, as shown by the arrow GG. The jaw pivot axis $A_{JP}$ is offset from the central axis $A_2$ along an end effector center line CL, which is defined between (and normal to) the central axis $A_2$ and the jaw pivot axis $A_{JP}$ when the end effector is in its closed configuration. The offset distance between the jaw pivot axis $A_{JP}$ and the central axis $A_2$ is indicated as $X_A$. The jaw pivot axis $A_{JP}$ is also offset from the pulley connector 6472 by a jaw applied length, identified as $L_A$. Thus, the coupling of the jaws at the jaw pivot pin 6471 and the coupling of the jaw 6462 and the pulley 6562 at the pulley connector 6472 define a kinematic applied link identified as $L_A$ that rotates about the jaw pivot axis $A_{JP}$. The applied input link $L_A$ and the end effector center line CL form an applied link angle that changes when the jaw 6462 rotates about the central axis $A_2$ and the jaw pivot axis $A_{JP}$. When the end effector is in the closed configuration (see FIG. 17A), the input link angle is identified as a/OFFSET. When the pulley rotates towards the open position (see FIGS. 17B and 18), the applied link angle increases to a value of $\Phi+\Phi_{OFFSET}$ (also referred to as $\Phi_{OVERALL}$). As shown, the jaw pivot axis $A_{JP}$ and the kinematic link $L_A$ are within the pulley envelope 6565.

As mentioned above, the pulley 6562 and a second pulley (not shown) each define a jaw pivot opening (similar to the jaw pivot openings 2569 and 2589 described above) through which the jaw pivot pin 6471 extends. More particularly, the jaw pivot openings are elongated to allow movement of the jaw pivot pin 6471 relative to the pulleys during operation (e.g., during relative motion between the jaws and the pulleys). Thus, in certain configurations (e.g., fully opened), the walls of the pulleys can limit the movement of the jaw pivot pin 6471. Specifically, as shown in FIGS. 17A and 17B, as the jaws rotate relative to the pulleys rotate, the movement of the jaw pivot pin 6471 occurs within a jaw pivot pin envelope 6473.

As shown, the tool assembly 6465 has a rear pivot topology. Specifically, the jaw pivot axis $A_{JP}$ is further from the jaw tip than is the central axis $A_2$. Said another way, the central axis $A_2$ is between the jaw pivot axis $A_{JP}$ and the distal end (or grip portion) of the jaw 6462. Additionally, in contrast to the tool assemblies 4465 and 5465, the tool assembly 6465 has a reverse grip topology. Specifically, when the pulleys rotate to move the end effector from the closed configuration (FIG. 17A) to an opened configuration (FIG. 17B), the input link angle $\Theta$ decreases.

In use, the end effector can amplify the input pulley force $F_P$ to produce a higher grip force Fgrip produced by the jaws than would be produced with a standard single-piece jaw and pulley system. Specifically, the arrangement of the input link $L_1$ (including the input link angle $\Phi_{OFFSET}$) and the applied link $L_A$, together with the range of lengths of the jaws can amplify the grip force Fgrip. FIG. 18 provides a free-body diagram showing the geometry of the tool assembly 6465 when the end effector is in an opened position. Considering the input link $L_1$ in isolation, the moment balance taken around the central axis $A_2$ is provided by Equation (15), which can be reduced produce Equation (16) and Equation (17) for the resultant forces, at the central axis $A_2$.

$$\sum M_{dp} = -T_{in} + F_i \cdot \cos(\theta + \theta_{offset}) \cdot L_i + F_{pp} \cdot \sin(-(\theta + \theta_{offset})) \cdot L_i = 0 \quad \text{Eq (15)}$$

$$F_i = \frac{T_{in}}{\cos(\theta + \theta_{offset}) \cdot L_i} + F_{pp} \cdot \tan(\theta + \theta_{offset}) \quad \text{Eq (16)}$$

$$F_{dp} = \frac{T_{in}}{\cos(\theta + \theta_{offset}) \cdot L_i} + F_{pp} \cdot \tan(\theta + \theta_{offset}) \quad \text{Eq (17)}$$

Considering the applied link $L_A$ in isolation, the moment balance taken around the jaw pivot axis $A_{JP}$ is provided by Equation (18). Reducing this equation (including substituting the expression for $F_1$) produces Equation (19) for the grip force Fgrip. As shown by Equation (19), the grip force Fgrip includes a component based on the input torque $T_{in}$ and the push-pull force Fpp.

$$\sum M_a = -F_i \cdot \cos(-(\phi + \phi_{offset})) \cdot L_a + F_{pp} \cdot \sin(-(\phi + \phi_{offset})) \cdot L_a - F_{pp} \cdot \sin(\phi) \cdot (L_o - L_{ttg}) + F_{grip} \cdot \cos(\phi) \cdot (L_o - L_{ttg}) = 0 \quad \text{Eq (18)}$$

$$F_{grip} = T_{in} \cdot \frac{L_a}{L_i} \cdot \frac{1}{(L_o - L_{ttg})} \cdot \frac{1}{\cos(\phi)} \frac{\sqrt{1 - \left(\sin(\theta + \theta_{offset}) \cdot \frac{L_i}{L_a}\right)^2}}{\cos(\theta + \theta_{offset})} + F_{pp} \cdot \left( \frac{\tan(\theta + \theta_{offset}) \cdot \sqrt{L_a^2 - (\sin(\theta + \theta_{offset}) \cdot L_i)^2}}{\cos(\phi) \cdot (L_o - L_{ttg})} - \frac{\sin(\theta + \theta_{offset}) \cdot L_i}{\cos(\phi) \cdot (L_o - L_{ttg})} + \tan(\phi) \cdot (L_o - L_{ttg}) \right) \quad \text{Eq (19)}$$

If no push-pull force is present (i.e., Fpp=0), the grip force Fgrip is given by Equation (20). As indicated, the grip force increases with increasing angle. Additionally, if the input link angle $\Theta$ is set to zero, when the end effector is closed, the push-pull force Fpp has no effect on the grip force Fgrip (see Equation (14)).

$$F_{grip} = T_{in} \cdot \frac{L_a}{L_i} \cdot \frac{1}{(L_o - L_{ttg})} \cdot \frac{1}{\cos(\phi)} \cdot \frac{\sqrt{1 - \left(\sin(\theta + \theta_{offset}) \cdot \frac{L_i}{L_a}\right)^2}}{\cos(\theta + \theta_{offset})} \quad \text{Eq (20)}$$

$$F_{grip} = T_{in} \cdot \frac{L_a}{L_i} \cdot \frac{1}{(L_o - L_{ttg})} \quad \text{Eq (21)}$$

Figures 19A, 19B:
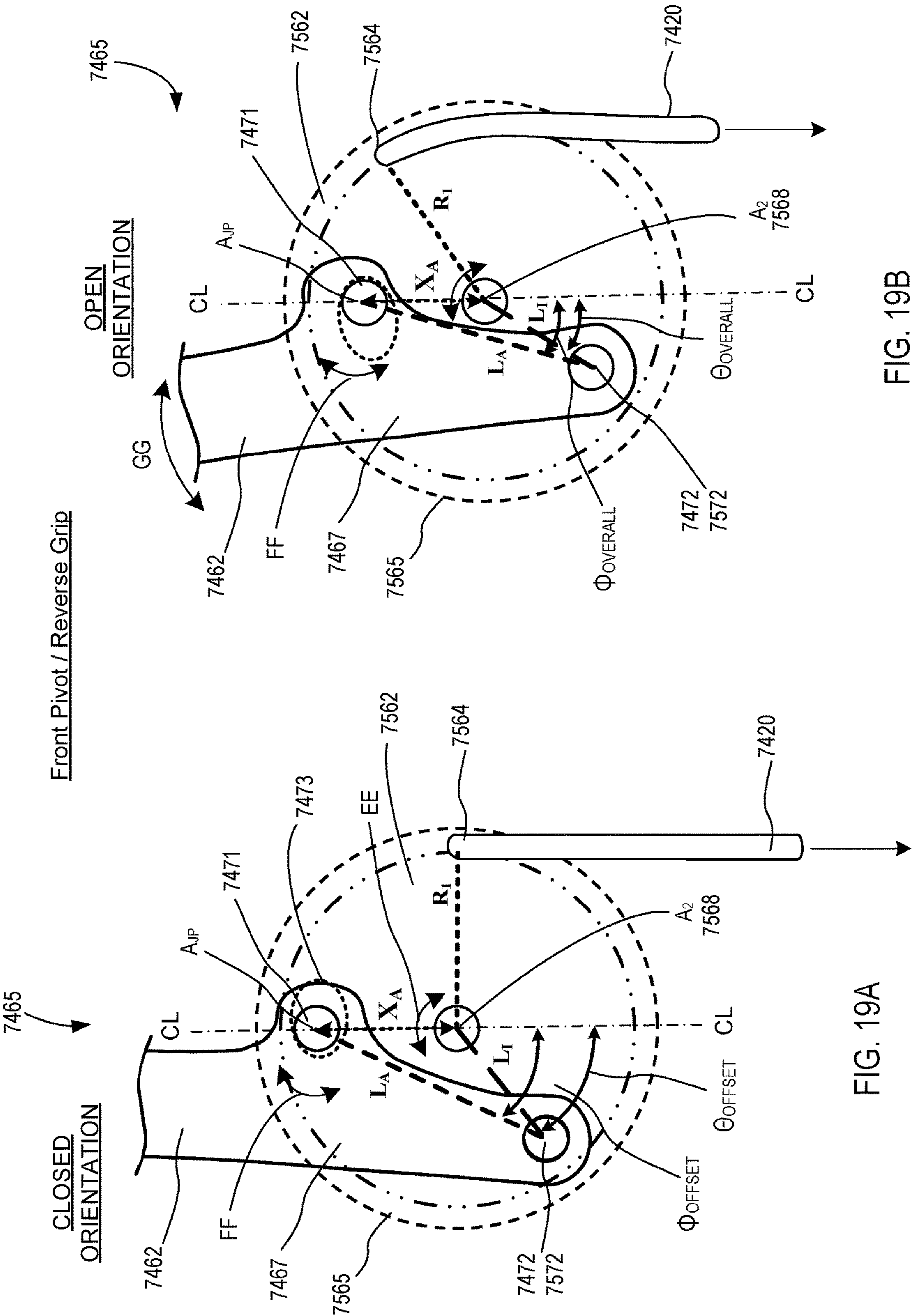
FIGS. 19A and 19B are side views of a tool assembly according to an embodiment having a front pivot/reverse grip topology, shown in a first (closed) configuration (FIG. 19A) and a second (open) configuration (FIG. 19B).
Figure 20:
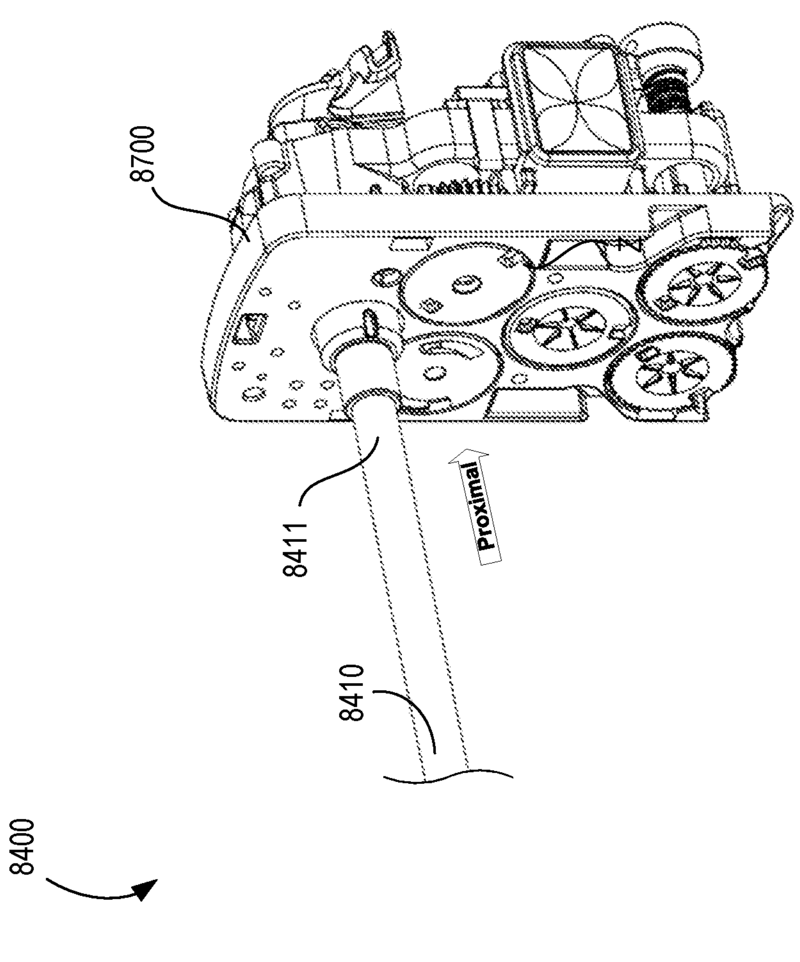
FIG. 20 is a perspective view of an instrument of a surgery system in a first configuration.
Figure 20:
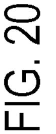
Figure 20:
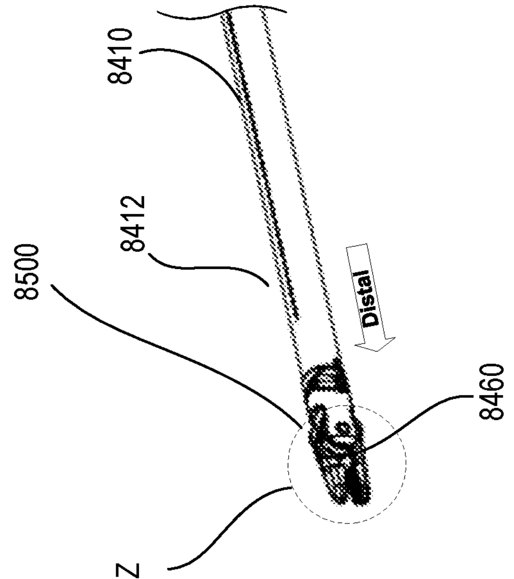

FIGS. 19A and 19B are schematic illustrations of a distal end portion of a tool assembly 7465 of an end effector having a front pivot and reverse grip topology, according to an embodiment. Specifically, FIGS. 19A and 19B are enlarged side views of a portion of the tool assembly 7465 when the end effector is in a first (closed) configuration (FIG. 19A) and a second (open) configuration (FIG. 19B). The tool assembly 7465 can be incorporated within any of the end effectors or medical instruments described herein, and can be configured the same or similar to, and function the same or similar to, other tool assemblies described herein. For example, the tool assembly 7465 can be a first tool assembly of an end effector that includes a second tool assembly, similar to the end effector 4460 described above. Thus, certain aspects of the tool assembly 7465 and the end effector in which the tool assembly 7465 is included are not described in detail below, but rather are understood to be similar to aspects of the end effectors (e.g., the end effector 4460) described herein. For example, although FIGS. 19A and 19B do not show a clevis, it is understood that the tool assembly 7465 can be rotatably coupled to a central axis $A_2$ of a clevis (similar to the clevis 4610 or any other clevis as shown herein).

The tool assembly 7465 includes a jaw 7462 coupled to a pulley 7562. Like the jaw 4462, the jaw 7462 includes a distal portion and a proximal portion 7467. The proximal portion 7467 includes a pulley connector 7472, which couples the jaw 7462 to and transfers forces from its mating pulley 7562. Additionally, the proximal portion 7467 of the jaw 7462 is rotatably coupled to the proximal portion of a second jaw (not shown) by a jaw pivot pin 7471, which defines a jaw pivot axis $A_{JP}$. The distal portions of the two jaws function as grip portions to cooperatively contact tissue, grasp a needle, or perform other operations, as shown and described above with reference to the jaws 4462 and 4482.

The pulley 7562 is a disk-shaped member that is rotatably coupled to the clevis (not shown) about the central axis $A_2$. The pulley 7562 includes an input connector 7564 and an output connector 7572, and defines a central opening 7568 and a jaw pivot opening (not identified, but that can be similar to the jaw pivot opening 2569 described above). A central pin can be coupled within the central opening 7568 to allow the pulley 7562 and a second pulley (of a second tool assembly, not shown) to rotate relative to the clevis about the central axis $A_2$, as shown by the arrow EE. A cable 7420 is coupled to the pulley 7562 at the input connector 7564. Referring to FIGS. 15A and 15B, the cable 7420 is coupled to the pulley 7562 at a first input radius $R_1$ from the central axis $A_2$. Thus, when an input pulley force is applied by the cable 7420 onto the pulley 7562, an input torque $T_{in}$ is produced about the central axis $A_2$ to rotate the pulley 7562, as shown by the arrow EE. Additionally, the pulley 7562 defines a pulley envelope 7565 as the cylindrical volume about the central axis $A_2$ that has an envelope radius equal to the outer-most radius of the pulley 7562.

The output connector 7572 can be any suitable connector or mechanism that couples the jaw 7462 to the pulley 7562 to transfer forces from the pulley 7562 to the jaw 7462. The output connector 7572 is radially offset from the central axis $A_2$ by a jaw input length, identified as $L_1$. Thus, the coupling between the pulley 7562 and the jaw 7462 defines a kinematic input link identified as $L_1$ that rotates about the central axis $A_2$. The input link $L_1$ and the end effector center line CL form an input link angle that changes when the pulley 7562 rotates about the central axis $A_2$. When the end effector is in the closed configuration (see FIG. 19A), the input link angle is identified as $\Theta_{OFFSET}$. When the pulley rotates towards the open position (see FIG. 19B), the input link angle increases to a value of $\Theta+\Theta_{OFFSET}$ (also referred to as $\Theta_{OVERALL}$). As described in more detail below, the value of $\Theta_{OFFSET}$ can be selected to minimize the impact of the push-pull force Fpp on the grip force Fgrip. For example, in some embodiments, the value of $\Theta_{OFFSET}$ can be less than about 5 degrees. In some embodiments, the value of $\Theta_{OFFSET}$ can be about zero degrees. Similarly stated, in some embodiments, the coupling between the pulley 7562 and the jaw 7462 is along the end effector center line CL when the end effector is in the closed configuration. As shown, the output connector 7572 and the kinematic link $L_1$ are within the pulley envelope 7565. Similarly stated, the jaw input length $L_1$ is less than or equal to the to the first input radius $R_1$.

The proximal portion 7467 of the jaw 7462 includes the pulley connector 7472, which couples the jaw 7462 to and transfers forces from the pulley 7562. Thus, when the input torque $T_{in}$ applied to the pulley 7562 by the cable 7420 is transferred to the jaw 7462, the jaw 7462 rotates relative to the second jaw (and also the clevis; not shown) about the jaw pivot axis $A_{JP}$, as shown by the arrow GG. The jaw pivot axis $A_{JP}$ is offset from the central axis $A_2$ along an end effector center line CL, which is defined between (and normal to) the central axis $A_2$ and the jaw pivot axis $A_{JP}$ when the end effector is in its closed configuration. The offset distance between the jaw pivot axis $A_{JP}$ and the central axis $A_2$ is indicated as $X_A$. The jaw pivot axis $A_{JP}$ is also offset from the pulley connector 7472 by a jaw applied length, identified as $L_A$. Thus, the coupling of the jaws at the jaw pivot pin 7471 and the coupling of the jaw 7462 and the pulley 7562 at the pulley connector 7472 define a kinematic applied link identified as $L_A$ that rotates about the jaw pivot axis $A_{JP}$. The applied input link $L_A$ and the end effector center line CL form an applied link angle that changes when the jaw 7462 rotates about the central axis $A_2$ and the jaw pivot axis $A_{JP}$. When the end effector is in the closed configuration (see FIG. 19A), the input link angle is identified as $\Phi_{OFFSET}$. When the pulley rotates towards the open position (see FIG. 19B), the applied link angle increases to a value of $\Phi+\Phi_{OFFSET}$ (also referred to as $\Phi_{OVERALL}$). As shown, the jaw pivot axis $A_{JP}$ and the kinematic link $L_A$ are within the pulley envelope 7565.

As mentioned above, the pulley 7562 and a second pulley (not shown) each define a jaw pivot opening (similar to the jaw pivot openings 2569 and 2589 described above) through which the jaw pivot pin 7471 extends. More particularly, the jaw pivot openings are elongated to allow movement of the jaw pivot pin 7471 relative to the pulleys during operation (e.g., during relative motion between the jaws and the pulleys). Thus, in certain configurations (e.g., fully opened), the walls of the pulleys can limit the movement of the jaw pivot pin 7471. Specifically, as shown in FIGS. 19A and 19B, as the jaws rotate relative to the pulleys rotate, the movement of the jaw pivot pin 7471 occurs within a jaw pivot pin envelope 7473.

As shown, the tool assembly 7465 has a front pivot topology. Specifically, the central axis $A_2$ is further from the jaw tip than is the jaw pivot axis $A_{JP}$. Said another way, the jaw pivot axis $A_{JP}$ is between the central axis $A_2$ and the distal end (or grip portion) of the jaw 7462. Additionally, like the tool assembly 6465 described above, the tool assembly 7465 has a reverse grip topology. Specifically, when the pulleys rotate to move the end effector from the closed configuration (FIG. 19A) to an opened configuration (FIG. 19B), the input link angle Θ decreases. In use, the end effector can amplify the input pulley force $F_P$ to produce a higher grip force Fgrip produced by the jaws than would be produced with a standard single-piece jaw and pulley system, in a similar manner as described herein.

Figure 21:
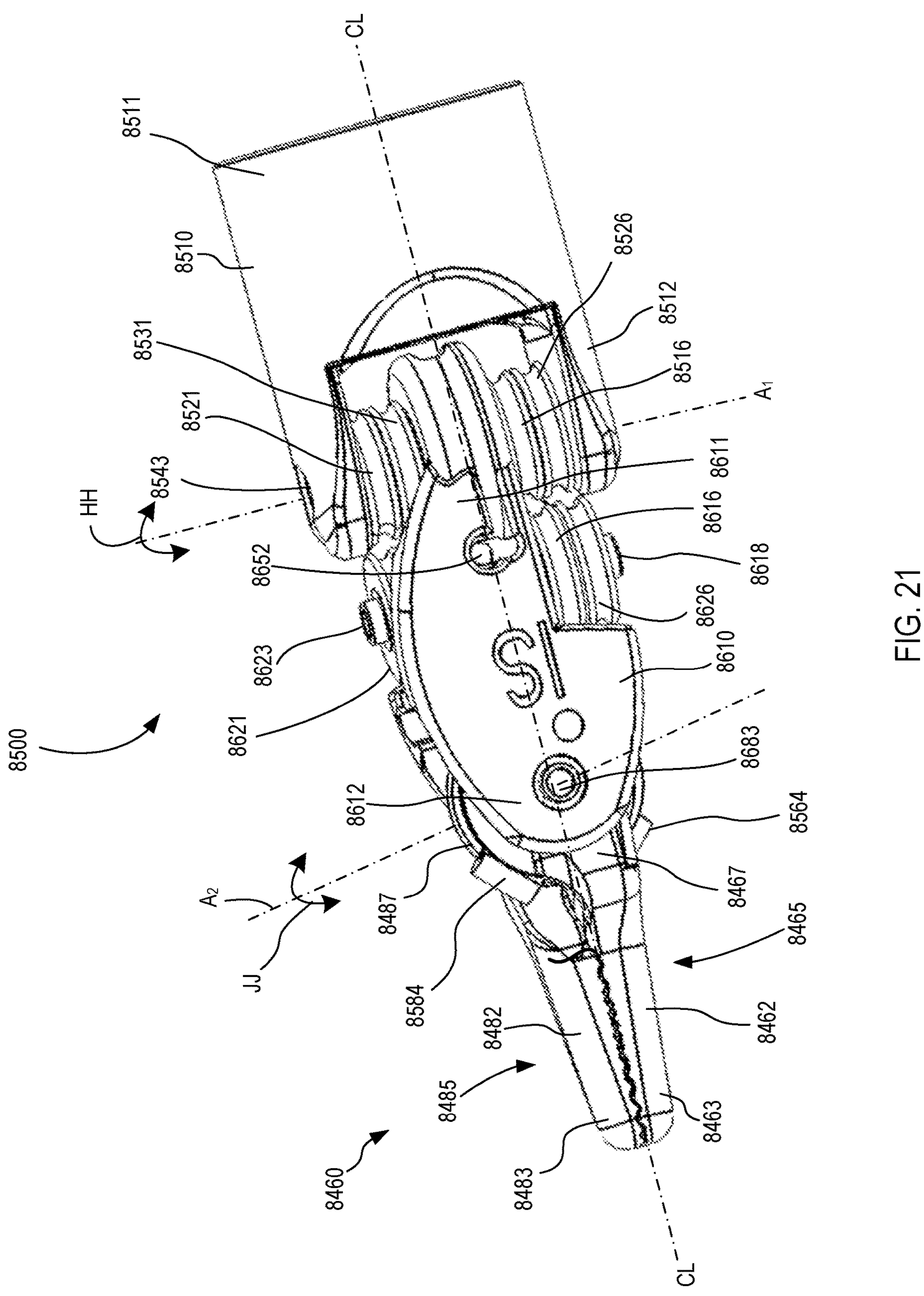
FIG. 21 is an enlarged perspective view of an end effector and wrist assembly of the instrument indicated by the region Z shown in FIG. 20.
Figure 22:
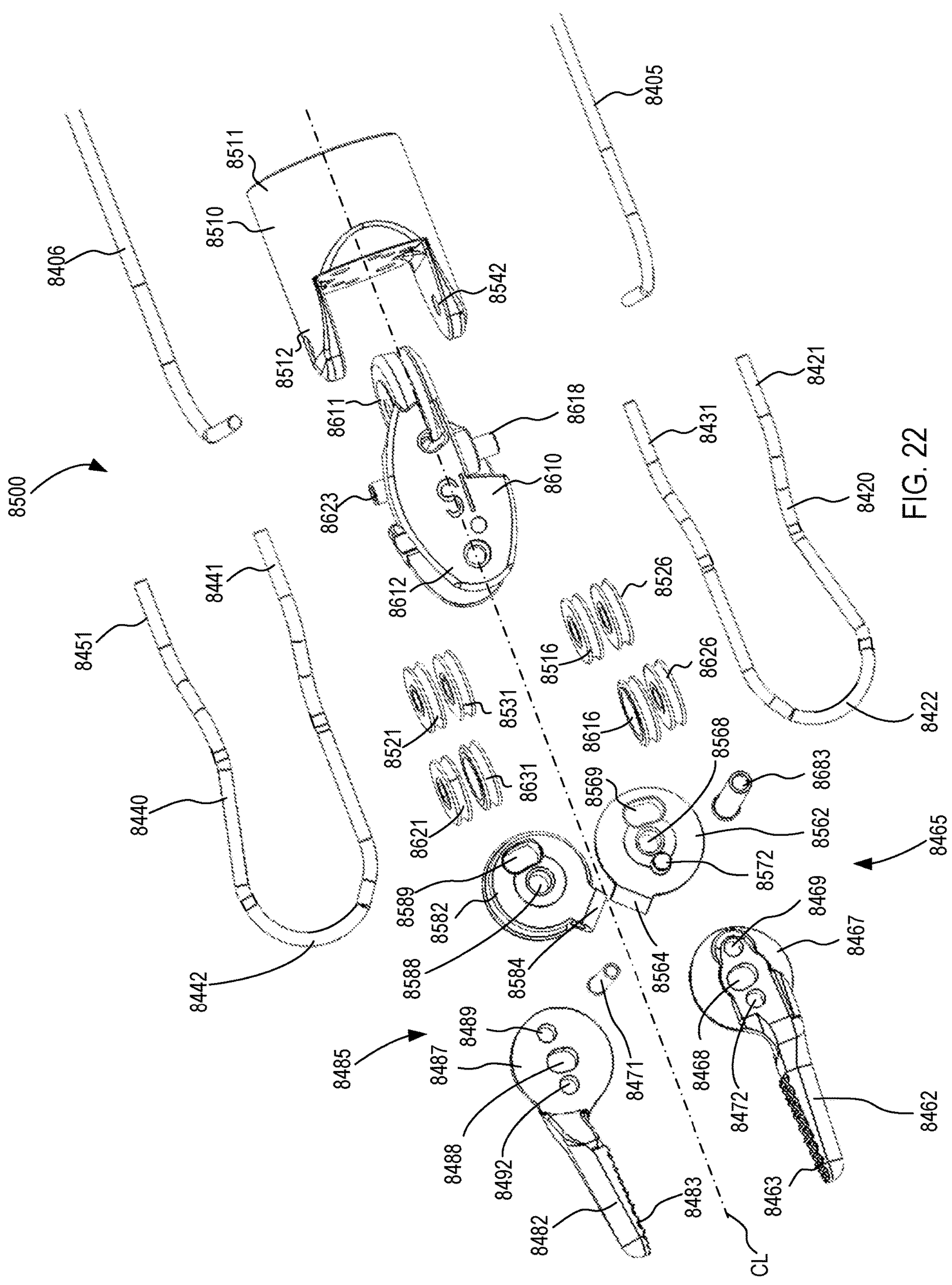
FIG. 22 is an exploded perspective view of the distal end portion of the instrument shown in FIG. 21.
Figure 23:
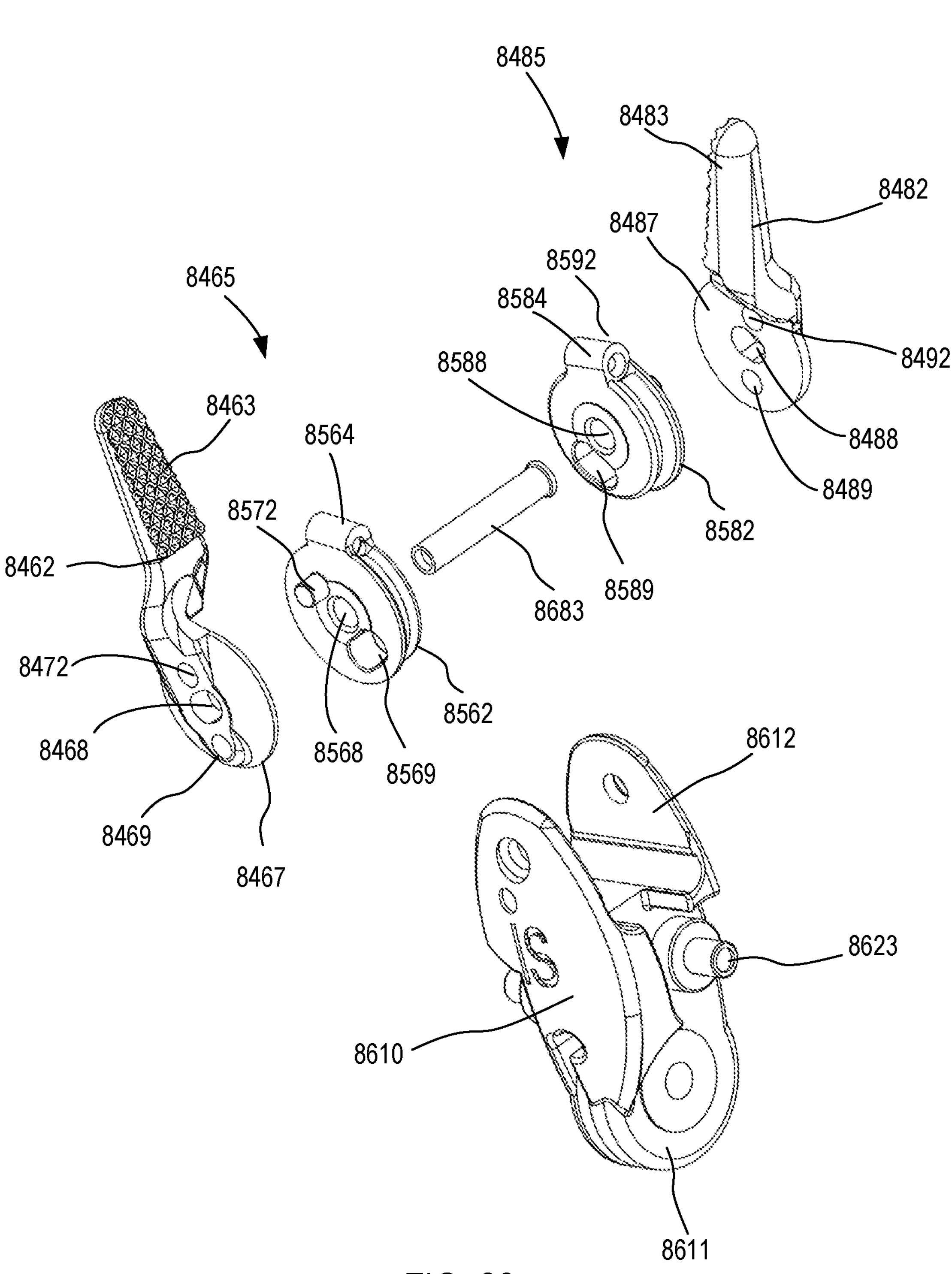
FIG. 23 is an exploded perspective view of the end effector of the instrument shown in FIGS. 20 and 21.

FIGS. 20-28 are various views of an instrument 8400 with an end effector 8460 having a rear pivot and forward grip topology with the pulleys in between the jaws, according to an embodiment. The instrument 8400 or any of the components therein are optionally parts of a surgical system that performs surgical procedures, and which can include a manipulator unit, a series of kinematic linkages, a series of cannulas, or the like. The instrument 8400 (and any of the instruments described herein) can be used in any suitable surgical system, such as the MIRS system 1000 shown and described above. The instrument 8400 includes a mechanical structure 8700, a shaft 8410, a wrist assembly 8500, and an end effector 8460. As shown in FIG. 22, the instrument 8400 also includes a first pitch cable 8405 and a second pitch cable 8406 that couple the mechanical structure 8700 to the distal clevis 8610 of the wrist assembly 8500. The instrument 8400 is configured such that movement of the first pitch cable 8405 and second pitch cable 8406 produces rotation of the wrist assembly 8500 (i.e., pitch rotation; the term pitch is arbitrary) about a first axis of rotation $A_1$ (see the arrow HH in FIG. 21). The instrument 8400 also includes a first cable 8420 and a second cable 8440 that couple the mechanical structure 8700 to the end effector 8460. As shown in FIG. 22, the first cable 8420 forms a cable loop having a first proximal portion 8421, a distal portion 8422, and a second proximal portion 8431. The distal portion 8422 is coupled to the input connector 8564 of the first pulley 8562, as described in more detail below. The first proximal portion 8421 and the second proximal portion 8431 are routed proximally to the mechanical structure 8700. The second cable 8440 forms a cable loop having a first proximal portion 8441, a distal portion 8442, and a second proximal portion 8451. The distal portion 8442 is coupled to the input connector 8584 of the second pulley 8582, as described in more detail below. The first proximal portion 8441 and the second proximal portion 8451 are routed proximally to the mechanical structure 8700. Movement of the first cable 8420 and second cable 8440 produces yaw rotation (the term yaw is arbitrary) of the end effector 8460 about a second axis of rotation $A_2$ (see the arrow JJ in FIG. 21), a gripping rotation of the tool members of the end effector 8460 about the second axis of rotation $A_2$, or any combination of these movements. Specifically, yaw rotation occurs when first cable and second cable are driven in the same direction. In this case then the jaws and pulleys move together as one unit and there is no amplification. Conversely, gripping rotation involves driving the cables in opposite directions. Changing the pitch or yaw of the instrument 8400 can be performed by manipulating the cables (i.e., moving or changing tension in the cables).

The shaft 8410 can be any suitable elongated shaft that couples the wrist assembly 8500 to the mechanical structure 8700. Specifically, the shaft 8410 includes a proximal end 8411 that is coupled to the mechanical structure 8700, and a distal end 8412 that is coupled to a proximal clevis 8510 of the wrist assembly 8500. The shaft 8410 defines a lumen (not shown) or multiple passageways through which the cables and other components (e.g., electrical wires, ground wires, or the like) can be routed from the mechanical structure 8700 to the wrist assembly 8500.

The mechanical structure 8700 functions as an actuator or a transmission or a "transmission assembly" to move the cables to produce the desired movement (pitch, yaw, or grip) at the wrist assembly 8500. Specifically, the mechanical structure 8700 includes components and controls to move some of the cables in a proximal direction (i.e., to pull in certain cables) while simultaneously allowing the distal movement (i.e., releasing or "paying out") of other of the cables in equal lengths. In this manner, the mechanical structure 8700 can maintain the desired tension within the cables, and can ensure that the lengths of the cables are conserved (i.e., moved in equal amounts) during the entire range of motion of the wrist assembly 8500. In some embodiments, for example, the mechanical structure 8700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments, however, conservation of the lengths of the cables is not required.

In some embodiments, the mechanical structure 8700 can include one or more linear actuators that produce translation (linear motion) of a portion of the cables. Such mechanisms can include, for example, a gimbal, a lever, or any other suitable mechanism to directly pull (or release) an end portion of any of the cables. For example, in some embodiments, the mechanical structure 8700 can include any of the transmission assemblies or components described in U.S. Patent Application Pub. No. US 2015/0047454 $A_1$ (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety. In other embodiments, however, the mechanical structure 8700 can include a capstan or other motor-driven roller that rotates or "winds" a portion of any of the cables to produce the desired cable movement. For example, in some embodiments, the mechanical structure 8700 can include any of the backend assemblies or components described in U.S. Pat. No. 9,204,923 B2 (filed Jul. 16, 2008), entitled "Medical Instrument Electronically Energized Using Drive Cables," which is incorporated herein by reference in its entirety.

Referring to FIGS. 21-22, the wrist assembly 8500 includes a first clevis 8510 (which functions as a proximal first link) and a second clevis 8610 (which functions as a distal second link). The first clevis 8510 has a proximal end portion 8511 and a distal end portion 8512. The proximal end portion 8511 is coupled to the distal end portion 8412 of the instrument shaft 8410. The distal end portion 8512 includes a joint portion that is rotatably coupled to a mating joint portion of the second clevis 8610. In this manner, the first clevis 8510 and the second clevis 8610 form the wrist assembly 8500 having a first axis of rotation $A_1$ (also referred to as the pitch axis) about which the second link 8610 can rotate relative to the first link 8510. A pin 8543 extends through an opening 8542 at the distal end 8512 of the first clevis 8510 to rotatably couple the second clevis 8610 to the first clevis 8510.

The second clevis 8610 has a proximal end portion 8611 and a distal end portion 8612. As described above, the proximal end portion 8611 includes a joint portion that is rotatably coupled to the first clevis 8510. The proximal end portion 8611 also defines connectors 8652 to which the first pitch cable 8405 and the second pitch cable 8406 are coupled. The second clevis 8610 also includes a first pulley shaft 8618 and a second pulley shaft 8623, which support cable pulleys as described below. The distal end portion 8612 of the second clevis 8610 is coupled to the end effector 8460 by a central pin 8683. In this manner, the first tool assembly 8465 and the second tool assembly 8485 can rotate relative to the second clevis 8610 about a second axis of rotation (also referred to as the yaw axis) $A_2$. As shown in FIG. 21, the second axis of rotation $A_2$ (also referred to as the yaw axis) is non-parallel to the pitch axis $A_1$. Thus, the instrument 8400 provides for up to three degrees of freedom (i.e., a pitch motion about the first axis of rotation $A_1$, a yaw rotation about the second axis of rotation $A_2$, and a grip motion about the second axis of rotation $A_2$).

Figures 24, 25:
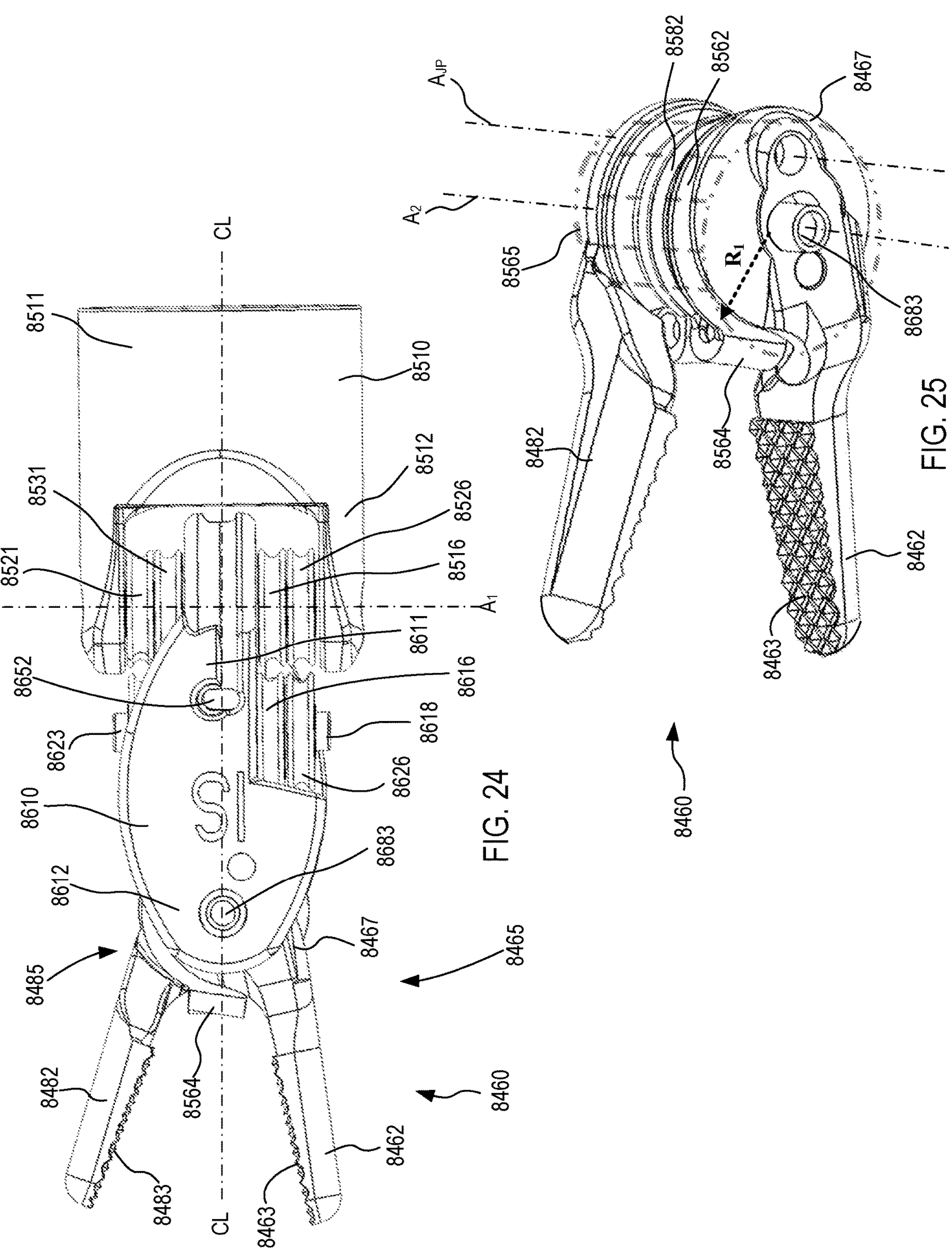
FIG. 24 is a side view of the distal end portion of the instrument shown in FIG. 21, showing the end effector in an opened configuration.
FIG. 25 is an exploded perspective view of the end effector of the instrument shown in FIGS. 20 and 21 in the opened configuration.

The first clevis 8510 and the second clevis 8610 define one or more guide channels through which the cables are routed and which can accommodate relative motion between the first clevis 8510 and the second clevis 8610. The first clevis 8510 and the second clevis 8610 also include one or more guide pulleys about which the cables are routed to minimize cable friction and to maintain the desired minimum bend radius of the cables during use. As shown in FIGS. 22 and 24, the first clevis 8510 includes a first pulley 8516 and a second pulley 8521 about which the first cable 8420 is routed, and a third pulley 8526 and fourth pulley 8531 about which the second cable 8440 is routed. The first pulley 8516 and the third pulley 8526 rotate about the pin 8543 on one side of the second clevis 8610 and the second pulley 8521 and the fourth pulley 8531 rotate about the pin 8543 on the other side of the second clevis 8610. The second clevis 8610 includes a first pulley 8816 and a second pulley 8821 about which the first cable 8420 is routed, and a third pulley 8826 and fourth pulley 8831 about which the second cable 8440 is routed. The first pulley 8616 and the third pulley 8626 rotate about the first shaft 8618 of the second clevis 8610 and the second pulley 8621 and the fourth pulley 8631 rotate about the second shaft 8623 of the second clevis 8610.

The end effector 8460 includes a first tool assembly 8465 (which functions as a first jaw-pulley pair) and a second tool assembly 8485 (which functions as a second jaw-pulley pair). Although the first tool assembly 8465 and the second tool assembly 8485 are separate components that cooperatively function to form the end effector 8460, aspects of the first tool assembly 8465 described below (e.g., identification of kinematic links formed by the first tool assembly) are applicable to the second tool assembly 8485, and vice-versa. The first tool assembly 8465 includes a first jaw 8462 coupled to a first pulley 8562 and the second tool assembly 8485 includes a second jaw 8482 coupled to a second pulley 8582.

The first pulley 8562 is a disk-shaped member that is rotatably coupled to the second clevis 8610 by the central pin 8683. The first pulley 8562 includes a first input connector 8564 and a first output pin 8572, and defines a central opening 8568 and a first jaw pivot opening 8569. The central pin 8683 is coupled within the central opening 8568 to allow the first pulley 8562 to rotate relative to the clevis 8610 about the yaw axis $A_2$, as shown by the arrow JJ in FIG. 21. As described in more detail below, the first jaw pivot opening 8569 is elongated to allow movement of the jaw pivot pin 8471 relative to the first pulley 8562 and the second pulley 8582 during operation. The distal end 8422 of first cable 8420 is coupled to the first pulley 8562 at the first input connector 8564 via a cable crimp (not shown). The first output pin 8572 is matingly coupled within the first pulley opening 8472 of the first jaw 8462 to transfer forces from the first pulley 8562 to the first jaw 8462.

The first jaw 8462 includes a distal portion 8463 and a proximal portion 8467. The distal portion 8463 functions as a grip portion to cooperate with the second jaw 8482 to contact tissue, grasp a needle (e.g., the needle 8010), or perform other operations. The proximal portion 8467 defines the first pulley opening 8472, the first jaw pivot opening 8469, and the first central opening 8468. As shown, the central pin 8683 extends through the first central opening 8468, which is elongated to allow linear movement of the first jaw 8462 and the second jaw 8482 about the central pin 8683 during operation. The first jaw 8462 is rotatably coupled to the second jaw 8482 by a jaw pivot pin 8471, which defines a jaw pivot axis $A_{JP}$ (see FIG. 25). The jaw pivot pin 8471 is rotatably coupled within the first jaw pivot opening 8469 (and the second jaw pivot opening 8489). Thus, when the torque applied to the first pulley 8562 by the first cable 8420 is transferred to the first jaw 8462, the first jaw 8462 rotates relative to the second jaw 8482 (and also the clevis 8610) about the jaw pivot axis $A_{JP}$. Because the jaws do not rotate relative to each other about the central pin 8683, when the jaw rotate, there is some translational motion relative to the central pin 8683, which is permitted by the inclusion of the first central opening 8468 (and the second central opening 8488). The jaw pivot axis $A_{JP}$ is offset from the yaw axis $A_2$ along an end effector center line CL.

The second pulley 8582 is a disk-shaped member that is rotatably coupled to the second clevis 8610 by the central pin 8683. The second pulley 8582 includes a second input connector 8584 and a second output pin 8592, and defines a central opening 8588 and a second jaw pivot opening 8589. The central pin 8683 is coupled within the central opening 8588 to allow the second pulley 8582 to rotate relative to the clevis 8610 about the yaw axis $A_2$. As described in more detail below, the second jaw pivot opening 8589 is elongated to allow movement of the jaw pivot pin 8471 relative to the second pulley 8582 and the first pulley 8562 during operation. The distal end 8442 of second cable 8440 is coupled to the second pulley 8582 at the second input connector 8584 via a cable crimp (not shown). The second output pin 8592 is matingly coupled within the second pulley opening 8492 of the second jaw 8482 to transfer forces from the second pulley 8582 to the second jaw 8482.

The second jaw 8482 includes a distal portion 8483 and a proximal portion 8487. The distal portion 8483 functions as a grip portion to cooperate with the first jaw 8462 (e.g., to grasp the needle 8010). The proximal portion 8487 defines the second pulley opening 8492, the second jaw pivot opening 8489, and the second central opening 8488. As shown, the central pin 8683 extends through the second central opening 8488, which is elongated to allow movement of the second jaw 8482 and the first jaw 8462 about the central pin 8683 during operation. When the torque applied to the second pulley 8582 by the second cable 8440 is transferred to the second jaw 8482, the second jaw 8482 rotates relative to the first jaw 8462 (and also the clevis 8610) about the jaw pivot axis $A_{JP}$.

The first cable 8420 is coupled to the first pulley 8562 and the second cable 8440 is coupled to the second pulley 8582 at an input radius from the yaw axis $A_2$. Thus, when an input pulley force is applied by the cables onto the pulleys, an input torque is produced about the yaw axis $A_2$ to rotate the pulleys. Additionally, the first pulley 8562 and the second pulley 8582 define a pulley envelope 8565 (see FIG. 25) as the cylindrical volume about the yaw axis $A_2$ that has an envelope radius equal to the outer-most radius of the pulleys.

The geometric layout and the kinematic links formed with the first and second tool assemblies 8465, 8485 are similar to those shown for the first and second tool assemblies 4465, 4485 above, and are therefore not described in great detail herein. For example, the geometry of the jaws 4462, 4482 described above (e.g., the overall length, the grip length, and the tip-to-grip distance) is the same as that for the jaws 8462, 8482. Additionally, the offset of the jaw pivot axis $A_{JP}$ from the yaw axis $A_2$ (in the rear pivot configuration) and the applied length $L_A$ of the jaws 4462, 4482 is the same as that for the jaws 8462, 8482. Similarly, the kinematic input link $L_1$ defined within the pulleys 4562, 4582 and the input link angle Θ is the same as that for the pulleys 8562, 8582. Moreover, as described above, these kinematic links, as well as the input radius (similar to the radius $R_1$ described herein) remain within the pulley envelope 8565.

Accordingly, in use the end effector 8460 can amplify the input pulley force to produce a higher grip force produced by the jaws 8462, 8482 than would be produced with a standard single-piece jaw and pulley system. As described herein with respect to the end effector 4460, the end effector 8460 (and each of the tool assemblies 8465, 8485) includes additional kinematic linkages to increase the moment arm upon which the input pulley force is exerted, thereby increasing the output grip force.

Additionally, the elongated shape of the first jaw pivot opening 8569 and the second jaw pivot opening 8589 allows relative motion between each pulley and its respective jaw (e.g., the second pulley 8582 and the second jaw 8482). The configuration of the first jaw pivot opening 8569 and the second jaw pivot opening 8589 also allows such relative motion while maintaining the jaw pivot axis Aw, and the kinematic links (e.g., the input link $L_1$ and the applied link $L_A$) within the pulley envelope 8565. Because the jaw pivot pin 8471 is within each of the first jaw pivot opening 8569 and the second jaw pivot opening 8589, in certain configurations (e.g., fully opened), the side wall of the first pulley 8562 and the side wall of the second pulley 8582 can collectively limit movement of the jaw pivot pin 8471 and can also limit rotation of the jaws (e.g., at the fully opened configuration, see FIG. 26). Similarly, the elongated shape of the first central opening 8468 and the second central opening 8488 allows movement of the first jaw 8462 and the second jaw 8482 about the central pin 8683 during operation. Because the central pin 8683 is within each of the central openings 8468, 8488, the side wall of the first jaw 8462 and the side wall of the second jaw 8482 can collectively limit movement of the jaws about the central pin 8683 and can also limit rotation of the jaws (e.g., at the fully opened configuration, see FIG. 26)

Figure 26:
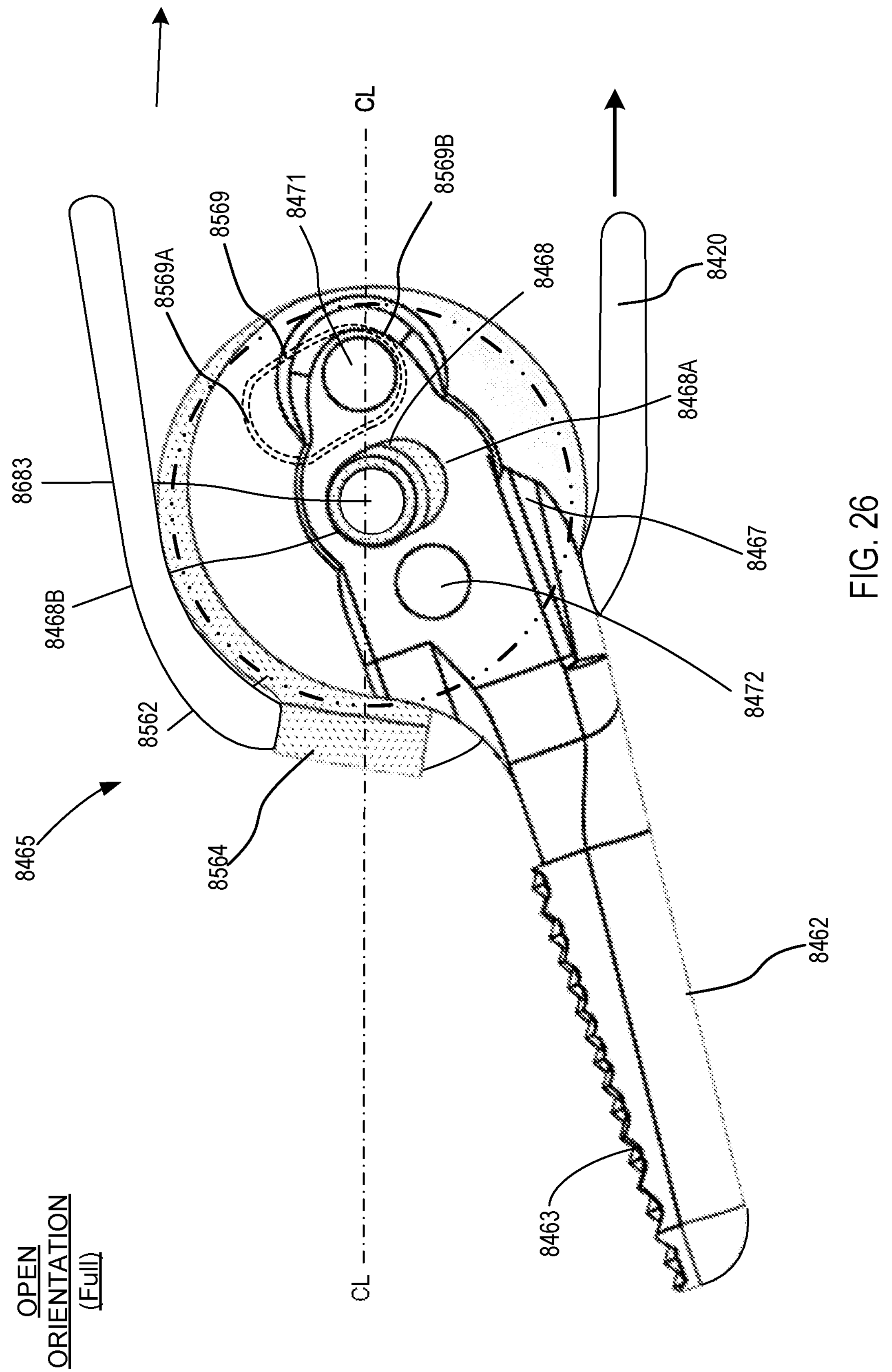
FIGS. 26 and 27 are side views of the first tool assembly of the end effector shown in FIG. 25, showing the end effector in the fully opened configuration (FIG. 26) and a partially-opened configuration (FIG. 27).
Figure 27:
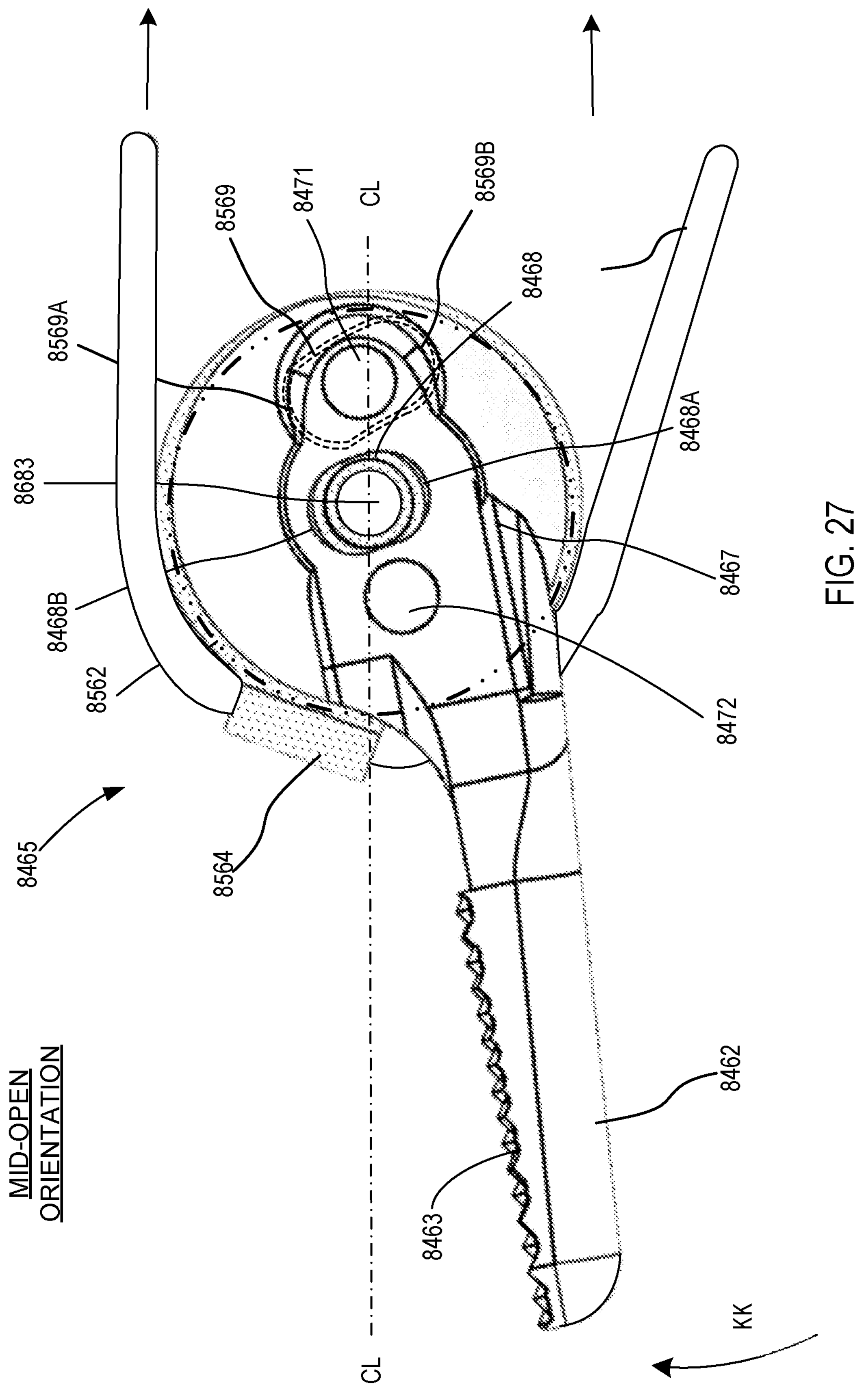
Figure 28:
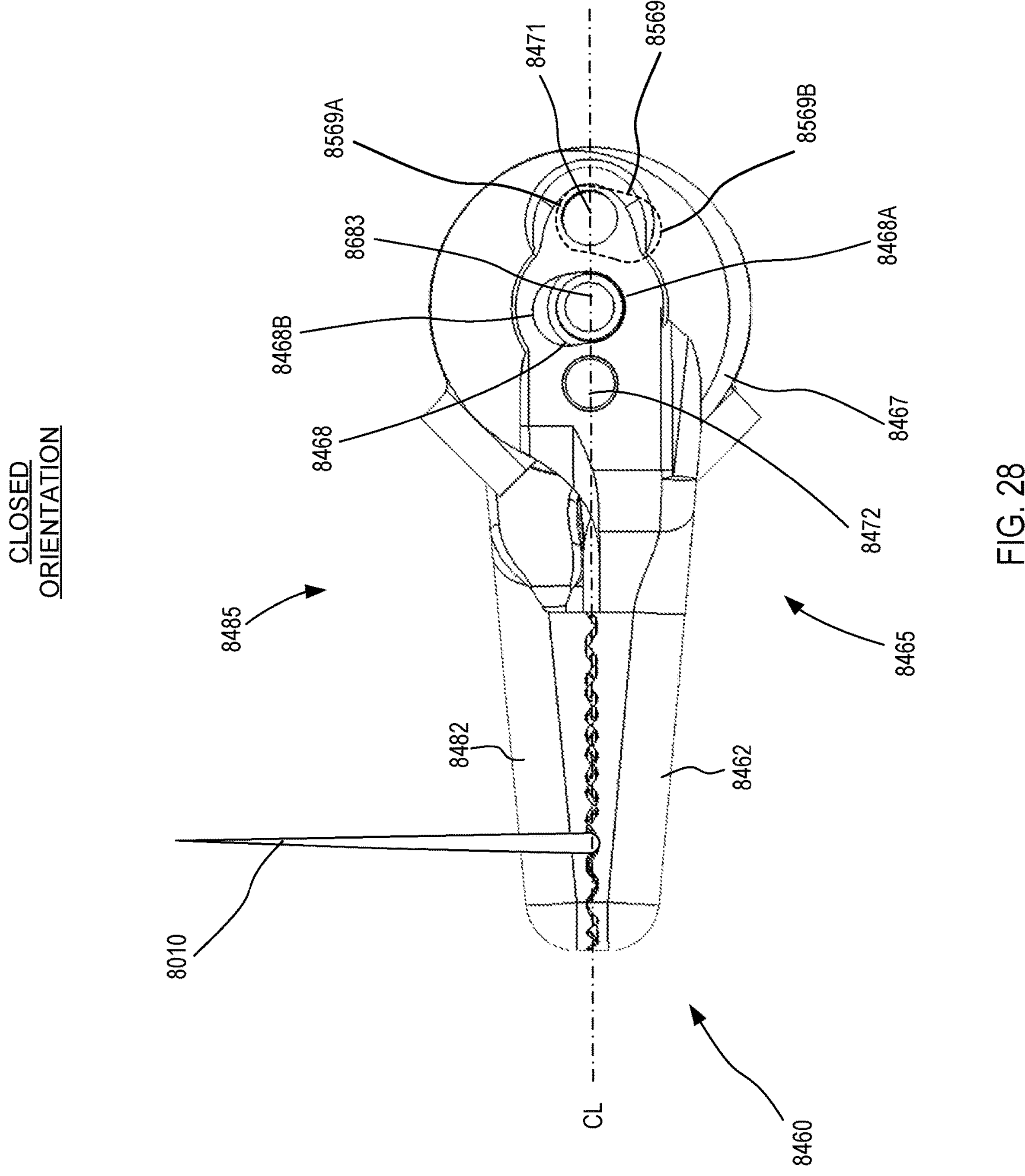
FIG. 28 is a side view of the end effector of the instrument shown in FIGS. 20 and 21 in the closed configuration grasping a suture needle.

For example, FIGS. 26-28 show the first jaw pivot opening 8569 (in dashed lines, as it is behind the first jaw 8462) and the first central opening 8468. As shown in FIG. 26, when the end effector 8460 is in the fully opened configuration, the jaw pivot pin 8471 is in contact with a second end 8569B of the first jaw pivot opening 8569. Although not shown, the opposite side of the jaw pivot pin 8471 can also be in contact with a first end of the second jaw pivot opening 8589. Thus, further relative motion between each jaw and its respective pulley (e.g., the first jaw 8462 and the first pulley 8562) in the "opened" direction is stopped. Additionally, the when the end effector 8460 is in the fully opened configuration, the central pin 8683 can be in contact with a second end 8468B of the first central opening 8468. Although not shown, the opposite side of the central pin 8683 can also be in contact with a first end of the second central opening 8488. This contact also prevents further movement of the jaws towards the "opened" direction.

Conversely, when the end effector 8460 is in the fully closed configuration (FIG. 28), the jaw pivot pin 8471 has clearance with (i.e., is spaced apart from, even if only by a small amount) a first end 8569A of the first jaw pivot opening 8569. Although not shown, the opposite side of the jaw pivot pin 8471 is also in clearance with a second end of the second jaw pivot opening 8589. Thus, further relative motion between each jaw and its respective pulley (e.g., the first jaw 8462 and the first pulley 8562) in the "closed" direction is not limited by the jaw pivot openings. By ensuring end clearance, the jaws will not be subject to premature stopping (e.g., if the jaws are gripping a very thin object). Additionally, when the end effector 8460 is in the fully closed configuration, the central pin 8683 has clearance with (i.e., is spaced apart from) a first end 8468A of the first central opening 8468. In some embodiments, the amount of clearance is small and therefore may not be readily seen in the drawings. Although not shown, the opposite side of the central pin 8683 is also in clearance with a second end of the second central opening 8488. This clearance also prevents premature stopping of the jaws when moving towards the "closed" direction.

Figure 29:
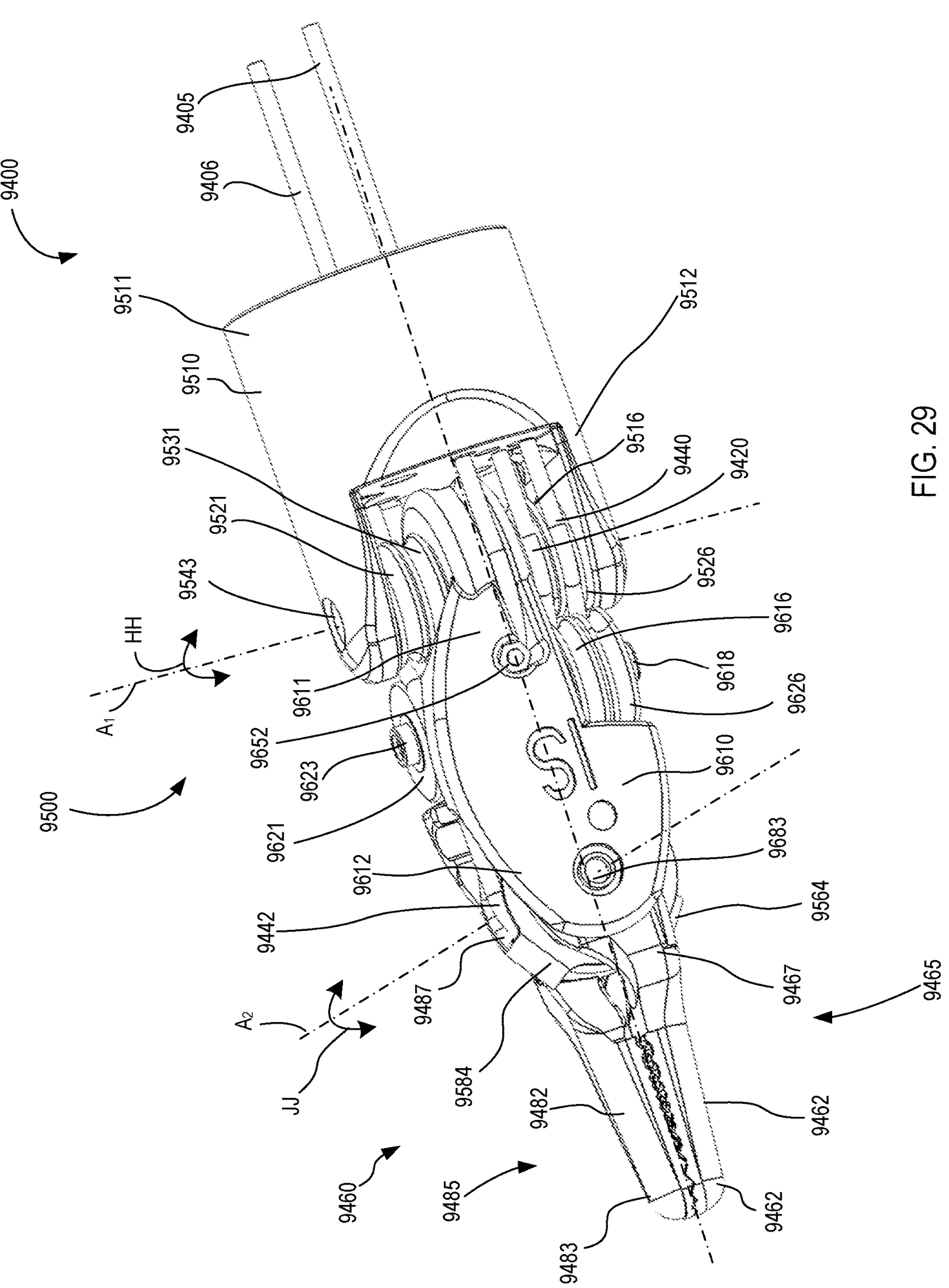
FIG. 29 is an enlarged perspective view of an end effector and wrist assembly of an instrument, according to an embodiment.
Figure 30:
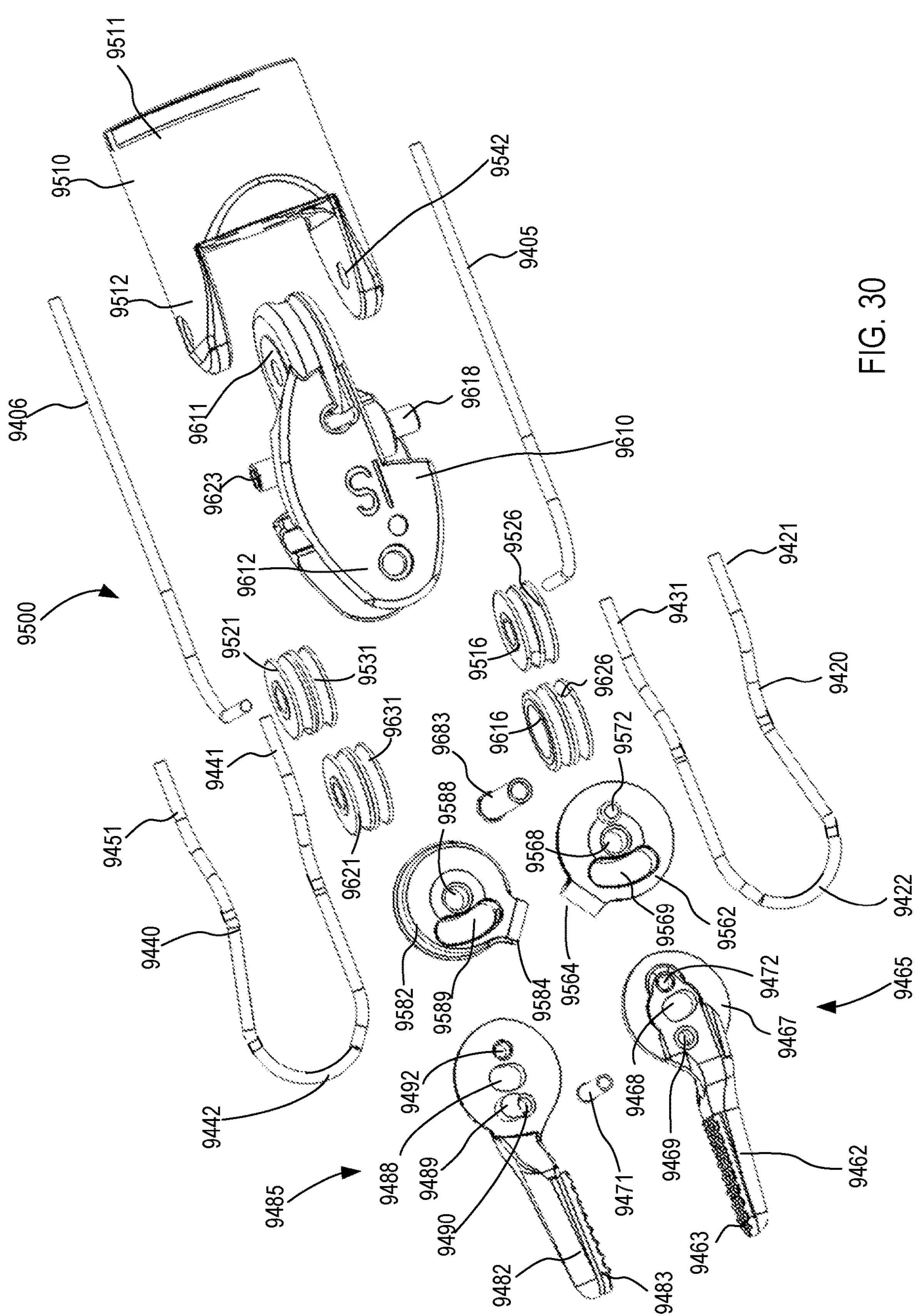
FIG. 30 is an exploded perspective view of the distal end portion of the instrument shown in FIG. 29.
Figure 31:
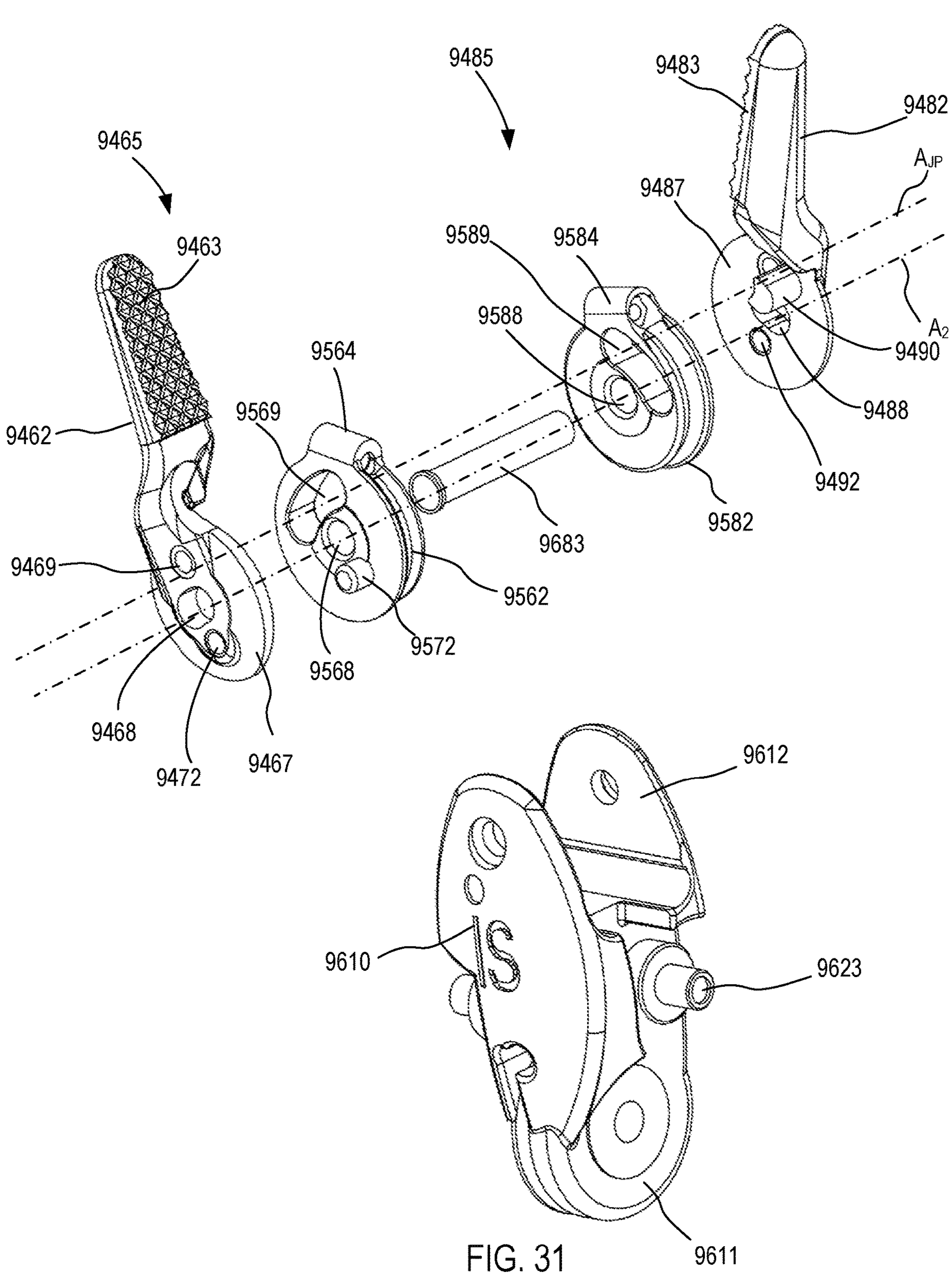
FIG. 31 is an exploded perspective view of the end effector of the instrument shown in FIG. 29.
Figure 32:
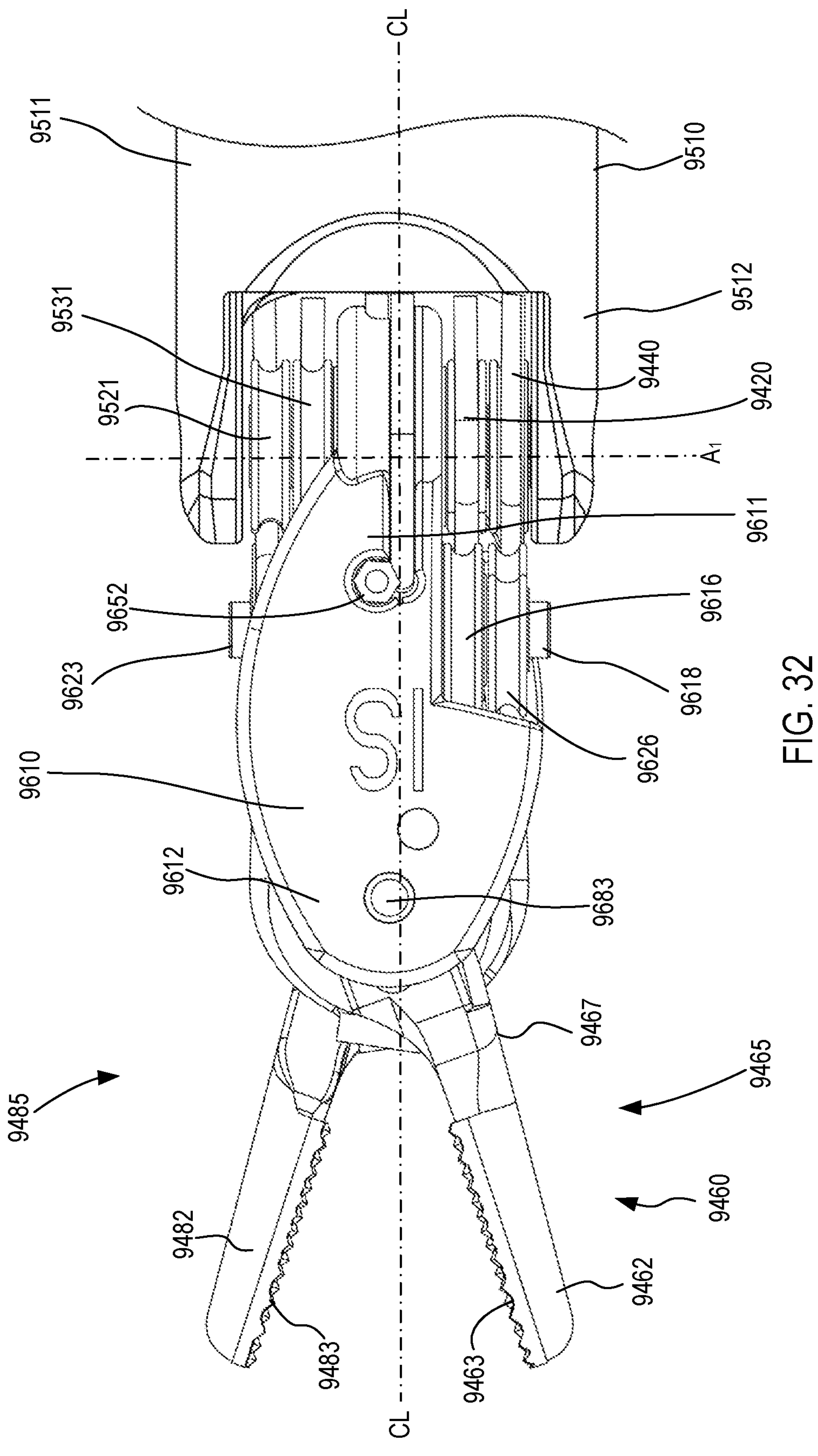
FIG. 32 is a side view of the distal end portion of the instrument shown in FIG. 29, showing the end effector in an opened configuration.

FIGS. 29-35 are various views of the distal end of an instrument 9400 with an end effector 9460 having a front pivot and forward grip topology and with the pulleys in between the jaws, according to an embodiment. The instrument 9400 or any of the components therein are optionally parts of a surgical system that performs surgical procedures, and which can include a manipulator unit, a series of kinematic linkages, a series of cannulas, or the like. The instrument 9400 (and any of the instruments described herein) can be used in any suitable surgical system, such as the MIRS system 1000 shown and described above. The instrument 9400 can include a mechanical structure 8700 and a shaft 8410 as described above. The instrument 9400 includes a wrist assembly 9500 and an end effector 9460. The instrument also includes a first pitch cable 9405 and a second pitch cable 9406 that couple the mechanical structure to the distal clevis 9610 of the wrist assembly 9500. Movement of the first pitch cable 9405 and second pitch cable 9406 produces rotation of the wrist assembly 9500 (i.e., pitch rotation; the term pitch is arbitrary) about a first axis of rotation $A_1$ (see the arrow HH in FIG. 29). The instrument 9400 also includes a first cable 9420 and a second cable 9440 that couple the mechanical structure to the end effector 9460. As shown in FIG. 30, the first cable 9420 forms a cable loop having a first proximal portion 9421, a distal portion 9422, and a second proximal portion 9431. The distal portion 9422 is coupled to the input connector 9564 of the first pulley 9562, as described in more detail below. The first proximal portion 9421 and the second proximal portion 9431 are routed proximally to the mechanical structure 9700. The second cable 9440 forms a cable loop having a first proximal portion 9441, a distal portion 9442, and a second proximal portion 9451. The distal portion 9442 is coupled to the input connector 9584 of the second pulley 9582, as described in more detail below. The first proximal portion 9441 and the second proximal portion 9451 are routed proximally to the mechanical structure 9700. Movement of the first cable 9420 and second cable 9440 produces yaw rotation (the term yaw is arbitrary) of the end effector 9460 about a second axis of rotation $A_2$ (see the arrow JJ in FIG. 29), a gripping rotation of the tool members of the end effector 9460 about the second axis of rotation $A_2$, or any combination of these movements. Changing the pitch or yaw of the instrument 9400 can be performed by manipulating the cables (i.e., moving or changing tension in the cables).

The wrist assembly 9500 includes a first clevis 9510 (which functions as a proximal first link) and a second clevis 9610 (which functions as a distal second link). The first clevis 9510 has a proximal end portion 9511 and a distal end portion 9512. The proximal end portion 9511 is coupled to the distal end portion 9412 of the instrument shaft 9410. The distal end portion 9512 includes a joint portion that is rotatably coupled to a mating joint portion of the second clevis 9610. In this manner, the first clevis 9510 and the second clevis 9610 form the wrist assembly 9500 having a first axis of rotation $A_1$ (also referred to as the pitch axis) about which the second link 9610 can rotate relative to the first link 9510. A pin 9543 extends through an opening 9542 at the distal end 9512 of the first clevis 9510 to rotatably couple the second clevis 9610 to the first clevis 9510.

The second clevis 9610 has a proximal end portion 9611 and a distal end portion 9612. As described above, the proximal end portion 9611 includes a joint portion that is rotatably coupled to the first clevis 9510. The proximal end portion 9611 also defines connectors to which the first pitch cable 9405 and the second pitch cable 9406 are coupled. The second clevis 9610 also includes a first pulley shaft 9618 and a second pulley shaft 9623, which support cable pulleys as described below. The distal end portion 9612 of the second clevis 9610 is coupled to the end effector 9460 by a central pin 9683. In this manner, the first tool assembly 9465 and the second tool assembly 9485 can rotate relative to the second clevis 9610 about a second axis of rotation (also referred to as the yaw axis) Az. As shown in FIG. 29, the second axis of rotation $A_2$ (also referred to as the yaw axis) is non-parallel to the pitch axis $A_1$. Thus, the instrument 9400 provides for up to three degrees of freedom (i.e., a pitch motion about the first axis of rotation $A_1$, a yaw rotation about the second axis of rotation $A_2$, and a grip motion about the second axis of rotation $A_2$).

The first clevis 9510 and the second clevis 9610 define one or more guide channels through which the cables are routed and which can accommodate relative motion between the first clevis 9510 and the second clevis 9610. The first clevis 9510 and the second clevis 9610 also include one or more guide pulleys about which the cables are routed to minimize cable friction and to maintain the desired minimum bend radius of the cables during use. As shown in FIG. 30, the first clevis 9510 includes a first pulley 9516 and a second pulley 9521 about which the first cable 9420 is routed, and a third pulley 9526 and fourth pulley 9531 about which the second cable 9440 is routed. The first pulley 9516 and the third pulley 9526 rotate about the pin 9543 on one side of the second clevis 9610 and the second pulley 9521 and the fourth pulley 9531 rotate about the pin 9543 on the other side of the second clevis 9610. The second clevis 9610 includes a first pulley 9816 and a second pulley 9821 about which the first cable 9420 is routed, and a third pulley 9826 and fourth pulley 9831 about which the second cable 9440 is routed. The first pulley 9616 and the third pulley 9626 rotate about the first shaft 9618 of the second clevis 9610 and the second pulley 9621 and the fourth pulley 9631 rotate about the second shaft 9623 of the second clevis 9610.

The end effector 9460 includes a first tool assembly 9465 (which functions as a first jaw-pulley pair) and a second tool assembly 9485 (which functions as a second jaw-pulley pair). Although the first tool assembly 9465 and the second tool assembly 9485 are separate components that cooperatively function to form the end effector 9460, aspects of the first tool assembly 9465 described below (e.g., identification of kinematic links formed by the first tool assembly) are applicable to the second tool assembly 9485, and vice-versa. The first tool assembly 9465 includes a first jaw 9462 coupled to a first pulley 9562 and the second tool assembly 9485 includes a second jaw 9482 coupled to a second pulley 9582.

The first pulley 9562 is a disk-shaped member that is rotatably coupled to the second clevis 9610 by the central pin 9683. The first pulley 9562 includes a first input connector 9564 and a first output pin 9572, and defines a central opening 9568 and a first jaw pivot opening 9569. The central pin 9683 is coupled within the central opening 9568 to allow the first pulley 9562 to rotate relative to the clevis 9610 about the yaw axis $A_2$, as shown by the arrow JJ in FIG. 29. As described in more detail below, the first jaw pivot opening 9569 is elongated to allow movement of the jaw pivot pin 9471 relative to the first pulley 9562 and the second pulley 9582 during operation. The distal end 9422 of first cable 9420 is coupled to the first pulley 9562 at the first input connector 9564 via a cable crimp (not shown). The first output pin 9572 is matingly coupled within the first pulley opening 9472 of the first jaw 9462 to transfer forces from the first pulley 9562 to the first jaw 9462.

The first jaw 9462 includes a distal portion 9463 and a proximal portion 9467. The distal portion 9463 functions as a grip portion to cooperate with the second jaw 9482 to contact tissue, grasp a needle (e.g., the needle 9010), or perform other operations. The proximal portion 9467 defines the first pulley opening 9472, the first jaw pivot opening 9469, and the first central opening 9468. The proximal portion 9467 also includes the jaw pivot guide 9470. As shown, the central pin 9683 extends through the first central opening 9468, which is elongated to allow movement of the first jaw 9462 and the second jaw 9482 about the central pin 9683 during operation. The first jaw 9462 is rotatably coupled to the second jaw 9482 by a jaw pivot pin 9471, which defines a jaw pivot axis $A_{JP}$ (see FIG. 31). The jaw pivot pin 9471 is rotatably coupled within the first jaw pivot opening 9469 (and the second jaw pivot opening 9489), and is supported by the jaw pivot guides 9470, 9490. Thus, when the torque applied to the first pulley 9562 by the first cable 9420 is transferred to the first jaw 9462, the first jaw 9462 rotates relative to the second jaw 9482 (and also the clevis 9610) about the jaw pivot axis $A_{JP}$. The jaw pivot axis $A_{JP}$ is offset from the yaw axis $A_2$ along an end effector center line CL.

The second pulley 9582 is a disk-shaped member that is rotatably coupled to the second clevis 9610 by the central pin 9683. The second pulley 9582 includes a second input connector 9584 and a second output pin 9592, and defines a central opening 9588 and a second jaw pivot opening 9589. The central pin 9683 is coupled within the central opening 9588 to allow the second pulley 9582 to rotate relative to the clevis 9610 about the yaw axis $A_2$. As described in more detail below, the second jaw pivot opening 9589 is elongated to allow movement of the jaw pivot pin 9471 relative to the second pulley 9582 and the first pulley 9562 during operation. The distal end 9442 of second cable 9440 is coupled to the second pulley 9582 at the second input connector 9584 via a cable crimp (not shown). The second output pin 9592 is matingly coupled within the second pulley opening 9492 of the second jaw 9482 to transfer forces from the second pulley 9582 to the second jaw 9482.

The second jaw 9482 includes a distal portion 9483 and a proximal portion 9487. The distal portion 9483 functions as a grip portion to cooperate with the first jaw 9462 (e.g., to grasp the needle 9010). The proximal portion 9487 defines the second pulley opening 9492, the second jaw pivot opening 9489, and the second central opening 9488. The proximal portion 9487 also includes the jaw pivot guide 9490. As shown, the central pin 9683 extends through the second central opening 9488, which is elongated to allow linear movement of the second jaw 9482 and the first jaw 9462 about the central pin 9683 during operation. When the torque applied to the second pulley 9582 by the second cable 9440 is transferred to the second jaw 9482, the second jaw 9482 rotates relative to the first jaw 9462 (and also the clevis 9610) about the jaw pivot axis $A_{JP}$. Because the jaws do not rotate relative to each other about the central pin 9683, when the jaw rotate, there is some translational motion relative to the central pin 9683, which is permitted by the inclusion of the first central opening 9468 (and the second central opening 9488).

The first cable 9420 is coupled to the first pulley 9562 and the second cable 9440 is coupled to the second pulley 9582 at an input radius from the yaw axis $A_2$. Thus, when an input pulley force is applied by the cables onto the pulleys, an input torque is produced about the yaw axis $A_2$ to rotate the pulleys. Additionally, the first pulley 9562 and the second pulley 9582 define a pulley envelope as the cylindrical volume about the yaw axis $A_2$ that has an envelope radius equal to the outer-most radius of the pulleys.

The geometric layout and the kinematic links formed with the first and second tool assemblies 9465, 9485 are similar to those shown for the first and second tool assemblies 5465, 5485 above, and are therefore not described in great detail herein. Moreover, the geometry of the jaws 4462, 4482 described above (e.g., the overall length, the grip length, and the tip-to-grip distance) is the same as that for the jaws 9462, 9482. Additionally, the offset of the jaw pivot axis $A_{JP}$ from the yaw axis $A_2$ (in the front pivot configuration) and the applied length $L_A$ of the jaws 5462, 5482 is the same as that for the jaws 9462, 9482. Similarly, the kinematic input link $L_1$ defined within the pulleys 5562, 5582 and the input link angle $\Theta$ is the same as that for the pulleys 9562, 9582. Moreover, as described above, these kinematic links, as well as the input radius (similar to the radius $R_1$ described herein) remain within the pulley envelope.

Accordingly, in use the end effector 9460 can amplify the input pulley force to produce a higher grip force produced by the jaws 9462, 9482 than would be produced with a standard single-piece jaw and pulley system. As described herein with respect to the end effector 5460, the end effector 9460 (and each of the tool assemblies 9465, 9485) includes additional kinematic linkages to increase the moment arm upon which the input pulley force is exerted, thereby increasing the output grip force.

Additionally, the elongated shape of the first jaw pivot opening 9569 and the second jaw pivot opening 9589 allows relative motion between each pulley and its respective jaw (e.g., the second pulley 9582 and the second jaw 9482). The configuration of the first jaw pivot opening 9569 and the second jaw pivot opening 9589 also allows such relative motion while maintaining the jaw pivot axis Aw, and the kinematic links (e.g., the input link $L_1$ and the applied link $L_A$) within the pulley envelope. Because the jaw pivot pin 9471 is within each of the first jaw pivot opening 9569 and the second jaw pivot opening 9589, in certain configurations the side wall of the first pulley 9562 (along with the pivot pin guide 9470) and the side wall of the second pulley 9582 (along with the pivot pin guide 9490) can collectively limit movement of the jaw pivot pin 9471 and thus also limit rotation of the jaws (e.g., at the fully opened configuration, see FIG. 33). Similarly, the elongated shape of the first central opening 9468 and the second central opening 9488 allows movement of the first jaw 9462 and the second jaw 9482 about the central pin 9683 during operation. Because the central pin 9683 is within each of the central openings 9468, 9488, the side wall of the first jaw 9462 and the side wall of the second jaw 9482 can collectively limit movement of the jaws about the central pin 9683 and can also limit rotation of the jaws (e.g., at the fully opened configuration, see FIG. 33).

Figure 33:
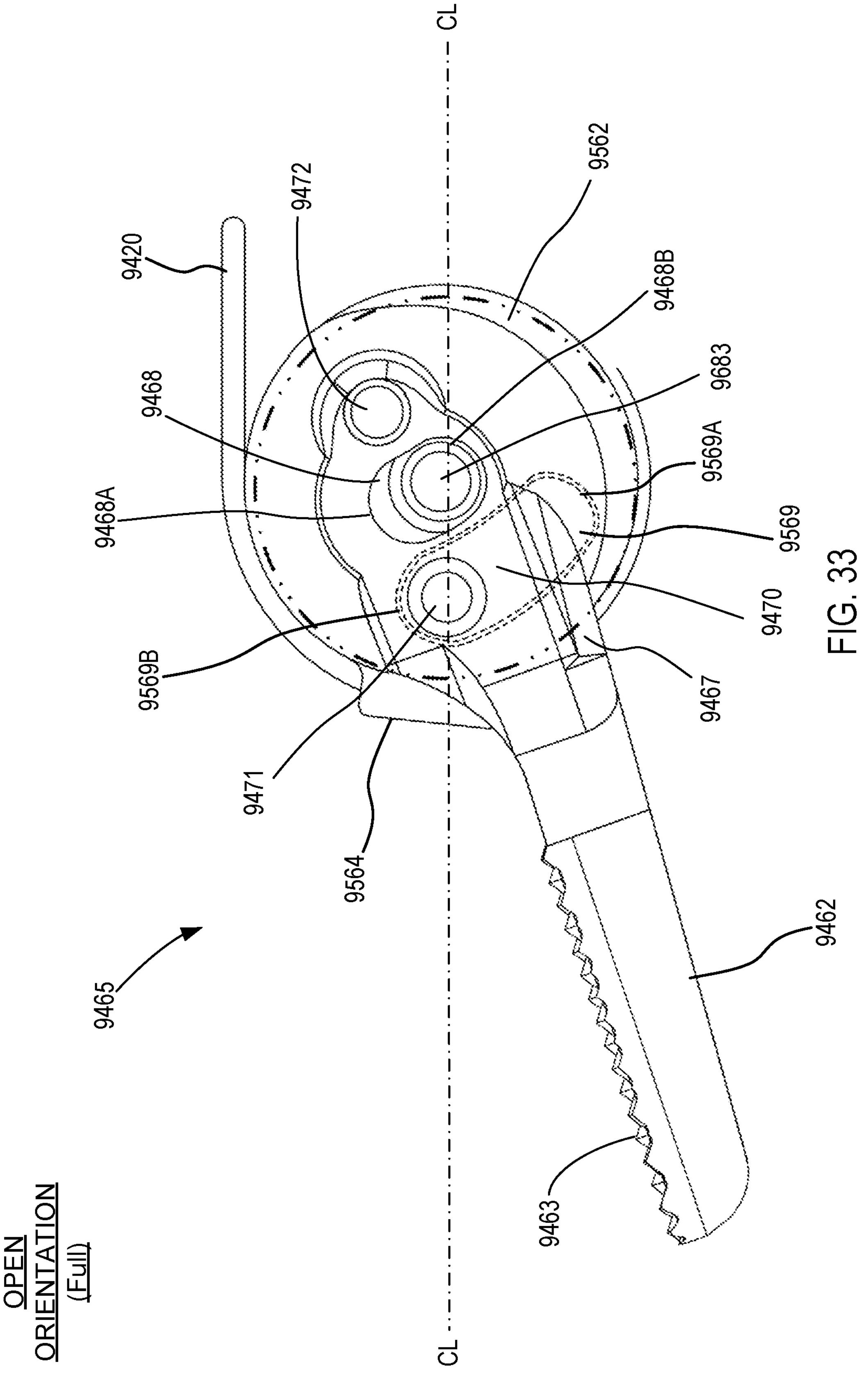
FIGS. 33 and 34 are side views of the first tool assembly of the end effector shown in FIG. 29, showing the end effector in the fully opened configuration (FIG. 33) and a partially-opened configuration (FIG. 34).
Figure 34:
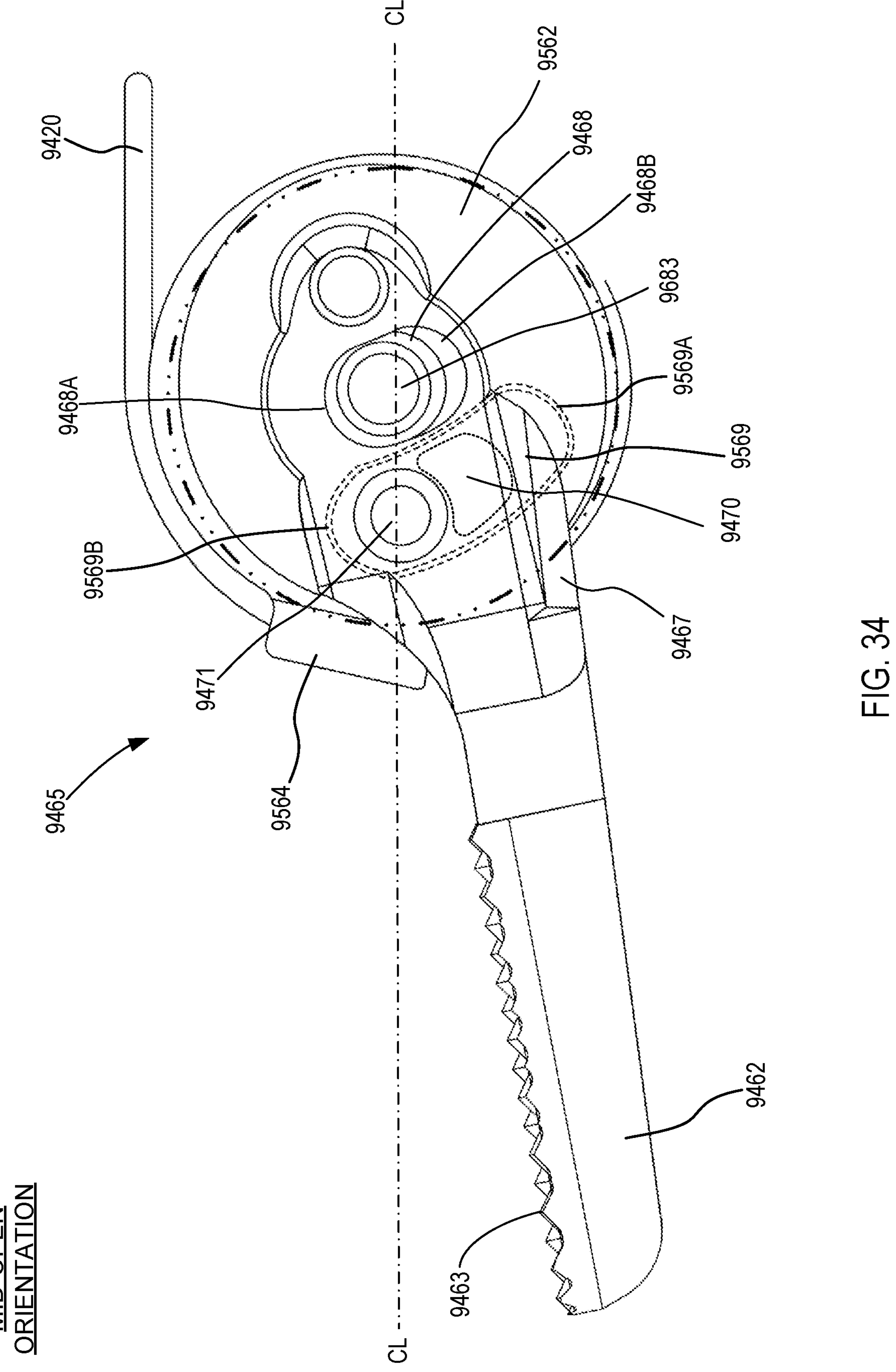
Figure 35:
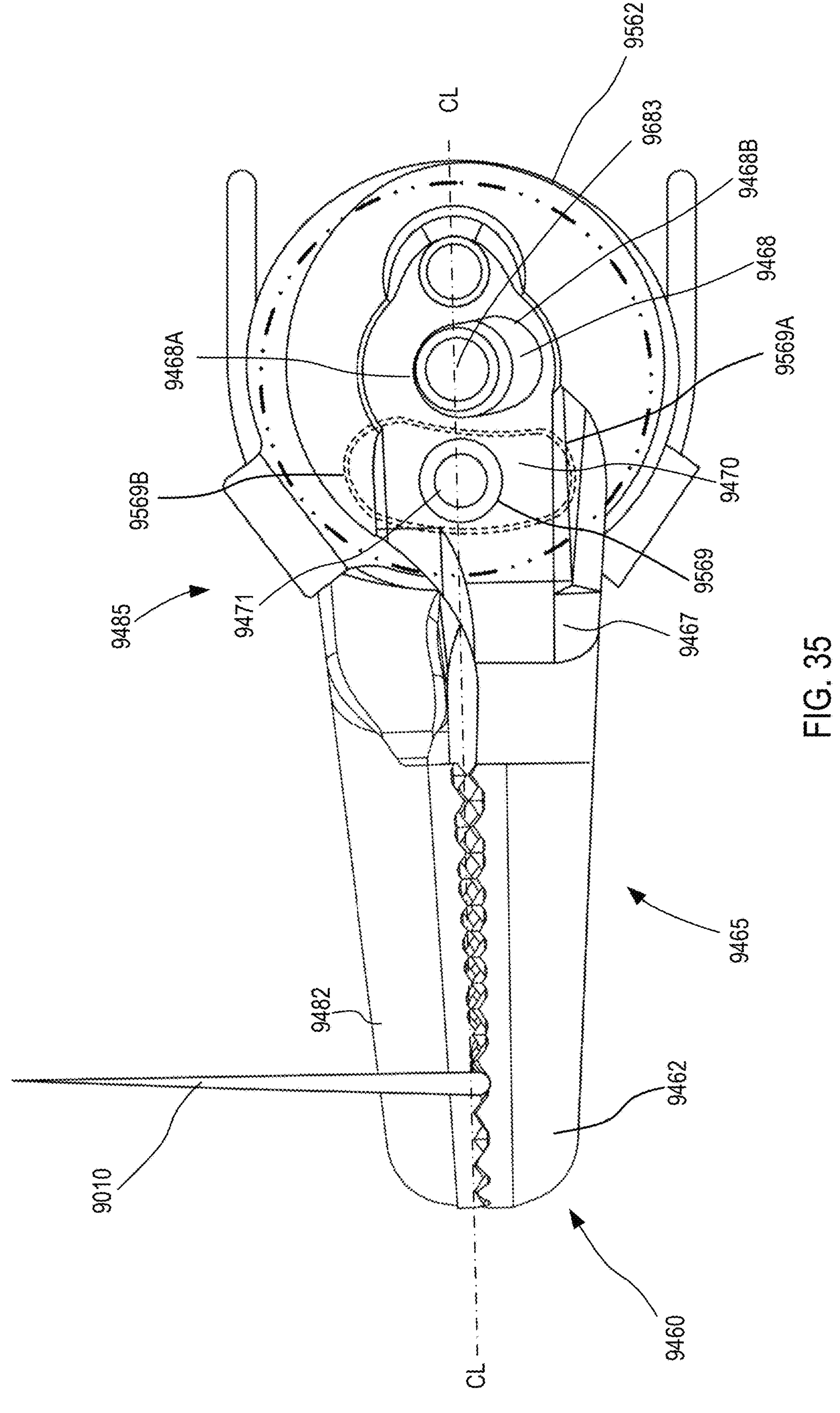
FIG. 35 is a side view of the end effector of the instrument shown in FIG. 29 in the closed configuration grasping a suture needle.

For example, FIGS. 33-35 show the first jaw pivot opening 9569 (in dashed lines, as it is behind the first jaw 9462) and the first central opening 9468. As shown in FIG. 33, when the end effector 9460 is in the fully opened configuration, the jaw pivot pin 9471 is in contact with a second end 9569B of the first jaw pivot opening 9569. Although not shown, the opposite side of the jaw pivot pin 9471 can also be in contact with a first end of the second jaw pivot opening 9589. Thus, further relative motion between each jaw and its respective pulley (e.g., the first jaw 9462 and the first pulley 9562) in the "opened" direction is stopped. Additionally, the when the end effector 9460 is in the fully opened configuration, the central pin 9683 is in contact with a second end 9468B of the first central opening 9468. Although not shown, the opposite side of the central pin 9683 can also be in contact with a first end of the second central opening 9488. This contact also prevents further movement of the jaws towards the "opened" direction.

Conversely, when the end effector 9460 is in the fully closed configuration (FIG. 35), the jaw pivot pin 9471 has clearance with (i.e., is spaced apart from) a first end 9569A of the first jaw pivot opening 9569. Although not shown, the opposite side of the jaw pivot pin 9471 is also in clearance with a second end of the second jaw pivot opening 9589. Thus, further relative motion between each jaw and its respective pulley (e.g., the first jaw 9462 and the first pulley 9562) in the "closed" direction is not limited by the jaw pivot openings. Additionally, the when the end effector 9460 is in the fully closed configuration, the central pin 9683 has clearance with (i.e., is spaced apart from) a first end 9468A of the first central opening 9468. Although not shown, the opposite side of the central pin 9683 is also spaced apart from a second end of the second central opening 9488. This clearance also prevents premature stopping of the jaws when moving towards the "closed" direction.

Figures 36, 37:
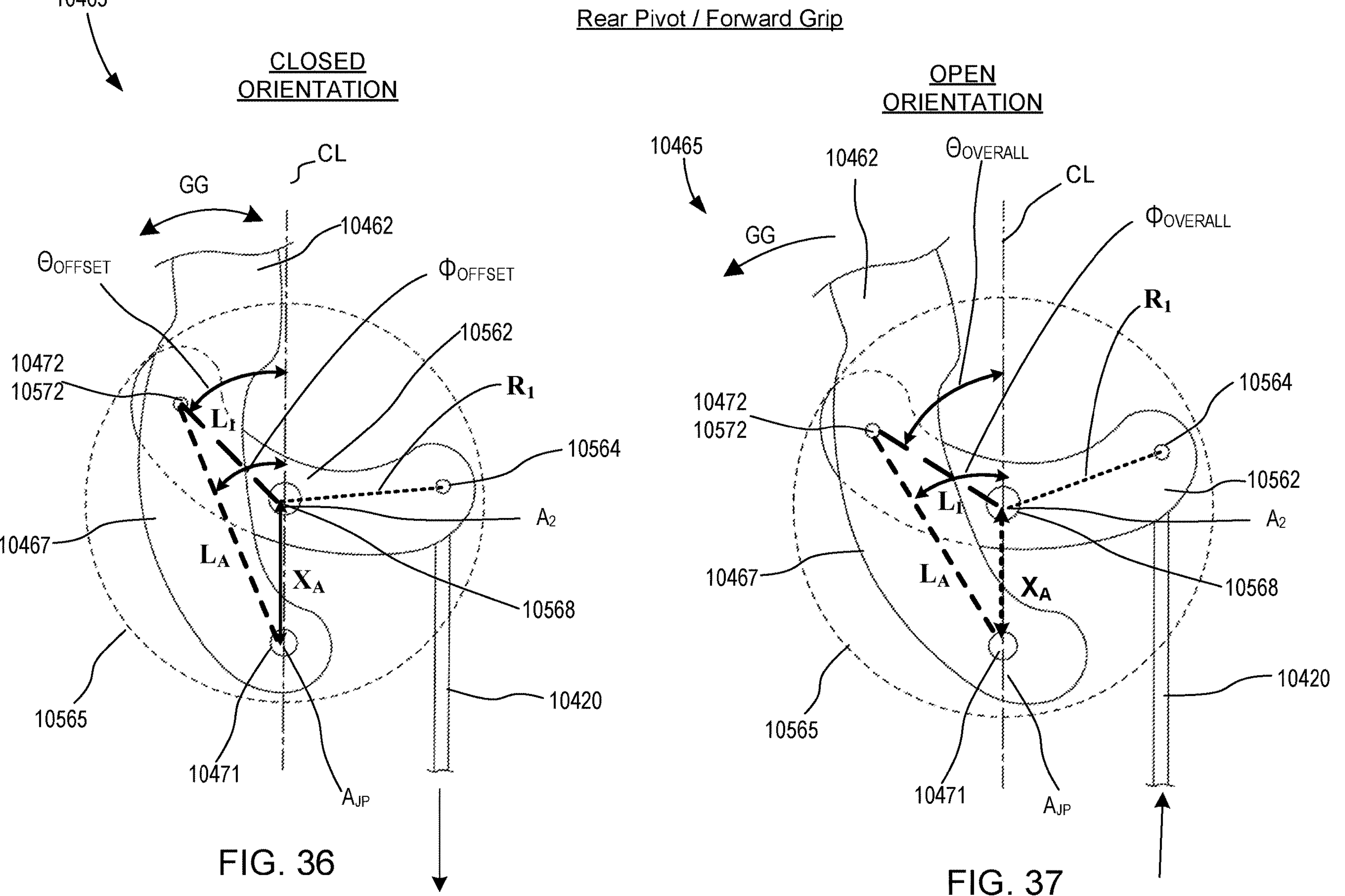
FIGS. 36 and 37 are side views of a tool assembly according to an embodiment having a rear pivot/forward grip topology, shown in a first (closed) configuration (FIG. 36) and a second (open) configuration (FIG. 37).

Although the end effector 8460 and the end effector 9460 are shown as having tool assemblies that include a jaw coupled to a pulley (e.g., the first pulley 8562), in other embodiments any of the instruments described herein can include a tool assembly having a jaw coupled to any suitable rotatable member to define the kinematic links to produce the desired amplification as described herein. Such rotational members can include levers, links, gears, or any other structure suitable for being coupled to the jaw and transferring force from a tension member to the jaw. For example, FIGS. 36 and 37 are schematic illustrations of a tool assembly 10465 having a rear pivot and forward grip topology, according to an embodiment. Specifically, FIGS. 36 and 37 are side views of a portion of the tool assembly 10465 in a first (closed) configuration (FIG. 36) and a second (open) configuration (FIG. 37). The tool assembly 10465 can be incorporated within any of the end effectors or medical instruments described herein, and can be configured the same or similar to, and function the same or similar to, other tool assemblies described herein. For example, the tool assembly 10465 can be a first tool assembly of an end effector that includes two tool assemblies, similar to the end effectors 4460, 8460, 9460 described herein. Thus, although FIGS. 36 and 37 only show the first tool assembly 10465, it is understood that an end effector can include the first tool assembly 10465 and a second tool assembly (not shown) that are separate components that cooperatively function to form the end effector. Aspects of the first tool assembly 10465 (e.g., identification of kinematic links formed by the first tool assembly) are applicable to a second tool assembly (not shown). Moreover, certain aspects of the tool assembly 10465 and the end effector in which the tool assembly 10465 is included are not described in detail below, but rather are understood to be similar to aspects of the end effectors (e.g., the end effectors 4460, 8460, 9460) described herein. For example, although FIGS. 36 and 37 do not show a clevis, it is understood that the tool assembly 10465 can be rotatably coupled to a central axis $A_2$ of a clevis (similar to the clevis 4610, 8610, 9610 or any other clevis as shown herein).

The tool assembly 10465 includes a jaw 10462 coupled to a rotatable member 10562. Like the jaws 4462, 8462, and 9462, the jaw 10462 includes a distal portion and a proximal portion 10467. The proximal portion 10467 includes a rotatable member connector 10472, which couples the jaw 10462 to and transfers forces from its mating rotatable member 10562. Additionally, the proximal portion 10467 of the jaw 10462 is rotatably coupled to the proximal portion of a second jaw (not shown) by a jaw pivot pin 10471, which defines a jaw pivot axis $A_{JP}$. The distal portions of the two jaws function as grip portions to cooperatively contact tissue, grasp a needle, or perform other operations, as shown and described above with reference to the jaws 4462 and 4482 and the jaws 8462 and 8482.

The rotatable member 10562 can be any suitable structure for operatively coupling the jaw 10462 to the tension member 10420, such as a link, a gear, or a pulley. The rotatable member 10562 is rotatably coupled to the clevis (not shown) about the central axis $A_2$. The rotatable member 10562 includes an input connector 10564 and an output connector 10572, and defines a central opening 10568 and a jaw pivot opening (not identified, but that can be similar to the jaw pivot opening 2569 described above). A central pin can be coupled within the central opening 10568 to allow the rotatable member 10562 and a second rotatable member (of a second tool assembly, not shown) to rotate relative to the clevis about the central axis $A_2$. A tension member 10420 is coupled to the rotatable member 10562 at the input connector 10564. The tension member 10420 can be any suitable connector that transfers force from a mechanical structure (not shown) to the tool assembly 10465, such as a cable, a band, or a push-pull rod. The tension member 10420 is coupled to the rotatable member 10562 at a first input radius $R_1$ from the central axis $A_2$. Thus, when an input force is applied by the tension member 10420 onto the rotatable member 10562, an input torque (analogous to the input torque $T_{in}$ shown in the free-body diagram of FIG. 14) is produced about the central axis $A_2$ to rotate the rotatable member 10562 about the central axis $A_2$. Because in this embodiment, the tension member 10420 is not wrapped about an outer diameter or surface of the rotatable member 10562, the moment arm (or distance between the input force and the central axis $A_2$ changes as a function of the rotation angle. Additionally, the rotatable member 10562 defines a rotatable member envelope 10565 as the cylindrical volume about the central axis $A_2$ that has an envelope radius equal to the outer-most radius of the rotatable member 10562. In some embodiments, the rotatable member envelope 10565 has an envelope radius equal to the outer-most portion of the rotatable member 10562. In some embodiments, the rotatable member envelope 10565 is the same as a rotatable member envelope defined by the second rotatable member.

The output connector 10572 can be any suitable connector or mechanism that couples the jaw 10462 to the rotatable member 10562 to transfer forces from the rotatable member 10562 to the jaw 10462. The output connector 10572 is radially offset from the central axis $A_2$ by a jaw input length, identified as $L_1$. Thus, the coupling between the rotatable member 10562 and the jaw 10462 defines a kinematic input link identified as $L_1$ that rotates about the central axis $A_2$. The input link $L_1$ and the end effector center line CL form an input link angle that changes when the rotatable member 10562 rotates about the central axis $A_2$. When the end effector is in the closed configuration (see FIG. 36), the input link angle is identified as $\Theta_{OFFSET}$. When the rotatable member rotates towards the open position (see FIG. 37), the input link angle increases to a value of $\Theta+\Theta_{OFFSET}$ (also referred to as $\Theta_{OVERALL}$). As described in more detail above, the value of $\Theta_{OFFSET}$ can be selected to minimize the impact of the push-pull force on the grip force applied by the tool members. For example, in some embodiments, the value of $\Theta_{OFFSET}$ can be less than about 10 degrees. In some embodiments, the value of $\Theta_{OFFSET}$ can be less than about 5 degrees. In some embodiments, the value of $\Theta_{OFFSET}$ can be about zero degrees. Similarly stated, in some embodiments, the coupling between the rotatable member 10562 and the jaw 10462 is along the end effector center line CL when the end effector is in the closed configuration. As shown, the output connector 10572 and the kinematic link $L_1$ are within the rotatable member envelope 10565.

The proximal portion 10467 of the jaw 10462 includes the rotatable member connector 10472, which couples the jaw 10462 to and transfers forces from the rotatable member 10562. Thus, when the input torque applied to the rotatable member 10562 by the tension member 10420 is transferred to the jaw 10462, the jaw 10462 rotates relative to the second jaw (and also the clevis; not shown) about the jaw pivot axis $A_{JP}$, as shown by the arrow GG. The jaw pivot axis $A_{JP}$ is offset from the central axis $A_2$ along an end effector center line CL, which is defined between (and normal to) the central axis $A_2$ and the jaw pivot axis $A_{JP}$ when the end effector is in its closed configuration. The offset distance between the jaw pivot axis $A_{JP}$ and the central axis $A_2$ is indicated as $X_A$. The jaw pivot axis $A_{JP}$ is also offset from the rotatable member connector 10472 by a jaw applied length, identified as $L_A$. Thus, the coupling of the jaws at the jaw pivot pin 10471 and the coupling of the jaw 10462 and the rotatable member 10562 at the rotatable member connector 10472 define a kinematic applied link identified as $L_A$ that rotates about the jaw pivot axis $A_{JP}$. The applied input link $L_A$ and the end effector center line CL form an applied link angle that changes when the jaw 10462 rotates about the central axis $A_2$ and the jaw pivot axis $A_{JP}$. When the end effector is in the closed configuration (see FIG. 36), the input link angle is identified as $\Phi_{OFFSET}$. When the rotatable member rotates towards the open position (see FIG. 37), the applied link angle increases to a value of $\Phi+\Phi_{OFFSET}$ (also referred to as $\Phi_{OVERALL}$). As shown, the jaw pivot axis $A_{JP}$ and the kinematic link $L_A$ are within the rotatable member envelope 10565.

As shown, the rotatable member 10562 and a second rotatable member (not shown) each can each be shaped such that the jaw pivot pin 10471 extends outside of the rotatable members. Thus, the rotatable member 10562 need not define a jaw pivot opening, as shown above in some embodiments.

As shown, the tool assembly 10465 has a rear pivot and forward grip topology. Specifically, the jaw pivot axis $A_{JP}$ is further from the jaw tip than is the central axis $A_2$. Said another way, the central axis $A_2$ is between the jaw pivot axis $A_{JP}$ and the distal end (or grip portion) of the jaw 10462. Further, when the rotatable members rotate to move the end effector from the closed configuration (FIG. 36) to an opened configuration (FIG. 37), the input link angle $\Theta$ increases. In use, the end effector can amplify the input force to produce a higher grip force produced by the jaws than would be produced with a standard single-piece jaw and pulley system. Specifically, the arrangement of the input link $L_1$ (including the input link angle $\Phi_{OFFSET}$) and the applied link $L_A$, together with the range of lengths of the jaws can amplify the grip force.

Figures 38, 39:
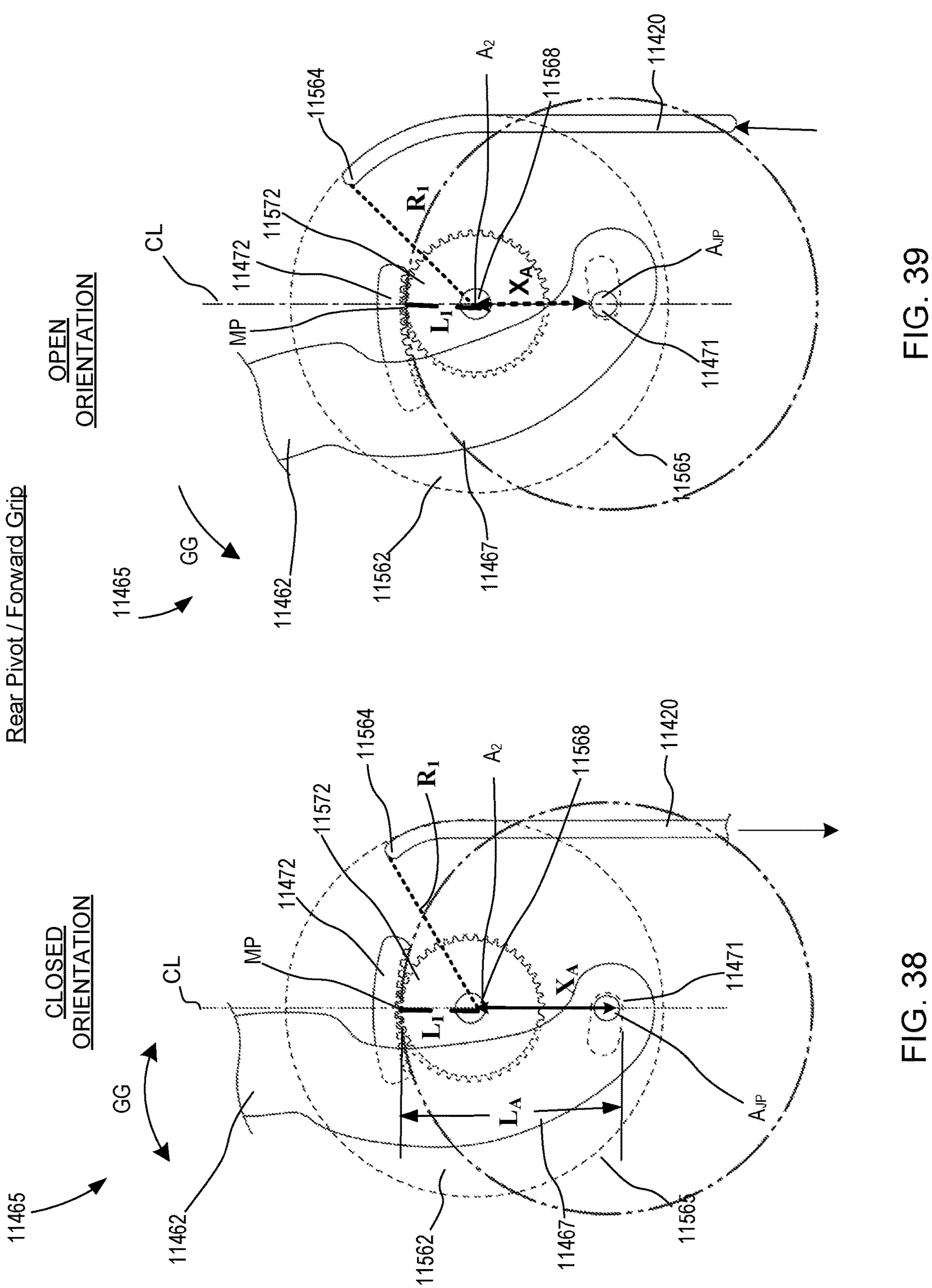
FIGS. 38 and 39 are side views of a tool assembly according to an embodiment having a rear pivot/forward grip topology, shown in a first (closed) configuration (FIG. 38) and a second (open) configuration (FIG. 39).

In some embodiments, a tool assembly can include a jaw that is coupled to a rotatable member in a manner such that the point of connection (and therefore the angular position of the input link $L_1$ is substantially constant regardless of the rotational orientation of the jaw, the rotatable member, and/or the tool assembly. This arrangement can advantageously minimize the impact of the push-pull force (exerted by the jaws) on the grip force (exerted by the jaws). This arrangement can also conserve space and ensure that the rotatable member and associated kinematic links remain within a desired envelope. As one example, FIGS. 38 and 39 are schematic illustrations of a tool assembly 11465 having a rear pivot and forward grip topology, according to an embodiment. Specifically, FIGS. 38 and 39 are side views of a portion of the tool assembly 11465 in a first (closed) configuration (FIG. 38) and a second (open) configuration (FIG. 39). The tool assembly 11465 can be incorporated within any of the end effectors or medical instruments described herein, and can be configured the same or similar to, and function the same or similar to, other tool assemblies described herein. For example, the tool assembly 11465 can be a first tool assembly of an end effector that includes two tool assemblies, similar to the end effectors 4460, 8460, 9460 described herein. Thus, although FIGS. 38 and 39 only show the first tool assembly 11465, it is understood that an end effector can include the first tool assembly 11465 and a second tool assembly (not shown) that are separate components that cooperatively function to form the end effector. Aspects of the first tool assembly 11465 (e.g., identification of kinematic links formed by the first tool assembly) are applicable to a second tool assembly (not shown). Moreover, certain aspects of the tool assembly 11465 and the end effector in which the tool assembly 11465 is included are not described in detail below, but rather are understood to be similar to aspects of the end effectors (e.g., the end effectors 4460, 8460, 9460) described herein. For example, although FIGS. 38 and 39 do not show a clevis, it is understood that the tool assembly 11465 can be rotatably coupled to a central axis $A_2$ of a clevis (similar to the clevis 4610, 8610, 9610 or any other clevis as shown herein).

The tool assembly 11465 includes a jaw 11462 coupled to a rotatable member 11562. Like the jaws 4462, 8462, and 9462, the jaw 11462 includes a distal portion and a proximal portion 11467. The proximal portion 11467 includes a rotatable member connector 11472, which couples the jaw 11462 to and transfers forces from its mating rotatable member 11562. As shown, the rotatable member connector 11472 includes a toothed portion (which functions as an internal gear) that meshes with the toothed portion of the output connector 11572 of the rotatable member 11562. The rotatable member connector 11472 can be a rack or curved portion and can be coupled to the jaw 11462 in any suitable manner. In some embodiments, the rotatable member connector 11472 can be monolithically formed with the jaw 11462. Additionally, the proximal portion 11467 of the jaw 11462 is rotatably coupled to the proximal portion of a second jaw (not shown) by a jaw pivot pin 11471, which defines a jaw pivot axis $A_{JP}$. The distal portions (not shown) of the two jaws function as grip portions to cooperatively contact tissue, grasp a needle, or perform other operations, as shown and described above with reference to the jaws 4462 and 4482 and the jaws 8462 and 8482.

The rotatable member 11562 can be any suitable structure for operatively coupling the jaw 11462 to the tension member 11420, such as a pulley. The rotatable member 11562 is rotatably coupled to the clevis (not shown) about the central axis $A_2$. The rotatable member 11562 includes an input connector 11564 and an output connector 11572, and defines a central opening 11568 and a jaw pivot opening (not identified, but that can be similar to the jaw pivot opening 2569 described above). A central pin can be coupled within the central opening 11568 to allow the rotatable member 11562 and a second rotatable member (of a second tool assembly, not shown) to rotate relative to the clevis about the central axis $A_2$. A tension member 11420 is coupled to the rotatable member 11562 at the input connector 11564. The tension member 11420 can be any suitable connector that transfers force from a mechanical structure (not shown) to the tool assembly 11465, such as a cable, a band, or a push-pull rod. The tension member 11420 is coupled to the rotatable member 11562 at a first input radius $R_1$ from the central axis $A_2$. Thus, when an input force is applied by the tension member 11420 onto the rotatable member 11562, an input torque (analogous to the input torque $T_{in}$ shown in the free-body diagram of FIG. 14) is produced about the central axis $A_2$ to rotate the rotatable member 11562 about the central axis $A_2$. Additionally, the rotatable member 11562 defines a rotatable member envelope 11565 as the cylindrical volume about the central axis $A_2$ that has an envelope radius equal to the outer-most radius of the rotatable member 11562. In some embodiments, the rotatable member envelope 11565 has an envelope radius equal to the outer-most portion of the rotatable member 11562. In some embodiments, the rotatable member envelope 11565 is the same as a rotatable member envelope defined by the second rotatable member.

As shown, the output connector 11572 has a toothed portion (which functions as a gear) that couples the jaw 11462 to the rotatable member 11562 to transfer forces from the rotatable member 11562 to the jaw 11462. The toothed portion of the output connector 11572 engages the toothed portion of the rotatable member connector 11472 along a length, the center point of which is identified as the mesh point MP. Thus, the mesh point MP is point at which the maximum engagement between the output connector 11572 and the rotatable member connector 11472 occurs. Because the coupling is not a fixed point, but occurs along the length of the rotatable member connector 11472, the mesh point MP remains substantially constant as the rotatable member 11562 and the jaw 11462 rotate.

The output connector 11572 is radially offset from the central axis $A_2$ by a jaw input length, identified as $L_1$. Said another way, the gear portion of the output connector 11572 has a radius $L_1$. Thus, the coupling between the rotatable member 11562 and the jaw 11462 defines a kinematic input link identified as $L_1$. Unlike the tool assemblies 8465, 9465, and 10465, however, the input link $L_1$ does not rotate about the central axis $A_2$. Thus, the input link $L_1$ and the end effector center line CL form an input link angle that remains substantially constant when the rotatable member 11562 rotates about the central axis $A_2$. In this embodiment, the input link angle remains substantially zero. Specifically, when the end effector is in the closed configuration (see FIG. 38), the input link $L_1$ is substantially coaxial with the center line CL, and the input link angle is zero. When the rotatable member rotates towards the open position (see FIG. 39), the input link angle remains zero. As shown, the output connector 11572 and the kinematic link $L_1$ are within the rotatable member envelope 11565. Similarly stated, the jaw input length $L_1$ is less than or equal to the to the first input radius $R_1$.

The proximal portion 11467 of the jaw 11462 includes the rotatable member connector 11472, which couples the jaw 11462 to and transfers forces from the rotatable member 11562. Thus, when the input torque applied to the rotatable member 11562 by the tension member 11420 is transferred to the jaw 11462, the jaw 11462 rotates relative to the second jaw (and also the clevis; not shown) about the jaw pivot axis $A_{JP}$, as shown by the arrow GG. The jaw pivot axis $A_{JP}$ is offset from the central axis $A_2$ along an end effector center line CL, which is defined between (and normal to) the central axis $A_2$ and the jaw pivot axis $A_{JP}$ when the end effector is in its closed configuration. The offset distance between the jaw pivot axis $A_{JP}$ and the central axis $A_2$ is indicated as $X_A$. The jaw pivot axis $A_{JP}$ is also offset from the rotatable member connector 11472 by a jaw applied length, identified as $L_A$. Thus, the coupling of the jaws at the jaw pivot pin 11471 and the coupling of the jaw 11462 and the rotatable member 11562 at the rotatable member connector 11472 define a kinematic applied link identified as $L_A$. Similar to the input link, the applied link $L_A$ does not substantially rotate about the jaw pivot axis $A_{JP}$. The applied input link $L_A$ and the end effector center line CL form an applied link angle that changes only minimally (if at all) when the jaw 11462 rotates about the central axis $A_2$ and the jaw pivot axis $A_{JP}$. When the end effector is in the closed configuration (see FIG. 38), the applied link is substantially coaxial with the center line CL and the applied link angle is zero. When the rotatable member rotates towards the open position (see FIG. 39), because the mesh point MP does not move, the applied link angle only changes to the extent that the jaw pivot axis $A_{JP}$ changes. As shown, the jaw pivot axis $A_{JP}$ and the kinematic link $L_A$ are within the rotatable member envelope 11565.

As shown, the tool assembly 11465 has a rear pivot and forward grip topology. Specifically, the jaw pivot axis $A_{JP}$ is further from the jaw tip than is the central axis $A_2$. Said another way, the central axis $A_2$ is between the jaw pivot axis $A_{JP}$ and the distal end (or grip portion) of the jaw 11462. In use, the end effector can amplify the input force to produce a higher grip force produced by the jaws than would be produced with a standard single-piece jaw and pulley system. Specifically, the arrangement of the input link $L_1$ and the applied link $L_A$, together with the range of lengths of the jaws can amplify the grip force.

Although the end effectors described herein are shown as having tool assemblies that include a jaw coupled to a pulley having a substantially circular shape (e.g., the first pulley 8562), in other embodiments, any of the instruments described herein can include a pulley or rotatable member having any suitable shape. For example, although the end effector 4460 is shown as having a pulley characterized by a constant input radius $R_1$, in other embodiments, the end effector 4460 or any of the other end effectors described herein can include a pulley or rotatable member having a variable input radius. In some embodiments, an end effector can include a non-circular pulley (e.g., a pulley having an oval, oblong, or egg-like shape). Positioning the input connector (e.g., the point at which the input force is applied) at the largest radius will produce a higher input torque than would occur with a smaller, constant radius design.

Figure 40:
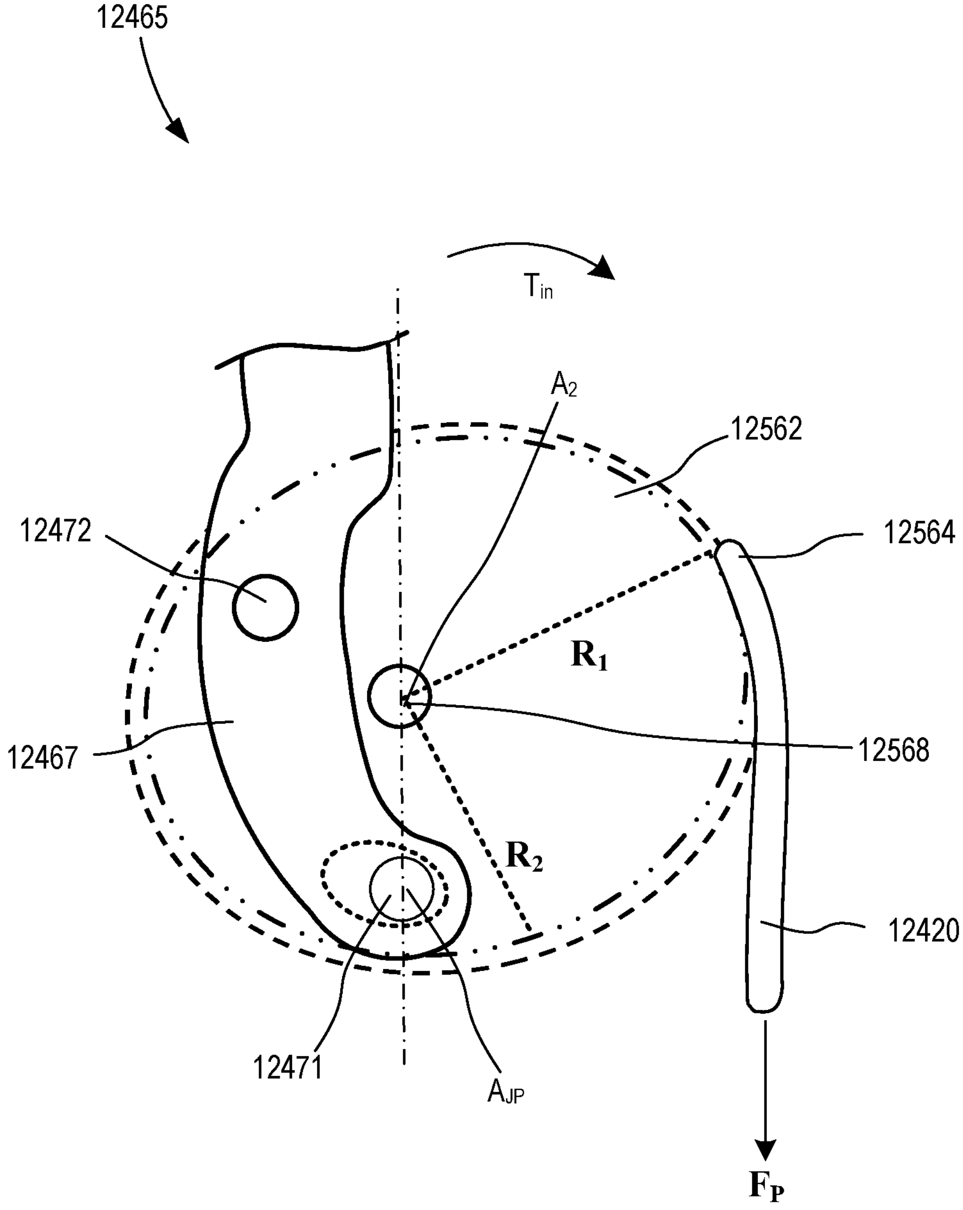
FIG. 40 is a side view of a tool assembly according to an embodiment having a non-circular pulley.

FIG. 40 is a schematic illustration of a distal end portion of a tool assembly 12465 of an end effector having a rear pivot and forward grip topology with a non-circular pulley, according to an embodiment. The tool assembly 12465 can be incorporated within any of the end effectors or medical instruments described herein, and can be configured the same or similar to, and function the same or similar to, other tool assemblies described herein. For example, the tool assembly 12465 can be a first tool assembly of an end effector that includes a second tool assembly, similar to the end effectors 4460, 8460, and 9460 described above. Thus, certain aspects of the tool assembly 12465 and the end effector in which the tool assembly 12465 is included are not described in detail below, but rather are understood to be similar to aspects of the end effectors (e.g., the end effectors 4460, 8460, or 9460) described herein. For example, although FIG. 40 does not show a clevis, it is understood that the tool assembly 12465 can be rotatably coupled to a central axis $A_2$ of a clevis (similar to the clevis 4610 or any other clevis as shown herein).

The tool assembly 12465 includes a jaw 12462 coupled to a pulley 12562. Like the jaw 4462, the jaw 12462 includes a distal portion and a proximal portion 12467. The proximal portion 12467 includes a pulley connector 12472, which couples the jaw 12462 to and transfers forces from its mating pulley 12562. Additionally, the proximal portion 12467 of the jaw 12462 is rotatably coupled to the proximal portion of a second jaw (not shown) by a jaw pivot pin 12471, which defines a jaw pivot axis $A_{JP}$. The distal portions of the two jaws function as grip portions to cooperatively contact tissue, grasp a needle, or perform other operations, as shown and described above with reference to the jaws 4462 and 4482.

The pulley 12562 is a non-circular member (e.g., an oval or egg-shaped member) that is rotatably coupled to the clevis (not shown) about the central axis $A_2$. In some embodiments, the pulley 12562 is characterized by a larger, major radius $R_1$) and a smaller, minor radius $R_2$. The pulley 12562 includes an input connector 12564 and an output connector 12572, and defines a central opening 12568. A central pin can be coupled within the central opening 12568 to allow the pulley 12562 and a second pulley (of a second tool assembly, not shown) to rotate relative to the clevis about the central axis $A_2$. A cable 12420 is coupled to the pulley 12562 at the input connector 12564, which is at the major radius $R_1$ (from the central axis $A_2$). Thus, when an input pulley force $F_P$ is applied by the cable 12420 onto the pulley 12562, an input torque $T_{in}$ is produced about the central axis $A_2$ to rotate the pulley 12562, as shown by the arrow EE. As shown, the major radius $R_1$ is larger than the nominal radius of the pulley 12562 and the minor radius $R_2$. Thus, the input torque $T_{in}$ is greater than that which would be produced by applying the input pulley force $F_P$ to a smaller-sized, constant radius pulley. In this manner, the end effector can amplify the input pulley force $F_P$ to produce a higher grip force (e.g., Fgrip as described herein; see e.g., FIG. 14) produced by the jaws than would be produced with a circular shaped pulley. Moreover, an end effector having a non-circular shape can amplify the input force $F_P$ to produce a higher grip force than would be produced with a single-piece design or the two-piece designs described herein. Specifically, the oval shape of the pulley 12562 increases the moment arm upon which the input force $F_P$ is exerted, thereby increasing the output grip force. Although the input connector 12564 is shown as being at the major radius $R_1$, in other embodiments, the input connector 12564 can be at any suitable location along the oval-shaped pulley 12562.

Although the end effectors described herein are shown as having two-piece tool assemblies (i.e., that include a jaw coupled to a pulley) to facilitate increasing the amplification of the input force, in other embodiments, certain aspects described herein can be included in end effectors having single-piece tool assemblies. Similarly stated, in some embodiments, an end effector can include single-piece jaws that are configured to amplify the input force to maximize the grip force. For example, in some embodiments, an end effector can include jaws having a non-circular pulley portion to increase the input torque for a given input force.

Figure 41:
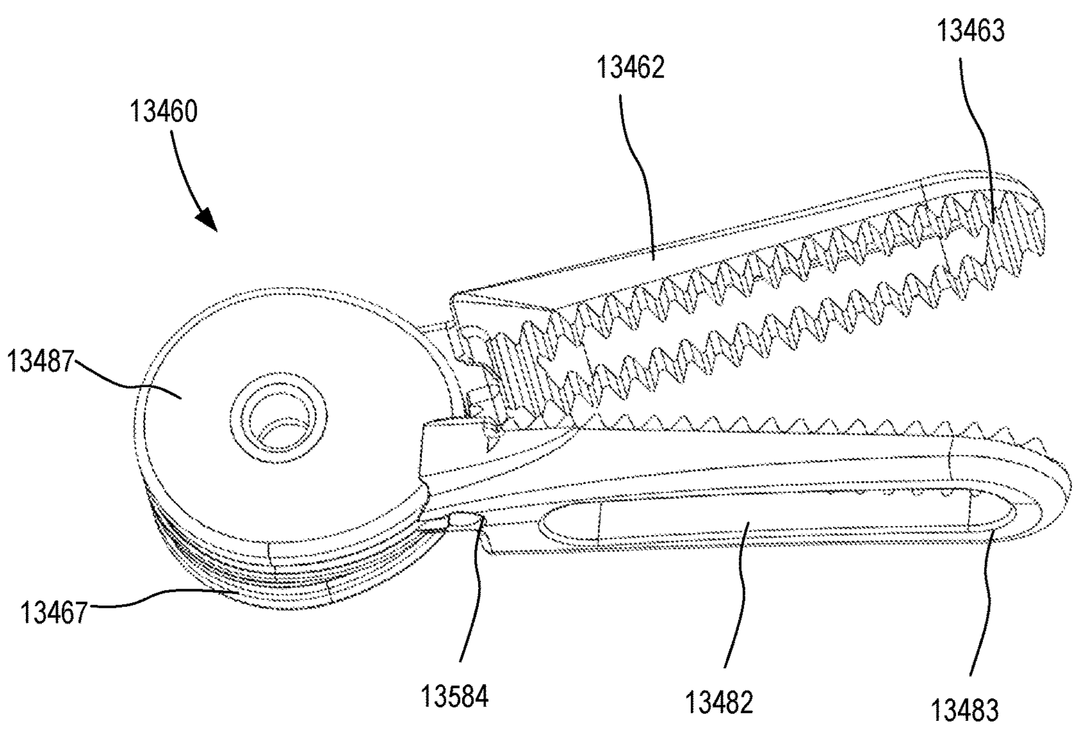
FIGS. 41 and 42 are a perspective view (FIG. 41) and a side view (FIG. 42) of a tool assembly according to an embodiment having single-piece jaws with an oval shape.
Figure 42:
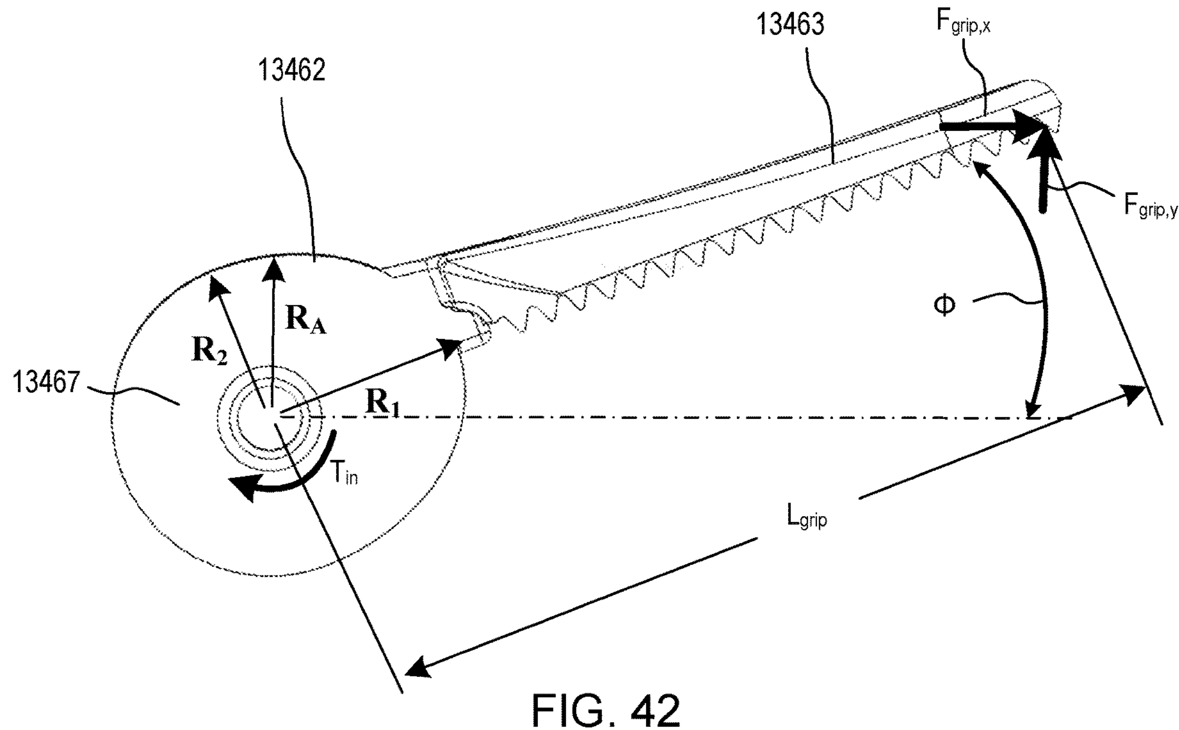

FIG. 41 shows and end effector 13460 according to an embodiment. FIG. 42 shows the first jaw 13462 of the end effector. The end effector 13460 includes a first jaw 13462 and a second jaw 13482. The first jaw 13462 includes a distal portion 13463 and a proximal portion 13467 and the second jaw 13482 includes a distal portion 13483 and a proximal portion 13487. The proximal portions 13467, 13487 each include an input connector (only the second input connector 13584 for the second jaw 13482 is shown). In use a cable (not shown) can be coupled to the second input connector 13584. The distal portions of the two jaws function as grip portions to cooperatively contact tissue, grasp a needle, or perform other operations, as shown and described above.

The proximal portions 13467, 13487 of each jaw are a non-circular (e.g., they are oval or egg-shaped member). As shown in FIG. 42, the proximal portion 13467 is characterized by a larger, major radius $R_1$) and a smaller, minor radius $R_2$. In some embodiments, the input connector is located at the major radius $R_1$. Thus, when an input pulley force is applied by the cable (not shown) onto the proximal portion 13467 of the first jaw 13462, an input torque $T_{in}$ is produced about the central axis to rotate the jaw 13462. As shown, the major radius $R_1$ is larger than the nominal radius of the proximal portion 13467 and the minor radius $R_2$. Thus, the input torque $T_{in}$ is greater than that which would be produced by applying the input pulley force $F_P$ to a smaller-sized, constant radius pulley. In this manner, the end effector can amplify the input pulley force to produce a higher grip force produced by the jaws than would be produced with a standard constant radius (i.e., circular) single-piece jaw. Specifically, the oval shape of the proximal portion 13467 increases the moment arm upon which the input force is exerted, thereby increasing the output grip force.

FIG. 42 provides a free-body diagram showing the geometry of the first jaw 13462. The moment balance taken around the central axis $A_2$ is provided by Equation (22), which can be reduced to produce Equation (23) axis.

$$\Sigma M_{dp}=0 \quad \text{Eq (22):}$$

$$T_{force}+F_{Grip,y}\times L_{Grip}\cos(\Phi)=0 \quad \text{Eq (23):}$$

The equation for the input torque $T_{in}$ (or $T_{force}$, as indicated in Equation (23) is given by the product of the input force and the moment arm (in this case, $R_1$). Thus, by increasing the moment arm, the grip force $F_{grip,y}$ can be increased.

In other embodiments, the input connector is located at any suitable location along the proximal portion 13467, for example, at the actuation radius $R_A$. In yet other embodiments, the point of attachment is not at a fixed location along the proximal portion 13467, but will instead vary with the orientation of the jaws, the orientation of the wrist assembly (not shown), or both. In such embodiments, the amount of force amplification will vary with the orientation of the jaws, the orientation of the wrist assembly, or both. For example, in the jaw orientation depicted in FIG. 42, the moment arm may be based an intermediate radius between the major radius $R_1$ and minor radius $R_2$ (shown as the actuation radius $R_A$). At this orientation (e.g., at the angle $\Phi$), the force amplification is less than the maximum possible amplification. For this embodiment, the maximum force amplification will only occur when the jaw is fully open (90 degrees from the CL) and the cable exits the jaw at $R_1$. Conversely, when the jaw is fully closed there will be no mechanical advantage over a circular pulley of radius $R_2$ since the moment arm will be based on the minor radius at that jaw orientation.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a patient-side cart, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys, or the like. Further, any of the links, tool members, tension members, or components described herein can be constructed from multiple pieces that are later joined together. For example, in some embodiments, a link can be constructed by joining together separately constructed components. In other embodiments, however, any of the links, tool members, tension members, or components described herein can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

For example, although the instrument 8400 includes the wrist 8500, which allows for an additional degree of freedom (e.g., pitch rotation about the first axis of rotation $A_1$), in other embodiments, the instrument 8400 or any other instruments described herein need not include a wrist assembly. In some embodiments, an instrument can include an end effector similar to the end effector 8460, which allows for amplification of the input forces, but without including a wrist mechanism.

What is claimed is:

1. An apparatus, comprising:

a clevis;

a central pin coupled to the clevis;

a first tool assembly coupled to the clevis via the central pin, the first tool assembly comprising a first pulley and a first jaw, the first pulley comprising a first input connector and a first output connector, the first input connector coupled to a first tension member, a first central opening defined by the first pulley, the central pin extending through the first central opening, the first pulley rotating about the central pin when a first input torque is exerted by the first tension member, a first jaw pivot opening being defined within the first pulley, the first jaw comprising a first pulley connector coupled to the first output connector, and the first jaw rotating when a portion of the first input torque is transferred to the first jaw via an interface between the first pulley connector and the first output connector;

a second tool assembly coupled to the clevis via the central pin, the second tool assembly comprising a second pulley and a second jaw, the second pulley comprising a second input connector and a second output connector, the second input connector coupled to a second tension member, a second central opening defined by the second pulley, the central pin extending through the second central opening, the second pulley rotating about the central pin when a second input torque is exerted by the second tension member, a second jaw pivot opening being defined within the second pulley, the second jaw comprising a second pulley connector coupled to the second output connector, and the second jaw rotating when a portion of the second input torque is transferred to the second jaw via an interface between the second pulley connector and the second output connector; and a jaw pivot pin coupling the first jaw to the second jaw via a jaw pivot axis, the first jaw and the second jaw configured to rotate relative to each other about the jaw pivot axis, and the jaw pivot pin extending through the first jaw pivot opening of the first pulley and the second jaw pivot opening of the second pulley.

2. The apparatus of claim 1, wherein:

the central pin defines a central axis about which the first pulley and the second pulley rotate; and the jaw pivot axis is offset from the central axis.

3. The apparatus of claim 1, wherein:

the first jaw pivot opening is elongated;

the second jaw pivot opening is elongated; and the jaw pivot pin is configured to translate relative to the central pin within the first jaw pivot opening and the second jaw pivot opening when the first jaw rotates relative to the clevis.

4. The apparatus of claim 3, wherein:

the first jaw pivot opening is defined by a first pulley side wall;

the second jaw pivot opening is defined by a second pulley side wall; and translation of the jaw pivot pin is constrained by the first pulley side wall and the second pulley side wall.

5. The apparatus of claim 3, wherein:

the first jaw pivot opening is a first curvilinear path;

the second jaw pivot opening is a second curvilinear path, the second curvilinear path being different from the first curvilinear path; and the jaw pivot pin translates along a jaw pivot pin path defined by an intersection of the first curvilinear path and the second curvilinear path.

6. The apparatus of claim 1, wherein:

the first jaw defines a first central slot;

the central pin being disposed within the first central slot; and the first central slot being sized to allow the first jaw to translate relative to the central pin when the first jaw and the second jaw rotate relative to each other about the jaw pivot axis.

7. The apparatus of claim 1, wherein the first pulley and the second pulley are between the first jaw and the second jaw.

8. The apparatus of claim 1, wherein:

the first jaw comprising a first grip portion at a distal end portion of the first jaw; and the second jaw comprising a second grip portion at a distal end portion of the second jaw.

9. The apparatus of claim 8, wherein:

the first pulley connector of the first jaw is between the first grip portion and the jaw pivot pin; and the first central opening of the first pulley is between the first input connector and the first jaw pivot opening.

10. The apparatus of claim 8, wherein:

the jaw pivot pin is between the first grip portion and the first pulley connector of the first jaw; and the first central opening of the first pulley is between the first input connector and the first jaw pivot opening.

11. The apparatus of claim 1, wherein:

the central pin defines a central axis about which the first pulley and the second pulley rotate;

the first input connector is radially offset from the central axis by a first input radius;

a first pulley envelope is defined as a cylindrical volume about the central axis having an envelope radius equal to the first input radius; and the first output connector, the first jaw pivot opening, the first pulley connector, and the jaw pivot axis are within the first pulley envelope.

12. The apparatus of claim 11, wherein:

the first output connector is radially offset from the central axis by a first jaw input length;

the jaw pivot axis is radially offset from the central axis by a jaw pivot axis distance; and each of the first jaw input length and the jaw pivot axis distance being less than the first input radius.

13. The apparatus of claim 12, wherein the first output connector and the first pulley connector are each offset from the jaw pivot axis by an applied length that is greater than the first jaw input length.

14. The apparatus of claim 13, wherein the applied length is greater than the first input radius.

15. An apparatus, comprising:

a clevis;

a central pin coupled to the clevis;

a first tool assembly coupled to the clevis via the central pin, the first tool assembly comprising a first pulley and a first jaw, the first pulley comprising a first input connector and a first output connector, the first output connector extending laterally outward from the first pulley, the first input connector coupled to a first tension member, a first central opening defined by the first pulley, the central pin extending through the first central opening, the first pulley rotating about the central pin when a first input torque is exerted by the first tension member, the first jaw comprising a first pulley connector coupled to the first output connector, and the first jaw rotating when a portion of the first input torque is transferred to the first jaw via an interface between the first pulley connector and the first output connector;

a second tool assembly coupled to the clevis via the central pin, the second tool assembly comprising a second pulley and a second jaw, the second pulley comprising a second input connector and a second output connector, the second output connector extending laterally outward from the second pulley in a direction opposite the first output connector, the second input connector coupled to a second tension member, a second central opening defined by the second pulley, the central pin extending through the second central opening, the second pulley rotating about the central pin when a second input torque is exerted by the second tension member, the second jaw comprising a second pulley connector coupled to the second output connector, and the second jaw rotating when a portion of the second input torque is transferred to the second jaw via an interface between the second pulley connector and the second output connector;

the first pulley and the second pulley being between the first jaw and the second jaw; and a single jaw pivot pin coupling the first jaw to the second jaw, the jaw pivot pin having a first end portion coupled to the first jaw and a second end portion coupled to the second jaw, the jaw pivot pin defining a jaw pivot axis, the first jaw and the second jaw being configured to rotate relative to each other about the jaw pivot axis, the jaw pivot axis being offset from the central pin.

16. The apparatus of claim 15, wherein:

the first jaw defines a first central slot;

the second jaw defines a second central slot; and the central pin is within the first central slot and the second central slot; and the first central slot and the second central slot being sized to allow the first jaw and the second jaw to translate relative to the central pin when the first jaw and the second jaw rotate relative to each other about the jaw pivot axis.

17. The apparatus of claim 16, wherein:

the first central slot is defined by a first jaw side wall;

the second central slot is defined by a second jaw side wall; and translation of the first jaw relative to the central pin is constrained by the first jaw side wall and translation of the second jaw relative to the central pin is constrained by the second jaw side wall.

18. An apparatus, comprising:

a clevis;

a central pin coupled to the clevis, the central pin defining a central axis;

a first tool assembly coupled to the clevis via the central pin, the first tool assembly comprising a first pulley and a first jaw, the first pulley comprising a first input connector and a first output connector, the first output connector extending laterally outward from the first pulley, the first input connector being radially offset from the central axis by a first input radius and coupled to a first tension member, a first central opening defined by the first pulley, the central pin extending through the first central opening, the first pulley rotating about the central axis when a first input torque is exerted by the first tension member, a first pulley envelope being defined as a cylindrical volume about the central axis having an envelope radius equal to the first input radius, the first jaw comprising a first pulley connector coupled to the first output connector, and the first jaw rotating when a portion of the first input torque is transferred to the first jaw via an interface between the first pulley connector and the first output connector;

a second tool assembly coupled to the clevis via the central pin, the second tool assembly comprising a second pulley and a second jaw, the second pulley comprising a second input connector and a second output connector, the second output connector extending laterally outward from the second pulley in a direction opposite the first output connector, the second input connector coupled to a second tension member, a second central opening defined by the second pulley, the central pin extending through the second central opening, the second pulley rotating about the central axis when a second input torque is exerted by the second tension member, the second jaw comprising a second pulley connector coupled to the second output connector, and the second jaw rotating when a portion of the second input torque is transferred to the second jaw via an interface between the second pulley connector and the second output connector;

a jaw pivot pin coupling the first jaw to the second jaw via a jaw pivot axis, the first jaw and the second jaw configured to rotate relative to each other about the jaw pivot axis, and the jaw pivot axis being offset from the central axis; and the first output connector, the first pulley connector, and the jaw pivot axis being within the first pulley envelope, wherein:

the first tool assembly and the second tool assembly form an end effector that rotates about the central axis, an end effector center line is defined between the central axis and the jaw pivot axis, the end effector is configured to move between a plurality of open configurations and a closed configuration, the first output connector is radially offset from the central axis to define a first input link, the first input link and the end effector center line define an input link angle, and the input link angle increases when the end effector moves from the closed configuration towards the open configuration.

19. The apparatus of claim 18, wherein:

the first jaw comprises a first grip portion at a distal end portion of the first jaw; and the first pulley connector of the first jaw is between the first grip portion and the jaw pivot pin.

* * * * *